United States Patent
Iida et al.

(10) Patent No.: US 9,903,861 B2
(45) Date of Patent: *Feb. 27, 2018

(54) DEVICE AND METHOD FOR DETECTING AN ANALYTE

(71) Applicant: OSAKA PREFECTURE UNIVERSITY PUBLIC CORPORATION, Sakai-shi, Osaka (JP)

(72) Inventors: Takuya Iida, Sakai (JP); Shiho Tokonami, Sakai (JP)

(73) Assignee: Osaka Prefecture University Public Corporation, Sakai-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/894,452

(22) PCT Filed: May 30, 2014

(86) PCT No.: PCT/JP2014/064496
§ 371 (c)(1),
(2) Date: Nov. 27, 2015

(87) PCT Pub. No.: WO2014/192937
PCT Pub. Date: Dec. 4, 2014

(65) Prior Publication Data
US 2016/0123968 A1    May 5, 2016

(30) Foreign Application Priority Data
May 30, 2013  (JP) ................................. 2013-114312

(51) Int. Cl.
*G01N 21/21*    (2006.01)
*G01N 33/543*   (2006.01)
(Continued)

(52) U.S. Cl.
CPC ..... *G01N 33/54346* (2013.01); *C12Q 1/6834* (2013.01); *G01N 21/21* (2013.01);
(Continued)

(58) Field of Classification Search
CPC .......... C12M 1/00; G01B 11/16; G02B 21/06; C40B 30/04; G01N 21/658
See application file for complete search history.

(56) References Cited

U.S. PATENT DOCUMENTS 4,893,886 A    1/1990  Ashkin et al.
5,198,369 A    3/1993  Itoh et al.
(Continued)

FOREIGN PATENT DOCUMENTS

EP    0 455 125 A2    11/1991
EP    2 560 005 A1    2/2013
(Continued)

OTHER PUBLICATIONS

Restolho et al, On the interfacial behavior of ionic liquids: Surface tensions and contact angles, 2009, Journal of Colloid and Interface Science, 340, 82-86.*
(Continued)

*Primary Examiner* — Narayan Bhat
(74) *Attorney, Agent, or Firm* — Birch, Stewart, Kolasch & Birch, LLP

(57) ABSTRACT

A detection device detects an analyte that may be contained in a specimen. The detection device includes a plurality of gold nanoparticles, an optical trapping light source, an illumination light source, an objective lens, an image pick-up device, and a computation unit. The plurality of gold nanoparticles are each modified with a probe DNA allowing the analyte to specifically adhere thereto. The optical trapping light source emits polarized light for assembling the plurality of gold nanoparticles together. The objective lens
(Continued)

focuses and introduces the polarized light into a liquid containing a specimen and the plurality of gold nanoparticles. The image pick-up device receives light from the liquid. The computation unit detects an analyte based on a signal received from the image pick-up device.

18 Claims, 36 Drawing Sheets

(51) Int. Cl.
  *G01N 21/552* (2014.01)
  *G01N 21/65* (2006.01)
  *G01N 33/53* (2006.01)
  *G01N 33/553* (2006.01)
  *C12Q 1/68* (2018.01)

(52) U.S. Cl.
  CPC ......... *G01N 21/554* (2013.01); *G01N 21/658* (2013.01); *G01N 33/5308* (2013.01); *G01N 33/553* (2013.01); *C12Q 2563/155* (2013.01); *C12Q 2565/628* (2013.01); *G01N 2201/061* (2013.01); *G01N 2201/0683* (2013.01)

(56) References Cited

U.S. PATENT DOCUMENTS

| | | | | |
|---|---|---|---|---|
| 6,361,944 | B1* | 3/2002 | Mirkin | C12Q 1/6837 435/6.11 |
| 8,854,621 | B1* | 10/2014 | Muschol | G01N 21/47 356/336 |
| 2004/0038264 | A1* | 2/2004 | Souza | B82Y 5/00 435/6.12 |
| 2010/0141942 | A1 | 6/2010 | Kim et al. | |
| 2011/0003320 | A1 | 1/2011 | Ito et al. | |
| 2012/0107952 | A1 | 5/2012 | Geddes et al. | |
| 2013/0010300 | A1 | 1/2013 | Tamura et al. | |
| 2013/0252275 | A1 | 9/2013 | Tokonami et al. | |

FOREIGN PATENT DOCUMENTS

| | | |
|---|---|---|
| JP | 4-066873 A | 3/1992 |
| JP | 5-288529 A | 11/1993 |
| JP | 2004-354345 A | 12/2004 |
| JP | 2005-533246 A | 11/2005 |
| JP | 2007-525651 A | 9/2007 |
| JP | 2008-070214 A | 3/2008 |
| JP | 2009-008475 A | 1/2009 |
| JP | 2009-210505 A | 9/2009 |
| JP | 2012-081531 A | 4/2012 |
| WO | WO 2004/007767 A1 | 1/2004 |
| WO | WO 2004/042403 A2 | 5/2004 |
| WO | WO 2005/008222 A2 | 1/2005 |
| WO | WO 2011/129220 A1 | 10/2011 |
| WO | WO 2011/142118 A1 | 11/2011 |
| WO | WO 2012/077756 A1 | 6/2012 |

OTHER PUBLICATIONS

Iida et al, Submillimetre Network Formation by Light-induced Hybridization of Zeptomole-level DNA, 2016, Sci. Rep. 6, 37768, Post art (Year: 2016).*

Iida et al, Submillimetre Network Formation by Light-induced Hybridization of Zeptomole-level DNA, 2016, Sci. Rep. 6, 37768, Post art, Supplementary information, pp. 1-8, Post art (Year: 2016).*

International Search Report issued in PCT/JP2014/064496, dated Aug. 5, 2014.

Extended European Search Report for European Application No. 14804538.8, dated Mar. 27, 2017.

Foultier et al., "Comparison of DNA Detection Methods Using Nanoparticles and Silver Enhancement," IEE Proceedings Nanobiotechnology, vol. 152, No. 1, Feb. 2005, pp. 3-12.

Iida, "Control of Plasmonic Superradiance in Metallic Nanoparticle Assembly by Light-Induced Force and Fluctuations," Journal of Physical Chemistry Letters, vol. 3, Jan. 6, 2012, pp. 332-336.

Mirkin et al., "A DNA-Based Method for Rationally Assembling Nanoparticles into Macroscopic Materials," Nature, vol. 382, Aug. 15, 1996, pp. 607-609.

European Communication, dated Dec. 13, 2017, for European Application No. 14804538.8.

Hansen et al., "Expanding the optical trapping range of gold nanoparticles," Nano letters, vol. 5, No. 10, 2005 (published on web Aug. 31, 2005), pp. 1937-1942.

* cited by examiner

FIG.3
(A)
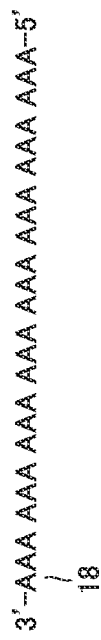
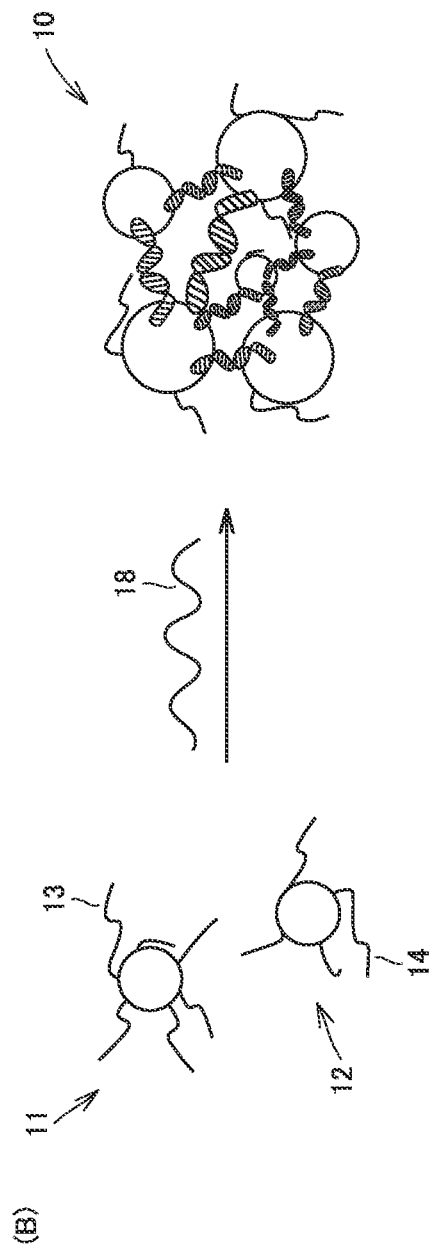
(B)

FIG.5
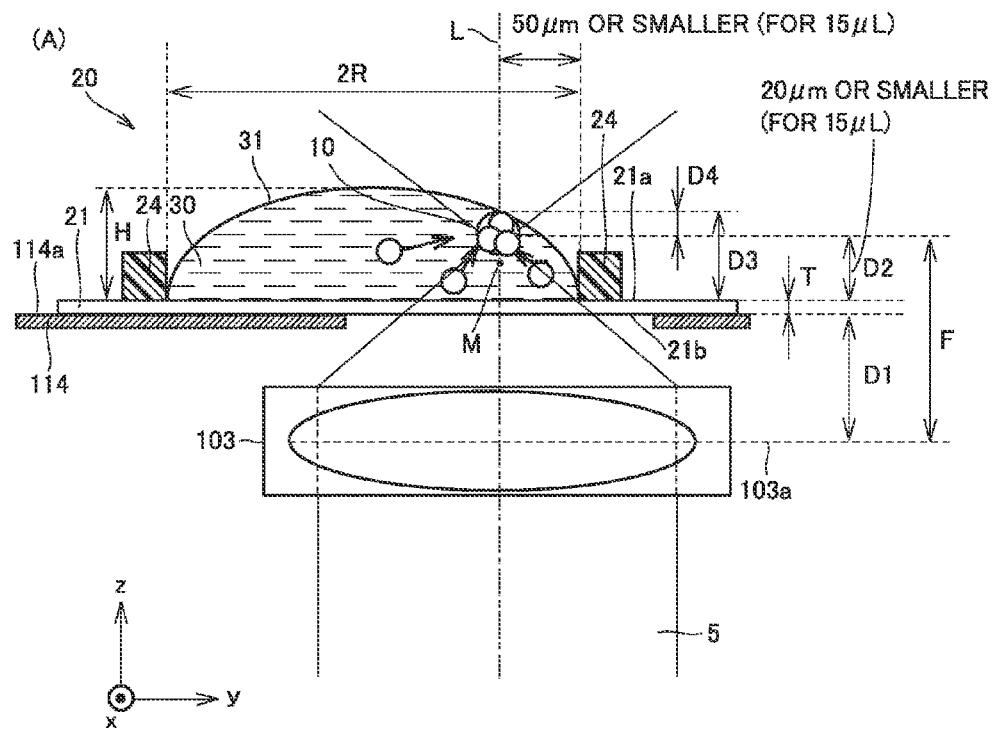
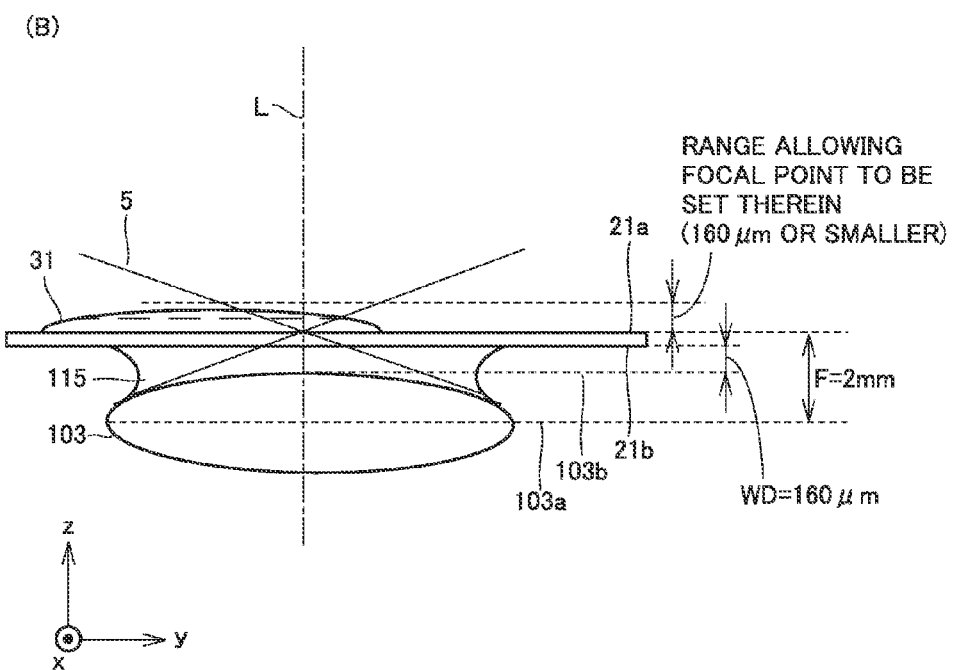

FIG.6
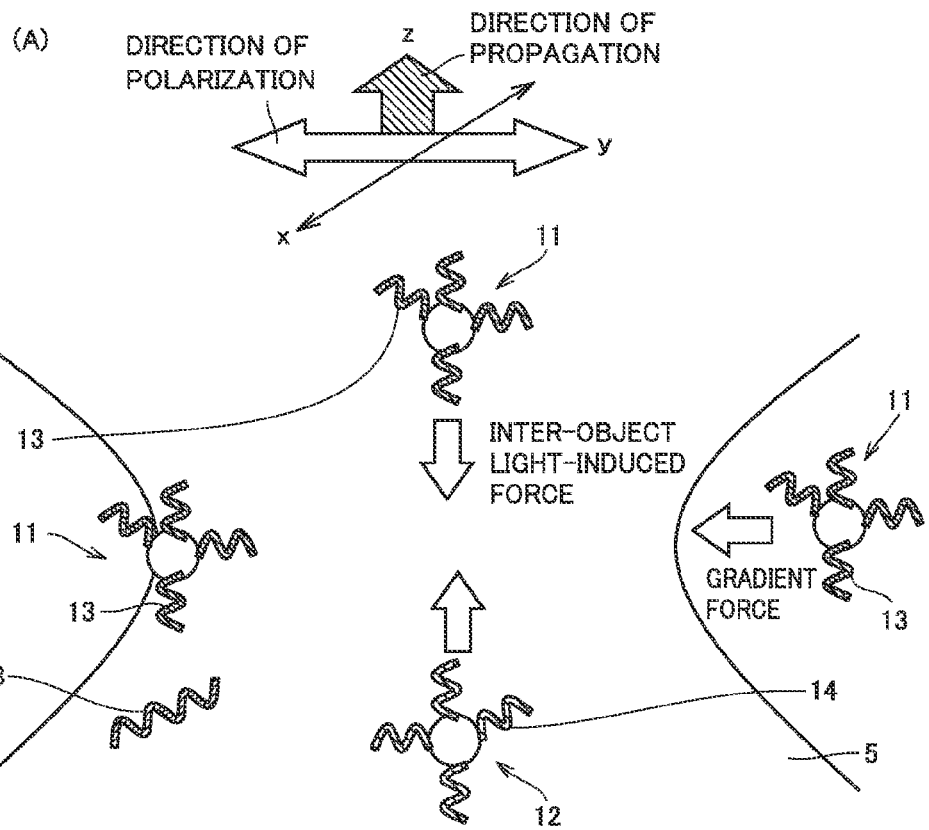
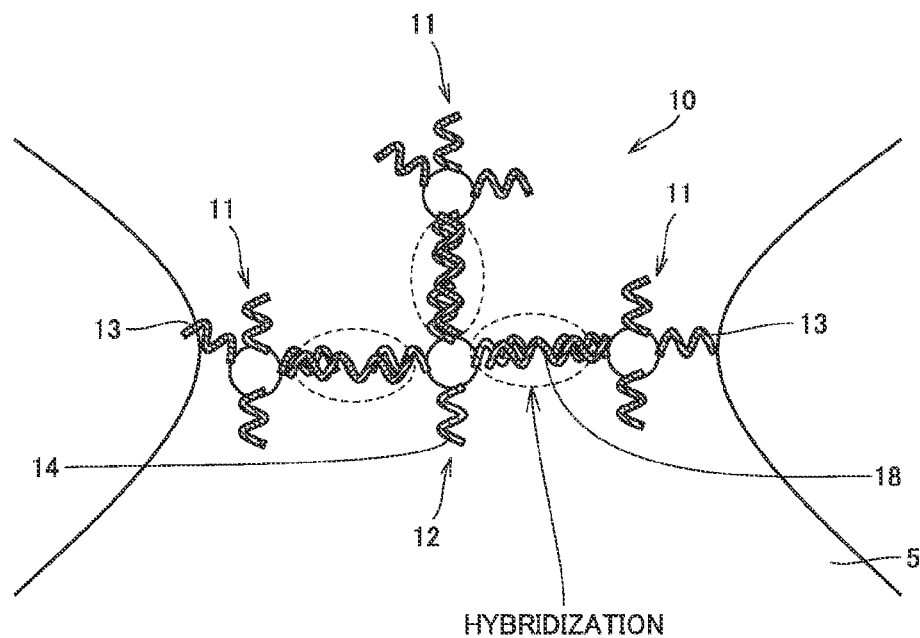

FIG.9
(A)
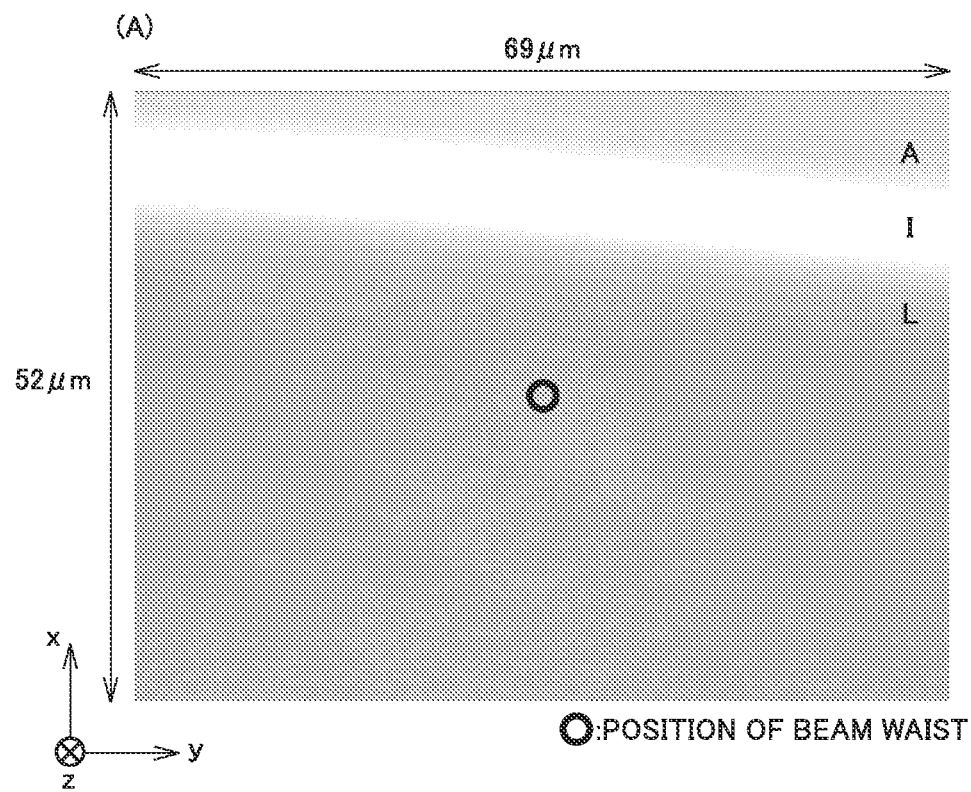
○:POSITION OF BEAM WAIST
(B)
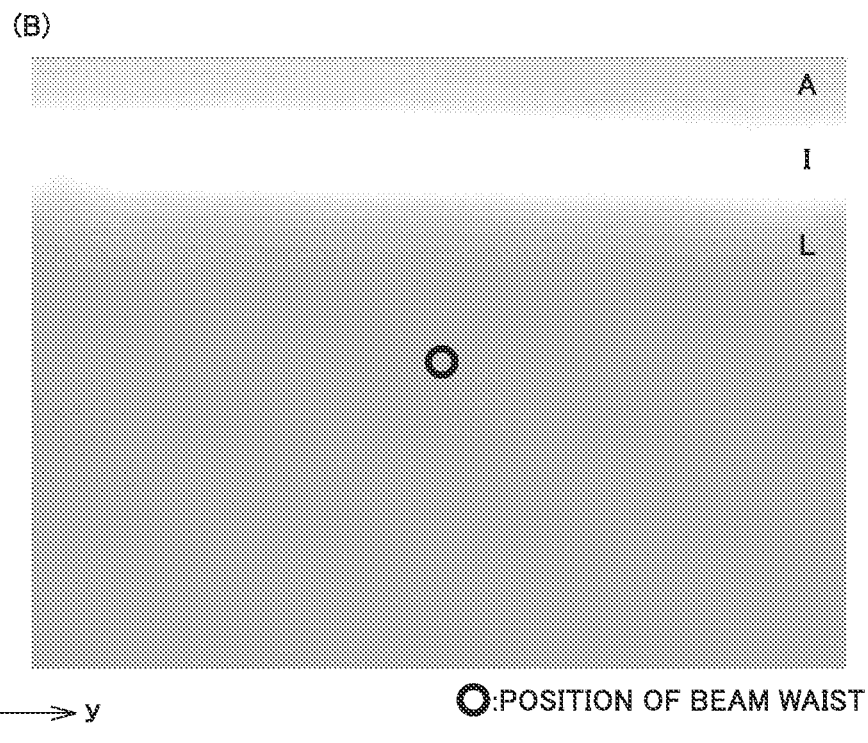
○:POSITION OF BEAM WAIST FIG.12
(A)
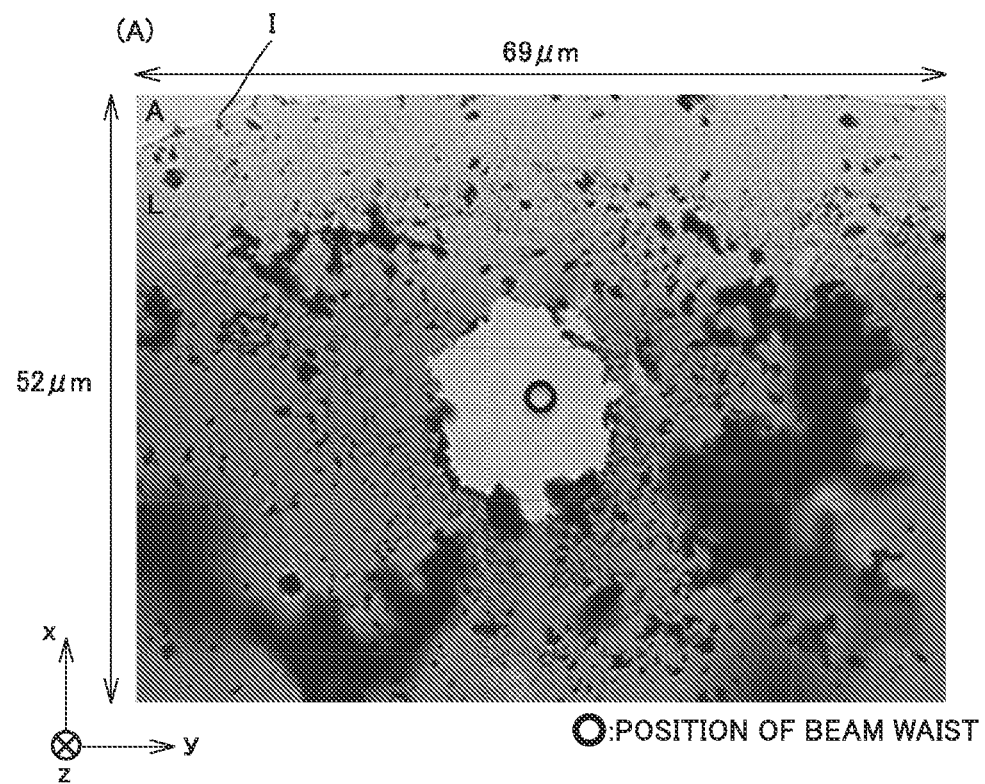
○:POSITION OF BEAM WAIST
(B)
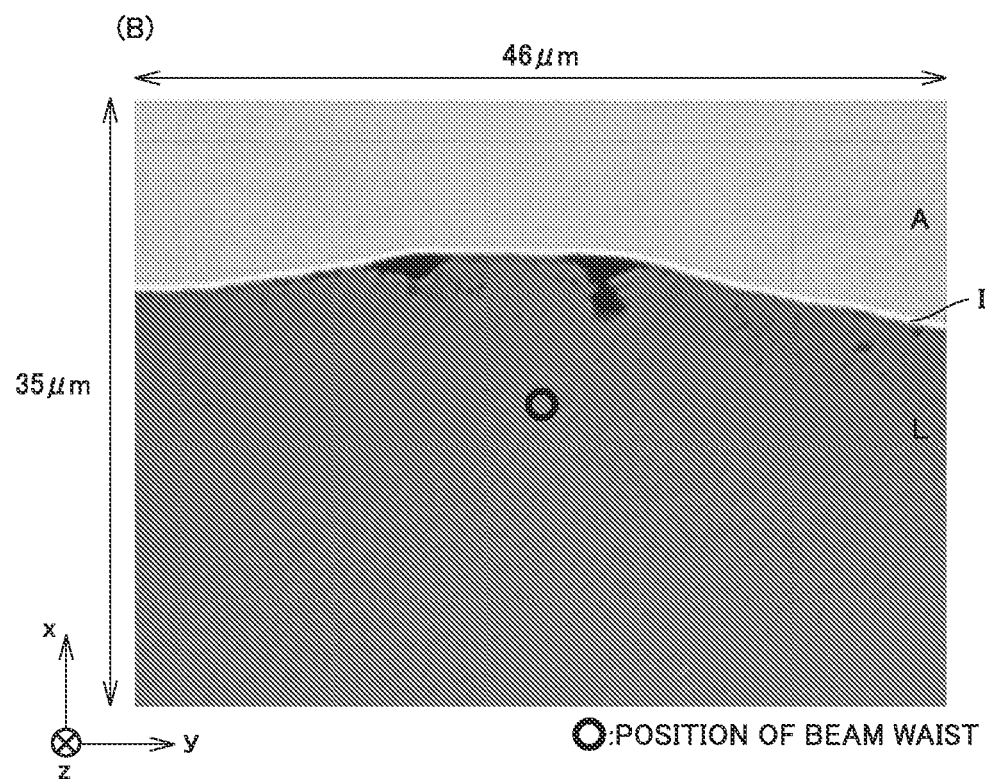
○:POSITION OF BEAM WAIST FIG.14
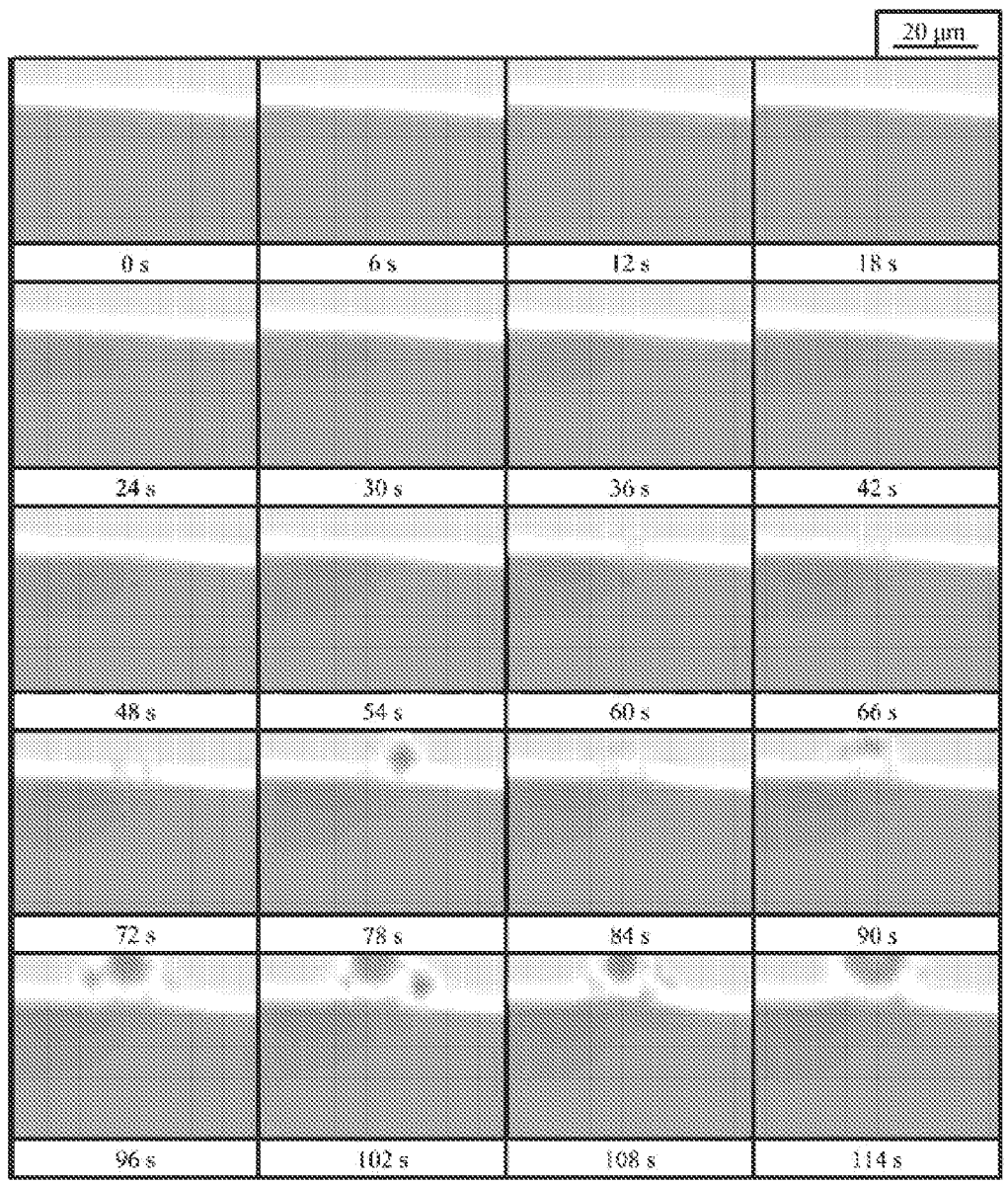
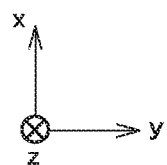

FIG.15
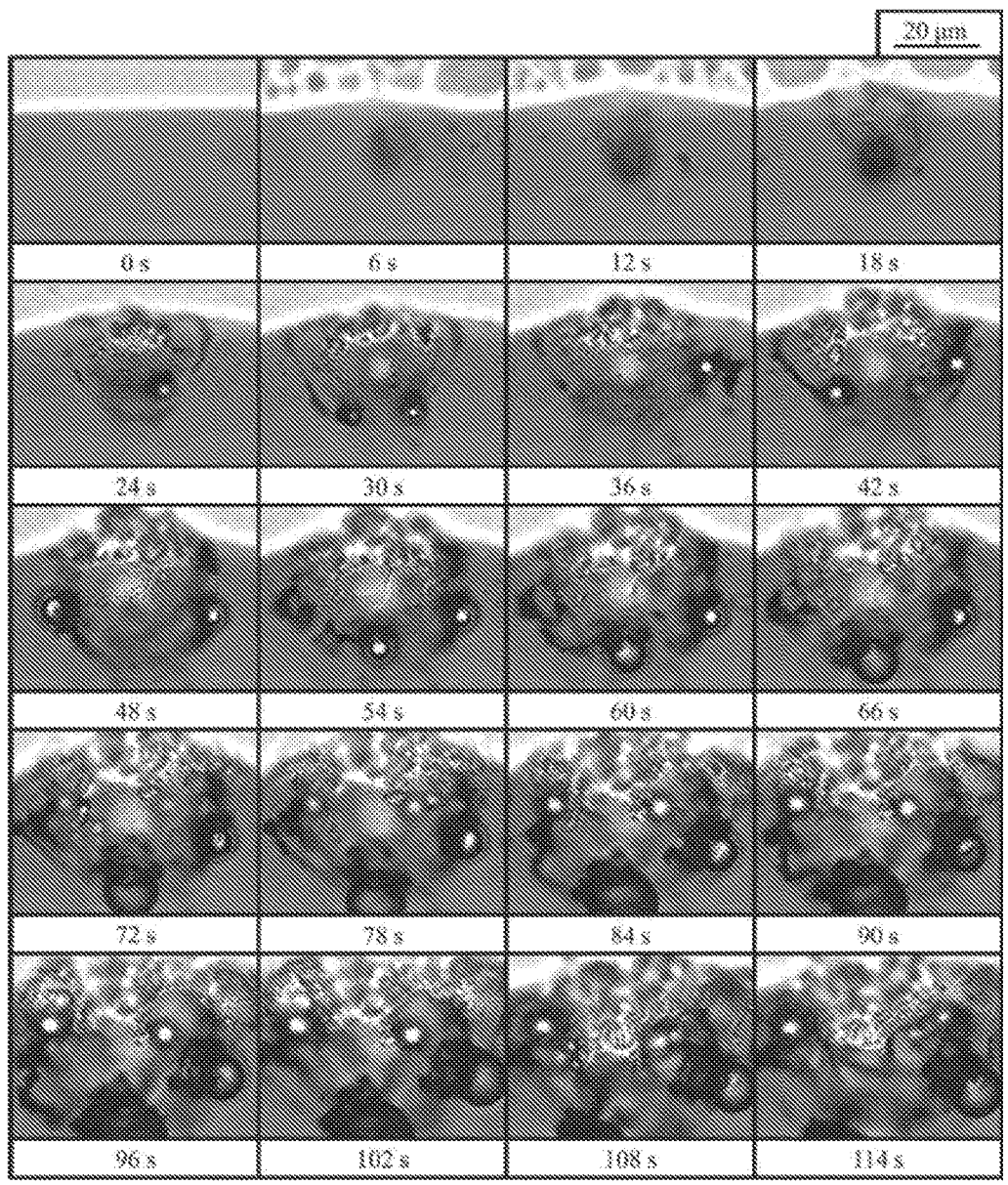
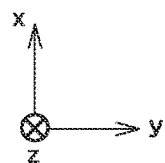

FIG.17
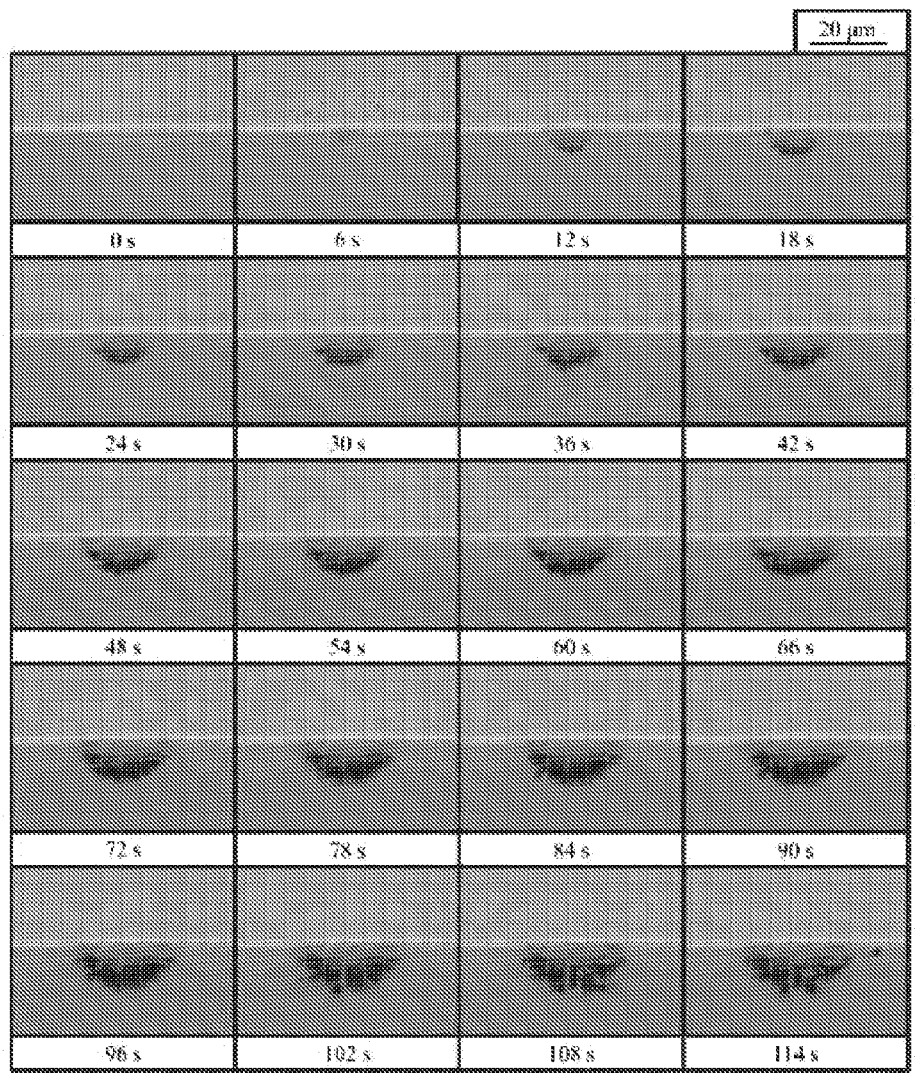
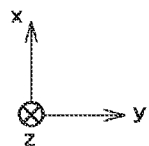

FIG.27
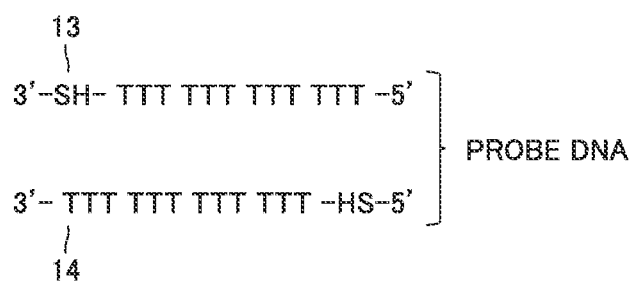
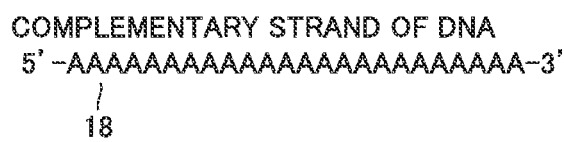
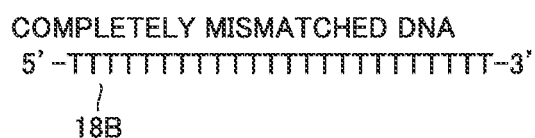
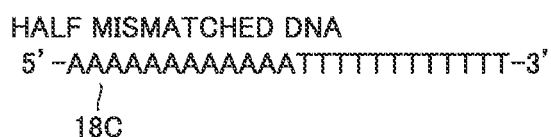
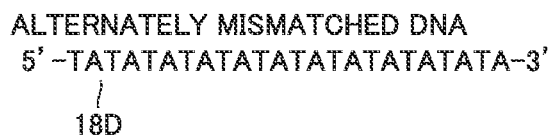

FIG.29
(A)
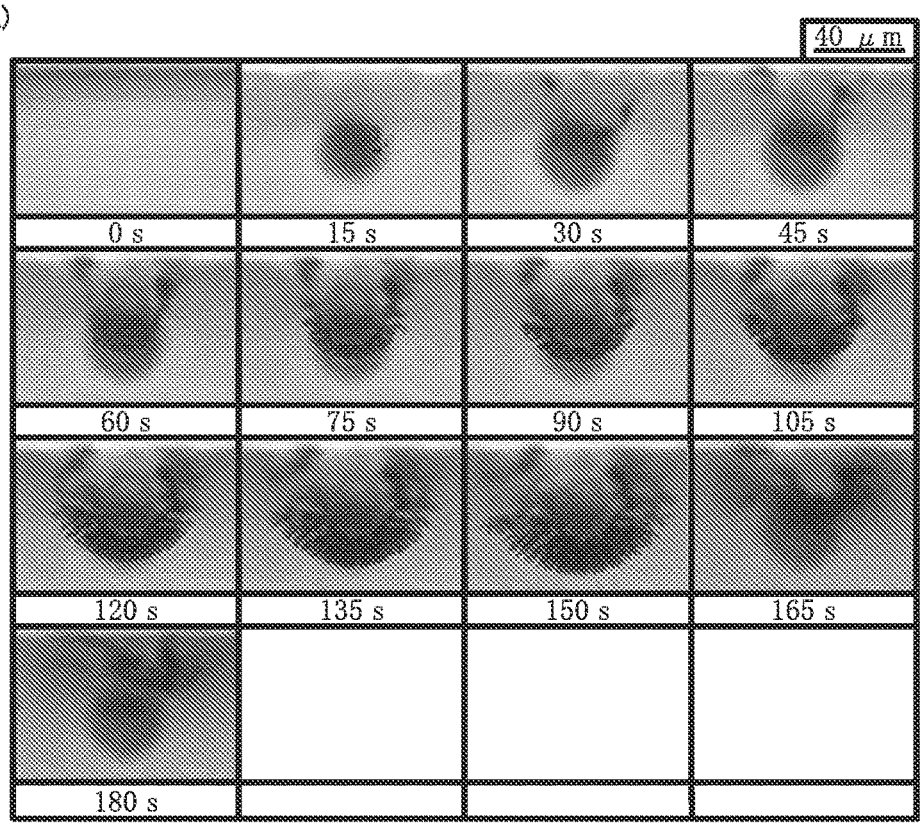
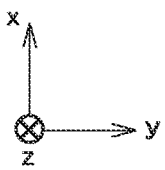
(B)
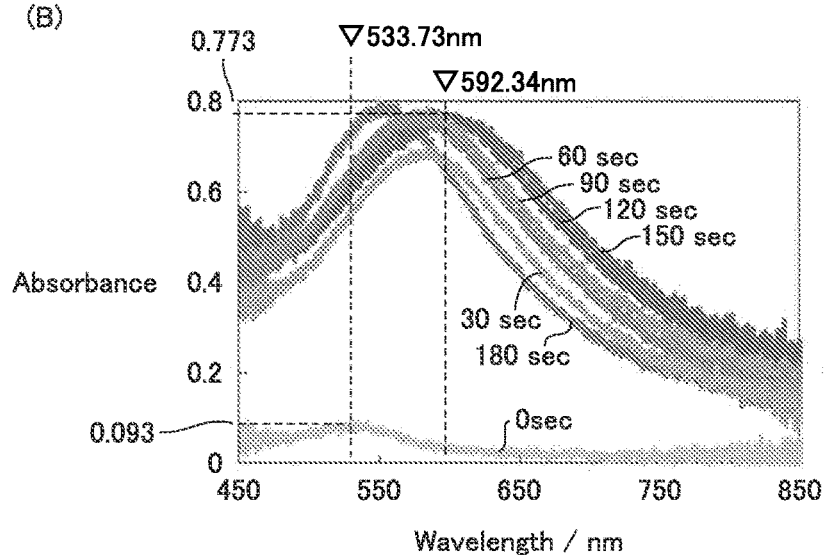

FIG.30
(A)
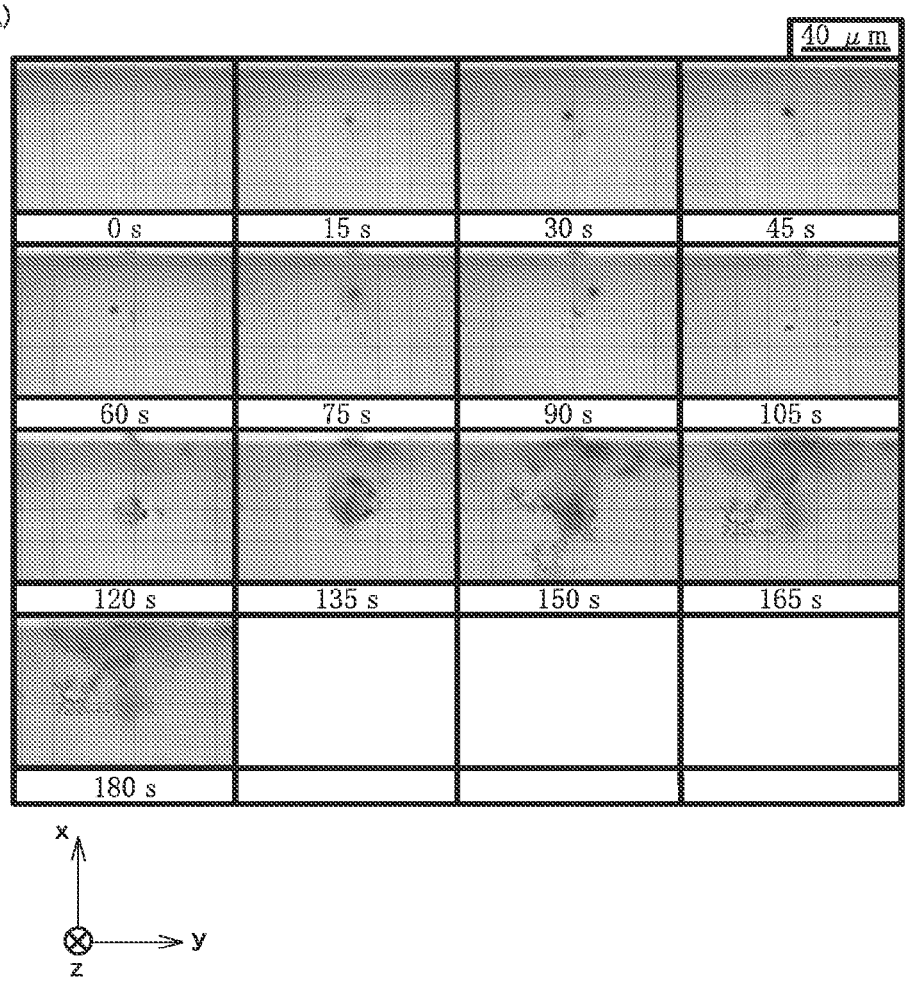
(B)
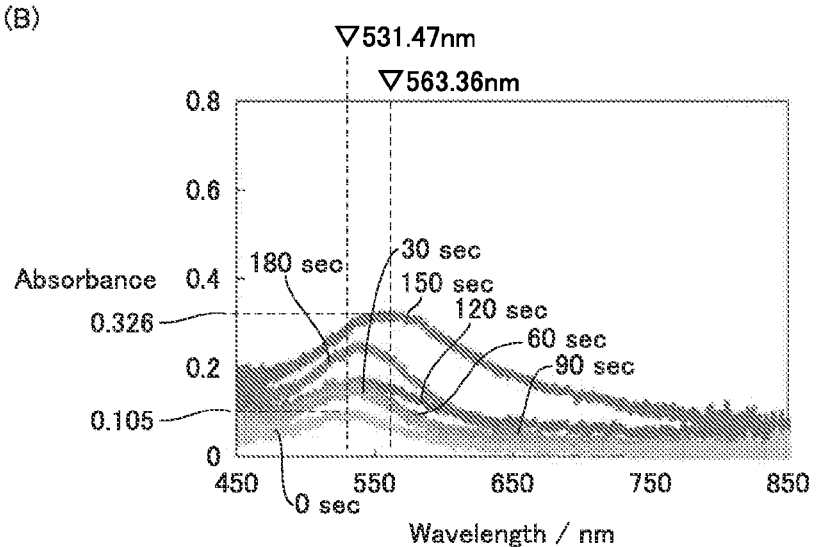

FIG.31
(A)
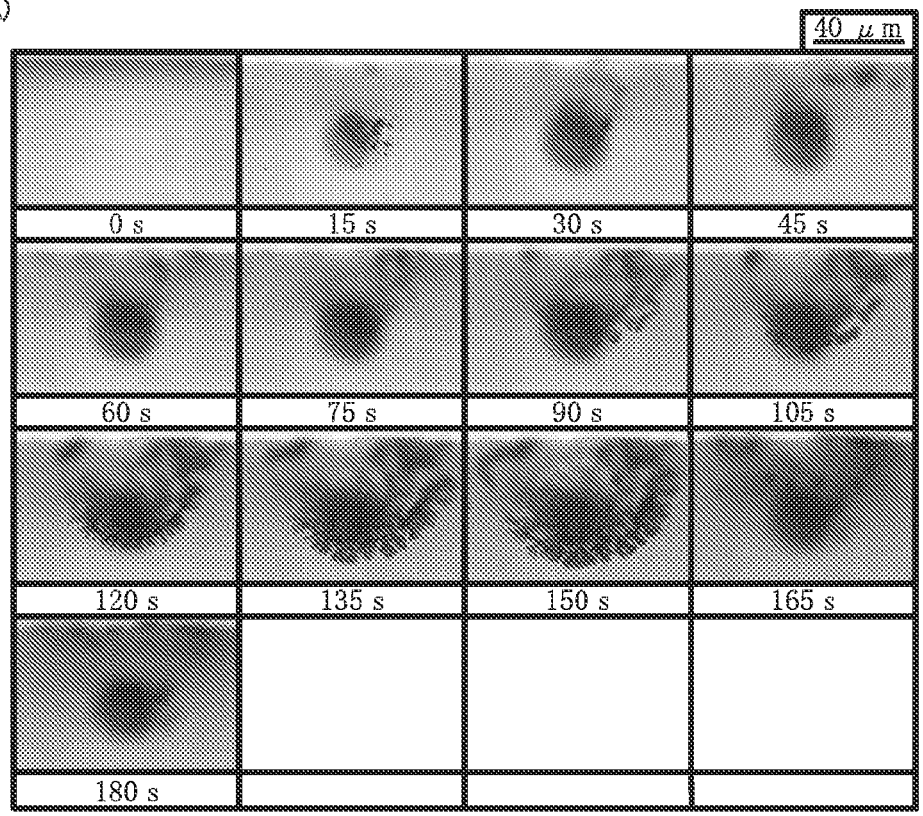
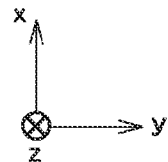
(B)
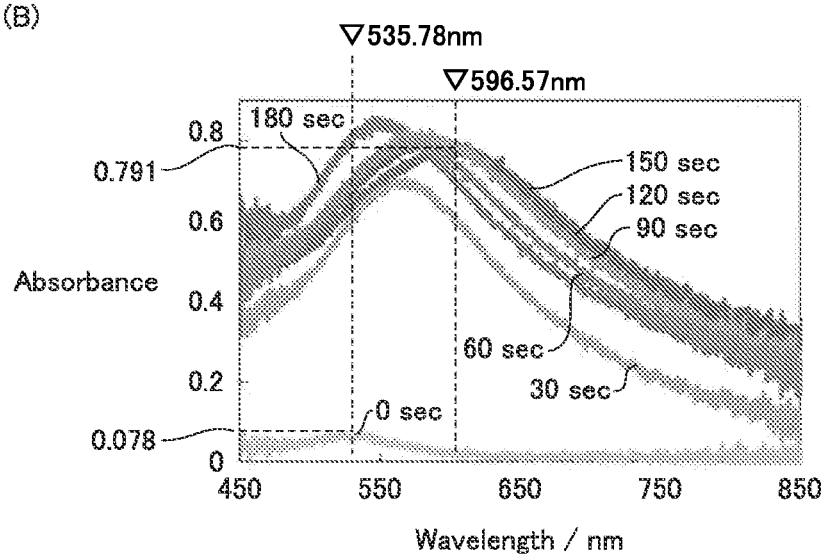

FIG.32
(A)
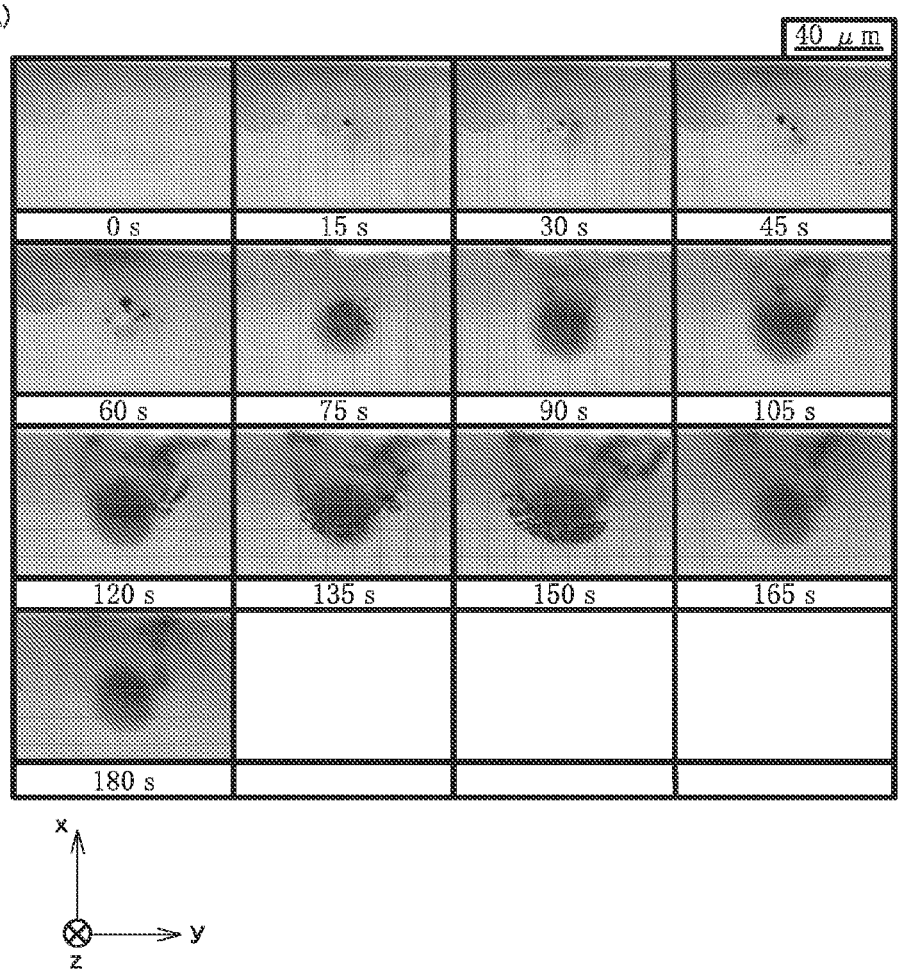
(B)
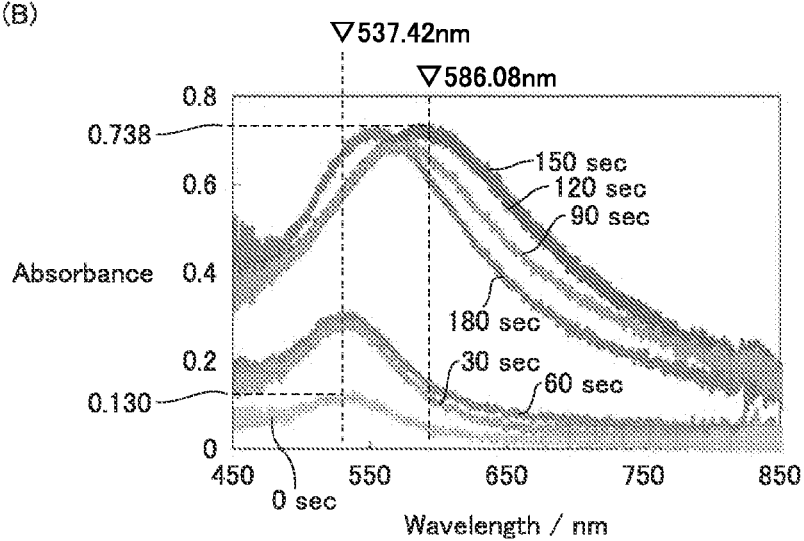

○:POSITION OF BEAM WAIST

DEVICE AND METHOD FOR DETECTING AN ANALYTE

REFERENCE TO SEQUENCE LISTING SUBMITTED VIA EFS-WEB

This application includes an electronically submitted sequence listing in .txt format. The .txt file contains a sequence listing entitled "2017-07-21 0033-1565PUS1 ST25.txt" created on Jul. 21, 2017 and is 1,608 bytes in size. The sequence listing contained in this .txt file is part of the specification and is hereby incorporated by reference herein in its entirety.

TECHNICAL FIELD

The present invention relates to a device and method for detecting an analyte.

BACKGROUND ART

In recent years, as an in-vitro diagnostic method, there has been proposed a diagnostic method utilizing presentation of color by localized surface plasmon resonance of colloidal gold. For example, in immunochromatography, there is proposed a method using colloidal gold having an antibody fixed thereto, as a tag-labeled particle. According to this method, when an antigen that is an analyte is contained in a specimen, the antigen and the tag-labeled particle are conjugated together to form a composite. The composite develops a moving bed and is captured by an antibody of a determination site. This causes the determination site to exhibit a red color. Whether the antigen is present or absent can be confirmed by confirming whether the determination site exhibits color.

For example, Japanese Patent Laying-Open No. 2009-210505 (PTD 1) discloses an immunological measurement kit aiming at application to immunochromatography. For example, Japanese National Patent Publication No. 2005-533246 (PTD 2) discloses a surface enhanced resonance Raman scattering (SERRS) active bead employed for identifying a target molecule. This bead includes aggregated metallic colloid and at least one SERRS active dye that are encapsulated in a polymer shell.

CITATION LIST

Patent Documents

PTD 1: Japanese Patent Laying-Open No. 2009-210505
PTD 2: Japanese National Patent Publication No. 2005-533246

SUMMARY OF INVENTION

Technical Problem

There constantly exists a need for a technique allowing an analyte to be detected with enhanced sensitivity, in other words, a technique allowing a trace amount of the analyte to be detected. According to the method disclosed in Japanese Patent Laying-Open No. 2009-210505 (PTD 1), whether a determination site exhibits color can be confirmed to conveniently confirm whether an antigen is present or absent. It is believed, however, that visually confirming whether color is exhibited requires that a specimen should contain an analyte of a concentration of some high extent, and requires the analyte in a large amount.

An object of the present invention is to provide a device and method allowing a trace amount of an analyte to be rapidly detected to contribute to overcoming the above issue.

Solution to Problem

The present invention in one aspect provides a detection device for detecting an analyte that may be contained in a specimen. The detection device comprises a plurality of metallic nanoparticles, a first light source, an objective lens, a photoreceiver, and a detector. The plurality of metallic nanoparticles are each modified with a host molecule allowing the analyte to specifically adhere thereto. The first light source emits polarized light for assembling the plurality of metallic nanoparticles together. The objective lens focuses and introduces the polarized light into a liquid containing a specimen and the plurality of metallic nanoparticles. The photoreceiver receives light from the liquid. The detector detects an analyte based on a signal received from the photoreceiver.

Preferably, the detection device further comprises an adjustment mechanism. The adjustment mechanism adjusts a distance between the objective lens and a gas-liquid interface of the liquid and a gas surrounding the liquid so that the objective lens has a focal point in the liquid in a vicinity of the gas-liquid interface.

Preferably, the detection device further comprises an optically transparent substrate holding the liquid.

Preferably, the plurality of metallic nanoparticles are each modified with a first host molecule. The detection device further comprises a substrate having a plurality of spots each having a second host molecule fixed thereto.

Preferably, the plurality of metallic nanoparticles include: a plurality of first metallic nanoparticles each modified with the first host molecule; and a plurality of second metallic nanoparticles each modified with the second host molecule.

Preferably, the analyte is a target DNA. The first and second host molecules are each a probe DNA hybridizing with the target DNA.

Preferably, the host molecule is a single type of host molecule.

Preferably, the analyte is an antigen. The host molecule is an antibody causing an antigen-antibody reaction with the antigen.

Preferably, the photoreceiver includes an image pick-up device for obtaining an image of the liquid. The detector detects the analyte based on the image obtained by the pickup device.

Preferably, the detection device further comprises a second light source emitting light for measuring the liquid's spectrum. The photoreceiver includes a spectroscope for measuring the liquid's spectrum. The detector detects the analyte based on a spectrum measured with the spectroscope.

Preferably, the second light source emits white light.

Preferably, the second light source emits substantially monochromatic light associated with one or more ranges corresponding to twice a full width at half maximum of a peak of localized surface plasmon resonance of the first metallic nanoparticle.

Preferably, the spectrum measured with the spectroscope is an adsorption spectrum of localized surface plasmon resonance.

Preferably, the spectrum measured with the spectroscope is a surface enhanced Raman scattering (SERS) spectrum.

Preferably, the target DNA is one of a first target DNA having a base sequence complementary to the probe DNA and a second target DNA having a base sequence partially different from the first target DNA. The photoreceiver includes a spectroscope for measuring a spectrum of the liquid. The detector determines whether the analyte is the first target DNA or the second target DNA, based on how the spectrum measured with the spectroscope varies with time.

Preferably, the first and second host molecules are first and second probe DNAs, respectively. The plurality of metallic nanoparticles are each modified with the first probe DNA. The detection device further comprises a substrate having a plurality of spots each having the second probe DNA fixed thereto. The analyte is one of a first target DNA having a base sequence complementary to the first and second probe DNAs and a second target DNA having a base sequence partially different from the first target DNA. The photoreceiver includes a spectroscope for measuring a spectrum of the liquid. The detector determines whether the analyte is the first target DNA or the second target DNA, based on how the spectrum measured with the spectroscope varies with time.

Preferably, the detection device further comprises a substrate having a micro channel passing the liquid. The light focused by the objective lens is introduced into the micro channel.

Preferably, a region of the substrate at least holding the liquid is super-hydrophilic.

Preferably, the plurality of metallic nanoparticles are dispersed in the liquid such that the plurality of metallic nanoparticles have a surface-to-surface distance larger than a sum of a size of the analyte and a size of the host molecule.

The present invention in another aspect provides a method for detecting an analyte that may be contained in a specimen. The method comprises the steps of: introducing into a liquid the specimen and a plurality of metallic nanoparticles each modified with a host molecule allowing the analyte to specifically adhere thereto; focusing via an objective lens polarized light output from a first light source, and irradiating the liquid with the polarized light focused, the polarized light being provided for assembling the plurality of metallic nanoparticles together; receiving light from the liquid by a photoreceiver; and detecting the analyte by a detector, based on the light received from the liquid.

Preferably, the analyte is an antigen. The host molecule is an antibody causing an antigen-antibody reaction with the antigen.

Preferably, the plurality of metallic nanoparticles are each modified with a first host molecule. The method further comprises the step of preparing a substrate having a plurality of spots each having a second host molecule fixed thereto. The step of introducing the specimen and the plurality of metallic nanoparticles into the liquid includes the step of introducing the specimen and the plurality of metallic nanoparticles into the liquid to be dropped on each of the plurality of spots.

Preferably, the plurality of metallic nanoparticles include: a plurality of first metallic nanoparticles each modified with a first host molecule; and a plurality of second metallic nanoparticles each modified with a second host molecule.

Preferably, the analyte is a target DNA. The first and second host molecules are each a probe DNA hybridizing with the target DNA.

Preferably, the step of receiving light includes the step of obtaining an image of the liquid by an image pick-up device. The step of detecting includes the step of detecting the analyte based on the image of the liquid.

Preferably, the method further comprises the step of irradiating the liquid with light output from a second light source for measuring a spectrum of the liquid. The step of receiving light includes the step of measuring the spectrum with a spectroscope. The step of detecting includes the step of detecting the analyte based on the spectrum.

Preferably, the step of irradiating includes the step of irradiating the liquid with substantially monochromatic light associated with one or more ranges corresponding to twice a full width at half maximum of a peak of localized surface plasmon resonance of the plurality of first metallic nanoparticles.

Preferably, the spectrum is an absorption spectrum of localized surface plasmon resonance.

Preferably, the spectrum is a surface enhanced Raman scattering (SERS) spectrum.

Preferably, the target DNA is one of a first target DNA having a base sequence complementary to the probe DNA and a second target DNA having a base sequence partially different from the first target DNA. The method further comprises the step of irradiating the liquid with light output from a second light source for measuring a spectrum of the liquid. The step of receiving light includes the step of measuring the spectrum with a spectroscope. The step of detecting includes the step of determining whether the analyte is the first target DNA or the second target DNA, based on how the spectrum varies with time.

Advantageous Effects of Invention

The present invention can thus provide a device and method allowing a trace amount of an analyte to be rapidly detected.

BRIEF DESCRIPTION OF DRAWINGS

FIG. 3 (SEQ ID NOS: 1, 2, and 3) is a conceptual diagram for illustrating how gold nanoparticles are aggregated by DNA hybridization.

FIG. 5 is an enlarged view of a configuration in a vicinity of a kit of the detection device shown in FIG. 4.

FIG. 6 is a schematic diagram for illustrating how gold nanoparticles aggregate in a vicinity of a beam waist of a laser light shown in FIG. 5.

FIG. 9 shows (A) an optical transmission image of a liquid mixture before light irradiation, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a complementary DNA (concentration: 10 nM, and volume: 5 µL), and (B) an optical transmission image of a liquid mixture before light irradiation, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a mismatched DNA (concentration: 1 µM, and volume: 5 µL).

FIG. 12 shows (A) an optical transmission image of a liquid mixture after light irradiation in a vicinity of a beam waist having a different position, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a complementary DNA (concentration: 10 nM, and volume: 5 µL), and (B) an optical transmission image of a liquid mixture after light irradiation in a vicinity of a beam waist having a different position, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a mismatched DNA (concentration: 1 µM, and volume: 5 µL).

FIG. 14 presents successive photographic images (or optical transmission images) of a gas-liquid interface (in a vicinity of a beam waist) showing how a diluted dispersion liquid of a mismatched DNA (concentration: 1 µM) after light irradiation starts varies with time.

FIG. 15 presents successive photographic images (or optical transmission images) of a gas-liquid interface (in a vicinity of a beam waist) showing how a diluted dispersion liquid of a complementary DNA (concentration: 10 nM) after light irradiation starts varies with time.

FIG. 17 presents successive photographic images (or optical transmission images) of a gas-liquid interface of a diluted dispersion liquid of a complementary DNA (concentration: 1 pM) (in a vicinity of a beam waist).

FIG. 27 (SEQ ID NOS: 1-6) is a diagram for illustrating a probe DNA and four types of DNAs that can serve as an analyte and have mutually different base sequences.

FIG. 29 shows (A) successive photographic images (or optical transmission images) of a gas-liquid interface of a liquid mixture (in a vicinity of a beam waist) after light irradiation starts, the liquid mixture being a liquid mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 μL), and a diluted dispersion liquid of a complementary DNA (concentration: 100 pM, and volume: 5 μL), and (B) how an absorption spectrum that the gas-liquid interface presents varies with time (0 second, 30 seconds, 60 seconds, 90 seconds, 120 seconds, 150 seconds, and 180 seconds after light irradiation starts).

FIG. 30 shows (A) successive photographic images (or optical transmission images) of a gas-liquid interface of a liquid mixture (in a vicinity of a beam waist) after light irradiation starts, the liquid mixture being a liquid mixture of a dispersion liquid of gold nanoparticles modified with the first probe DNA (concentration: 5.0 nM, and volume: 5 μL), a dispersion liquid of gold nanoparticles modified with the second probe DNA (concentration: 5.0 nM, and volume: 5 μL), and a diluted dispersion liquid of a completely mismatched DNA (concentration: 100 pM, and volume: 5 μL), and (B) how an absorption spectrum that the gas-liquid interface presents varies with time (0 second, 30 seconds, 60 seconds, 90 seconds, 120 seconds, 150 seconds, and 180 seconds after light irradiation starts).

FIG. 31 shows (A) successive photographic images (or optical transmission images) of a gas-liquid interface of a liquid mixture (in a vicinity of a beam waist) after light irradiation starts, the liquid mixture being a liquid mixture of a dispersion liquid of gold nanoparticles modified with the first probe DNA (concentration: 5.0 nM, and volume: 5 μL), a dispersion liquid of gold nanoparticles modified with the second probe DNA (concentration: 5.0 nM, and volume: 5 μL), and a diluted dispersion liquid of a half mismatched DNA (concentration: 100 pM, and volume: 5 μL), and (B) how an absorption spectrum that the gas-liquid interface presents varies with time (0 second, 30 seconds, 60 seconds, 90 seconds, 120 seconds, 150 seconds, and 180 seconds after light irradiation starts).

FIG. 32 shows (A) successive photographic images (or optical transmission images) of a gas-liquid interface of a liquid mixture (in a vicinity of a beam waist) after light irradiation starts, the liquid mixture being a liquid mixture of a dispersion liquid of gold nanoparticles modified with the first probe DNA (concentration: 5.0 nM, and volume: 5 μL), a dispersion liquid of gold nanoparticles modified with the second probe DNA (concentration: 5.0 nM, and volume: 5 μL), and a diluted dispersion liquid of an alternately mismatched DNA (concentration: 100 pM, and volume: 5 μL), and (B) how an absorption spectrum that the gas-liquid interface presents varies with time (0 second, 30 seconds, 60 seconds, 90 seconds, 120 seconds, 150 seconds, and 180 seconds after light irradiation starts).

DESCRIPTION OF EMBODIMENTS

Figure 1:
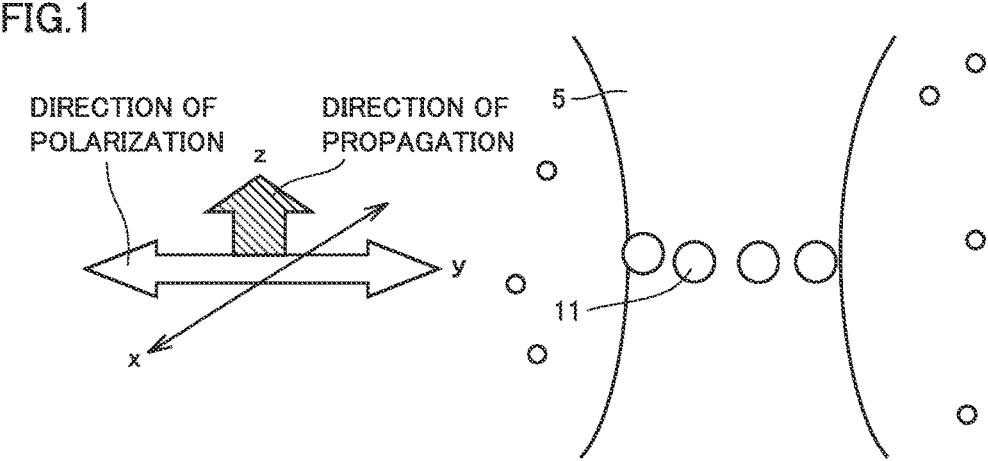
FIG. 1 is a schematic diagram for illustrating a mechanism of arranging a plurality of gold nanoparticles.

Hereinafter, an embodiment of the present invention will specifically be described with reference to the drawings. In the figures, identical or corresponding components are identically denoted and will not be described repeatedly.

In the present invention and its embodiment(s), a "metallic nanoparticle" is a metallic particle having a size on an order of nanometers. An "order of nanometers" includes a range of one to several hundreds nanometers and typically it ranges from 1 to 100 nm. The metallic nanoparticle is not limited in shape and may be a sphere or a rod as long as such metallic nanoparticles can be assembled by light irradiation.

In the present invention and its embodiment(s), a "metallic nanoparticle assembly" is an assembly formed by a plurality of aggregating metallic nanoparticles.

Furthermore in the present invention and its embodiment(s) an "analyte" may be a biomolecule and may be an organic molecule that is not limited to the biomolecule. Furthermore, the "analyte" may be a heavy metal ion.

In the present invention and its embodiment(s), a "host molecule" is a molecule allowing an analyte to specifically adhere thereto. Combinations of the host molecule allowing an analyte to specifically adhere thereto and the analyte include for example: antigen and antibody; sugar chain and protein; lipid and protein; a low molecule compound (ligand) and protein; protein and protein; single stranded DNA and single stranded DNA; and the like. When one component of such a specifically affinitive combination is an analyte, the other component of the combination can be used as a host molecule. In other words, if an antigen is an analyte, an antibody can be used as a host molecule. On the contrary, if an antibody is an analyte, an antigen can be used as a host molecule. Furthermore, in DNA hybridization, an analyte is a target DNA, and a host molecule is a probe DNA. Furthermore, an "antigen" can include allergen and virus. Furthermore, the present invention and its embodiment(s) also allow an antibody to be changed in type to change a type of allergen or virus detectable. The present invention and its embodiment(s) thus do not limit detectable allergen or virus in type. Furthermore, if the "analyte" is heavy metal, a molecule capable of capturing a heavy metal ion can be utilized as a host molecule.

In the present invention and its embodiment(s), a "first host molecule" and a "second host molecule" are host molecules that can specifically adhere to an analyte at different sites. For example, if a target DNA is an analyte, the first host molecule is a probe DNA hybridized from the 5' end of the target DNA. The second host molecule is a probe DNA hybridized from the 3' end of the target DNA.

For example, if an antigen is an analyte, the first host molecule is a primary antibody and the second host molecule is a secondary antibody. Note, however, that for example when an antigen is an analyte, a metallic nanoparticle having a surface modified with the primary antibody (or the first host molecule) may alone be used.

In the present invention and its embodiment(s), a "specimen" means a substance that may include a substance including an analyte or the analyte. The specimen may be biological specimens obtained for example from animals (e.g., human, cow, horse, pig, goat, chicken, rat, mouse, and the like). The biological specimen may include blood, tissues, cells, bodily secretions, bodily fluids, and the like, for example. Note that the "specimen" may also include their dilutions.

In the present invention and its embodiment(s) the term "white light" means continuous or pulsed light having a range in wavelength of a visible range-including, ultraviolet to near-infrared range (e.g., a range in wavelength of 200 nm to 1100 nm).

In the present invention and its embodiment(s) the term "monochromatic light" is light having a wavelength in a range corresponding to twice a full width at half maximum of a peak of localized surface plasmon resonance of a metallic nanoparticle assembly. The number of ranges corresponding to twice a full width at half maximum of a peak of localized surface plasmon resonance may be one or plural.

In the present invention and its embodiment(s) the term "polarization" means an electric field vector perpendicular to a direction in which an optical electromagnetic wave propagates.

In the present invention and its embodiment(s) the term "super-hydrophilicity" means that a tangent of a droplet held on a substrate and the substrate's surface form a contact angle of 10 degrees or smaller.

In the present invention and its embodiment(s) the term "dispersion" means that a host molecule or an analyte floats in a liquid, and the term includes a case in which the host molecule or the analyte is dissolved in the liquid. That is, a dispersion liquid can include a solution a dispersion medium can include a solvent.

First Embodiment

Arrangement of Gold Nanoparticles

In the following embodiment(s), a metallic nanoparticle is presented as a gold nanoparticle by way of example in form. The metallic nanoparticle is not limited to the gold nanoparticle, and may for example be a silver nanoparticle, a copper nanoparticle or the like.

The gold nanoparticle has an average diameter on a subnanometer order to a nanometer order (approximately 2 nm to 1000 nm), and it can for example be 2 nm to 500 nm, preferably 2 nm to 100 nm, more preferably 5 nm to 50 nm.

As will be described more specifically hereafter, a plurality of gold nanoparticles are captured by light-induced force and also arranged. In the present invention and its embodiment(s) "light-induced force" is used to correctively represent dissipative force, gradient force, and inter-object light-induced force. Dissipative force is a force generated in a dissipative process such as light scattering or light absorption as a momentum of light is imparted to a substance. Gradient force is a force moving an object with light-induced polarization to a stable point of an electromagnetic potential when the object is located in a nonuniform electromagnetic field. Inter-object light-induced force is a sum of a force attributed to a longitudinal electric field and a force attributed to a transverse electric field (or radiation field) that are generated from induced polarization caused in optically-excited plural objects.

Figure 2:
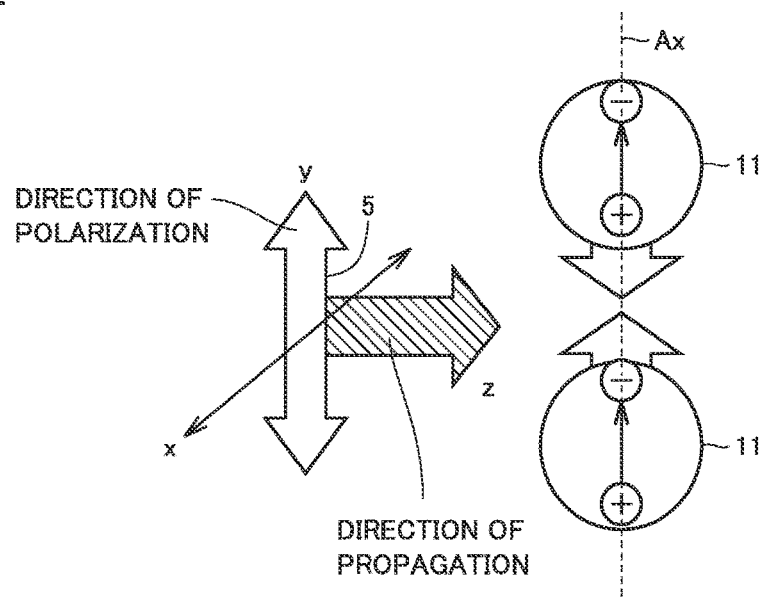
FIG. 2 is a figure for illustrating a 2-particle model of gold nanoparticles.

FIG. 1 is a schematic diagram for illustrating a mechanism of capturing and arranging a plurality of gold nanoparticles. FIG. 2 is a figure for illustrating a 2-particle model of gold nanoparticles. With reference to FIG. 1 and FIG. 2, the plurality of gold nanoparticles 11 are dispersed in a liquid, e.g., in water.

Each of the plurality of gold nanoparticles 11 receives laser light 5. Laser light 5 has a direction of polarization in the y-direction. In other words, laser light 5 is polarized in a direction substantially parallel to axis Ax passing through gold nanoparticles 11 through their respective centers. In that case, gold nanoparticles 11 are each electrically polarized in a direction parallel to the direction of polarization of laser light 5. Thus, each gold nanoparticle 11 is captured at a vicinity of a stable point in electromagnetic potential of laser light 5, i.e., in a vicinity of a beam waist of laser light 5. Furthermore, gold nanoparticles 11 all have electric polarization in the same direction. This causes attractive force between adjacent gold nanoparticles 11, as shown in FIG. 2.

It is assumed that the metallic nanoparticle is a spherical cell. In that case a response optical electric field can be described with an integral form of a Maxwell equation. A response electric field $E_i$ is represented according to the following equation (1):

$$E_i = E_i^0 + \sum_{j=1, j \neq i}^{N_p} G_{r,r',\omega}(i-j) \cdot P_j V_j + M_i \cdot P_i - \frac{L \cdot P_i}{k^2}, \quad (1)$$

where i and j represent particle numbers of spherical cells, and M and L represent amounts associated with self-interaction. Susceptibility and electric field distributions in individual gold nanoparticles are assumed to be flat. An induced polarization $P_i$ is represented according to the following equation (2):

$$P_i = \chi_i(\omega) E_i \quad (2).$$

Note that a Drude model is applied to susceptibility $\chi$. Susceptibility $\chi$ is represented according to the following equation (3):

$$\chi = \chi_b - \frac{\omega_p^2}{\omega^2 + i\omega(\gamma + V_f/a)}, \quad (3)$$

where $\chi_b$ represents background susceptibility, $\omega_p$ represents plasma energy, $\gamma$ represents a nonradiative relaxation constant, and $V_f$ represents electron velocity on the Fermi surface. Nonradiative relaxation constant $\gamma$ is a value indicative of relaxation from light to other than light (e.g., heat).

In contrast, light-induced force is generally represented by the following equation (4) (T. Iida and H. Ishihara, Phys. Rev. B77, 245319 (2008)):

$$\langle F \rangle = \frac{1}{2} \text{Re} \left\{ \sum_{\omega} \int_V dr [\nabla E(r, \omega)^*] \cdot P(r, \omega) \right\}. \quad (4)$$

Induced polarization $P_i$ and response electric field $E_i$ represented by equation (2) and equation (3), respectively, are substituted in equation (4). Thus, the light-induced force is represented by the following equation (5):

$$\langle F_i \rangle = \frac{1}{2}\text{Re}\{[\nabla E^{(0)}(r_i, \omega)^*] \cdot P(r_i, \omega) \cdot V\} + \frac{1}{2}\text{Re}\{[\nabla_{ij} G(r_i)^* \cdot P_j^* \cdot V] \cdot P_i \cdot V\}. \tag{5}$$

G represents Green's function. In equation (5) at the right hand side the first term represents a gradient force attributed to incident light and the second term represents inter-object light-induced force. Gradient force attributed to incident light is proportional to light intensity gradient. In contrast, inter-object light-induced force is proportional to light intensity. Thus, light intensity gradient and light intensity of incident light can be controlled to adjust gradient force and inter-object light-induced force.

Again, with reference to FIG. 1, gold nanoparticles 11 dispersed in water each have a surface covered with a protecting group added when gold nanoparticles 11 are produced, and as the protecting group is ionized, the surface has a surface charge. The surface of each gold nanoparticle 11 has a single type of electric charge distributed thereon. This causes repulsive force between a plurality of gold nanoparticles 11. When the trapping force caused via the radiation of the laser light (i.e., dissipative force and gradient force), the attractive force caused between the gold nanoparticles via electric polarization (i.e., inter-object light-induced force), and the repulsive force caused via the surface charge are in balance, the plurality of gold nanoparticles 11 can be arranged in a direction parallel to that in which laser light 5 is polarized.

<Formation of Gold Nanoparticle Assembly>

The gold nanoparticles are each modified with a host molecule. The host molecule has a site that can interact with a gold nanoparticle. The host molecule is fixed to a surface of the gold nanoparticle via the above site. The "interaction" refers to chemical bonding, Van der Waals force, electrostatic interaction, hydrophobic interaction, adsorption power, and the like. A site (or group) that can interact with gold is, but not limited to, a thiol group, for example.

In the present embodiment the analyte is a target DNA. In the presence of the target DNA, gold nanoparticles modified with a probe DNA are aggregated by DNA hybridization and form a gold nanoparticle assembly. In contrast, probe DNAs do not hybridize with each other. "Hybridization" means a reassociation reaction between two types of single stranded nucleic acids. In the present embodiment, a double strand is formed between two single strands of DNA that have complementary base sequences, as will be described hereinafter. However, hybridization is not limited thereto and includes formation of a double strand between one single strand of DNA and one RNA or between two RNAs.

FIG. 3 is a conceptual diagram for illustrating how gold nanoparticles are aggregated by DNA hybridization. FIG. 3(A) is a diagram showing one example of a base sequence of a probe DNA. FIG. 3(B) is a schematic diagram showing states before and after gold nanoparticles aggregate.

With reference to FIG. 3(A), the present embodiment employs a target DNA 18 as an analyte. Target DNA 18 is a single strand of DNA having a base sequence of 24 adenines for example. Probe DNAs 13 and 14 allowing target DNA 18 to specifically adhere thereto, are prepared.

Probe DNA 13 is a single strand of DNA having a 3' end for example with a thiol group (represented as "SH"). Probe DNA 13 has between the thiol group and a 5' end thereof a base sequence complementary to a base sequence of the target DNA closer to a 3' end thereof. In the present embodiment the complementary base sequence is 12 thymines (represented as "T").

Probe DNA 14 is a single strand of DNA having a 5' end for example with a thiol group. Probe DNA 14 has between a 3' end thereof and the thiol group a base sequence complementary to a base sequence of the target DNA closer to a 5' end thereof. In the present embodiment the complementary base sequence is 12 thymines.

Then, with reference to FIG. 3(B), in the present embodiment, some gold nanoparticles 11 each have a surface modified with probe DNA 13 via the thiol group. The remaining gold nanoparticles 12 each have a surface modified with probe DNA 14 via the thiol group. A gold nanoparticle can be modified with a probe DNA for example in the following method:

Initially, 3.61 μM of thiolated DNA is added to a liquid having gold nanoparticles dispersed therein, and the liquid is then allowed to stand for example for 16 hours. Subsequently, sodium chloride and a phosphate buffer (pH: 7.0) are added to the above dispersion liquid to be 0.1 M and 10 mM and the liquid is then allowed to stand for example for 40 hours. Centrifugation is performed to settle nanoparticles and cleaning is performed. Note that the gold nanoparticle dispersion liquid may be a commercially available product or may be produced by using a gold ion (or gold complex ion) containing dispersion liquid and a reducing agent and thereby conducting a reductive reaction in the dispersion liquid. For example, a chlorauric acid dispersion liquid with citric acid added thereto may be used.

When gold nanoparticles 11 and 12 are introduced into a liquid containing target DNA 18, probe DNA 13 and target DNA 18 hybridize together and so do probe DNA 14 and target DNA 18. This causes gold nanoparticles 11, 12 to aggregate and thus form a gold nanoparticle assembly 10.

<Detection Device and Method>

Figure 4:
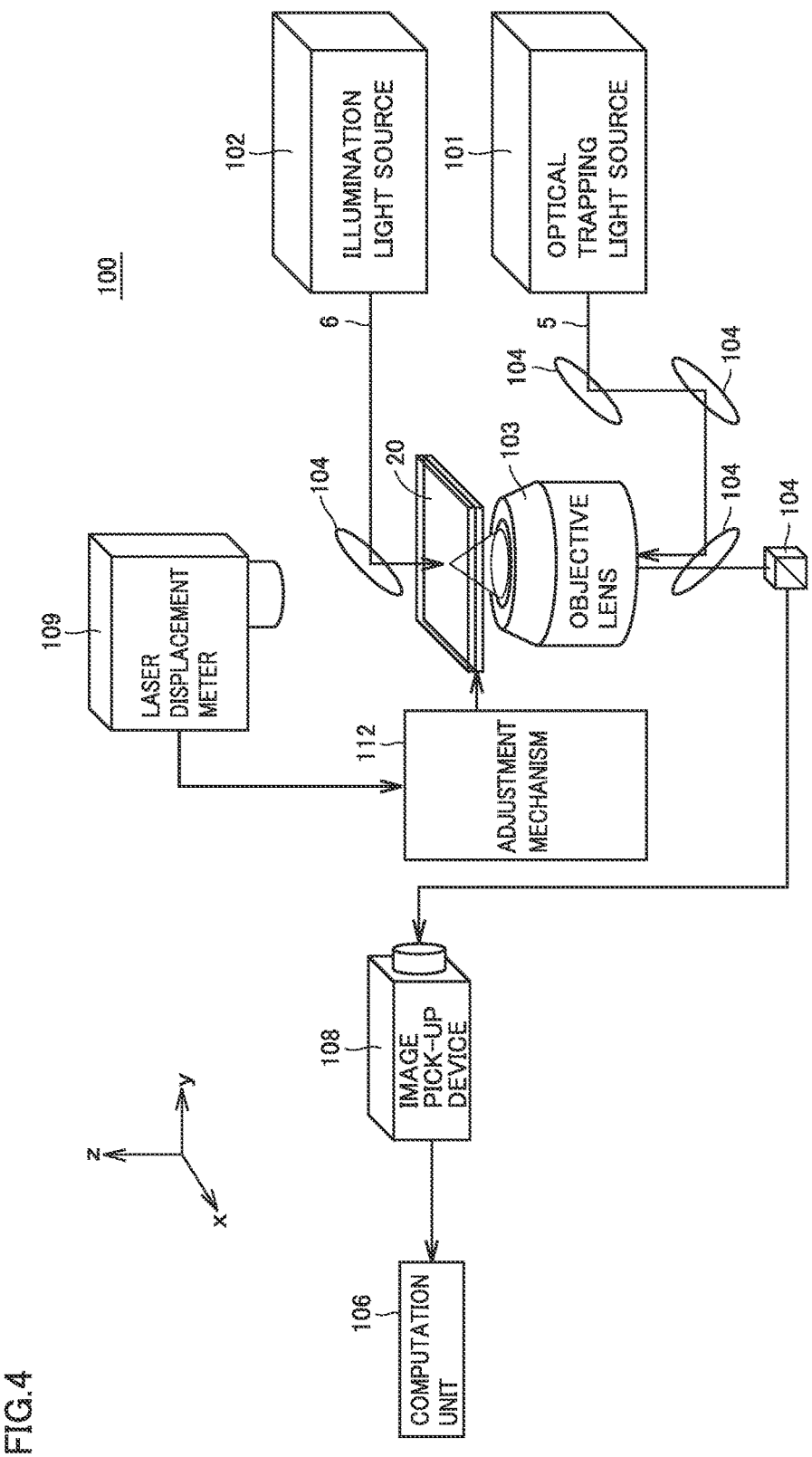
FIG. 4 schematically shows a configuration of a detection device according to a first embodiment of the present invention.

FIG. 4 schematically shows a configuration of a detection device according to the first embodiment of the present invention. With reference to FIG. 4, a detection device 100 includes an optical trapping light source 101 (a first light source), an illumination light source 102, an optical component 104, an objective lens 103, a kit 20, an image pick-up device 108 (a photoreceiver), a computation unit 106 (a detector), and an adjustment mechanism 112. The x direction and the y direction each represent a horizontal direction. The x direction and the y direction are orthogonal to each other. The z direction represents a vertical direction. Gravity has a direction in the z direction downward.

Optical trapping light source 101 emits laser light 5 as polarized light for assembling gold nanoparticles 11 and 12. Laser light 5 in kit 20 has a direction of polarization in the y-direction. Laser light 5 is radiated in the z direction upward to irradiate kit 20 (see FIG. 5).

Optical trapping light source 101 is not specifically limited in configuration and may be any known light source used to operate nano-objects. Optical trapping light source 101 generates continuous near-infrared light (e.g., a wavelength of 1064 nm). Note that the polarization is not limited in type to linear polarization, and it may for example be circular polarization or elliptical polarization, and furthermore, it may be axially symmetric polarization. Axially symmetric polarization includes radial polarization and azimuthal polarization.

Illumination light source 102 emits light for illuminating a sample 30 (see FIG. 5) within kit 20. Illumination light source 102 is a light source emitting white light 6 for example. As one embodiment, a halogen lamp can be used as illumination light source 102. Note that illumination light source 102 may be implemented as a monochromatic light source such as a laser light source. Note, however, that using a white light source as illumination light source 102 allows detection device 100 to be implemented at a low cost.

Optical component 104 includes a mirror, a prism, an optical fiber and/or the like for example. Optical component 104 is used to guide laser light 5 and white light 6 from optical trapping light source 101 and illumination light source 102, respectively, to kit 20.

Objective lens 103 receives laser light 5 from optical trapping light source 101 and focuses laser light 5 received. The light focused by objective lens 103 is radiated to irradiate sample 30. Sample 30 is a liquid for example having introduced therein target DNA 18 and gold nanoparticles 11 and 12 having surfaces modified with probe DNAs 13 and 14, respectively. Note that in the present embodiment laser light 5 having passed through objective lens 103 has an intensity for example of about 10% of that of laser light 5 output from optical trapping light source 101. Note that objective lens 103 and optical component 104 are for example incorporated in the body of a microscope (not shown).

Furthermore, objective lens 103 is also used in order to collect light received from sample 30. To efficiently collect light received from sample 30, objective lens 103 preferably has a high numerical aperture (NA). Note that kit 20 may be irradiated with white light 6 output from illumination light source 102 via objective lens 103.

Image pick-up device 108 obtains an image of a vicinity of a beam waist of laser light 5. Image pick-up device 108 receives white light 6 radiated from illumination light source 102 to irradiate the liquid and having passed through the liquid, and accordingly, image pick-up device 108 corresponds to a "photoreceiver" according to the present invention. Image pick-up device 108 is implemented for example as a video camera equipped with a charge coupled device (CCD) image sensor. Note that image pick-up device 108 may pick up a moving image or a static image.

The FIG. 4 configuration provides objective lens 103 positionally fixed. Adjustment mechanism 112 adjusts an xyz-axis stage 114 (see FIG. 5) positionally in the x, y and z directions with kit 20 mounted thereon. Adjustment mechanism 112 can be implemented for example as a focusing handle attached to a microscope. The position of kit 20 relative to objective lens 103 is thus adjusted. Note that adjustment mechanism 112 is not limited to any particular configuration. Furthermore, adjustment mechanism 112 may adjust the position of objective lens 103 relative to kit 20 fixed.

A laser displacement meter 109 can be used to adjust the position of the beam waist of laser light 5. Furthermore, laser displacement meter 109 can also be used in measuring the dispersion liquid of sample 30 in thickness and determining the position of the gas-liquid interface. Laser displacement meter 109 for example measures a vertical distance between laser displacement meter 109 and kit 20 and also measures horizontal displacement of kit 20. Adjustment mechanism 112 may refer to a resultant measurement that is provided by laser displacement meter 109 to adjust the position of the xyz-axis stage. Note that laser displacement meter 109 is not an essential component.

Computation unit 106 is implemented as a microcomputer or a personal computer or the like, for example. Computation unit 106 receives a signal from image pick-up device 108 (e.g., a signal indicating a moving image obtained through image pick-up device 108). Computation unit 106 detects target DNA 18 based on the signal received from image pick-up device 108.

FIG. 5 is an enlarged view of a configuration in a vicinity of kit 20 of detection device 100 shown in FIG. 4. FIG. 5(A) is a diagram showing a configuration of a vicinity of a kit 20. FIG. 5(B) is a diagram showing an optical system of objective lens 103 more specifically. With reference to FIG. 5(A), kit 20 includes a substrate 21. Kit 20 may include a liquid level guide 24 provided on substrate 21.

Substrate 21 receives sample 30 dropped thereon having a specimen and gold nanoparticles 11, 12 introduced therein. Substrate 21 can be made of a material transparent to white light. Preferably, substrate 21 is for example made of glass, quartz or a similar material that does not present anisotropy to polarized light.

Liquid level guide 24 indicates where sample 30 should be dropped. Liquid level guide 24 is determined in geometry, as appropriate, depending on the volume of sample 30 dropped, the level of the gas-liquid interface to be formed, as measured from substrate 21 (i.e., a distance in the z direction from the substrate to the gas-liquid interface), and the like. Liquid level guide 24 can be made for example of a water-repellent material such as polymer film. Kit 20 may for example be a commercially available glass bottomed dish. Thus, kit 20 is not limited to the configuration shown in FIG. 5(A).

In this embodiment, the distance between objective lens 103 and sample 30 is determined so that laser light 5 has a beam waist in the liquid. Laser light 5 has the beam waist formed at the position of a focal point of objective lens 103. That is, objective lens 103 and sample 30 have their relative positions adjusted so that objective lens 103 has its focal point positioned in the liquid.

D2 represents a distance between an upper surface 21a of substrate 21 and the focal point of objective lens 103. Distance D2 is adjusted to position the focal point of objective lens 103 in the liquid. Distance D2 can be adjusted from a focal length F of objective lens 103, a thickness T of substrate 21, and a distance D1 between a major surface 103a of objective lens 103 and an upper surface 114a of xyz-axis stage 114 (or a lower surface 21b of substrate 21), for example as follows:

Focal length F is known from a value of a specification of objective lens 103. Furthermore, thickness T of substrate 21 is known from a value of a specification of substrate 21 (e.g., a glass bottomed dish).

Adjustment mechanism 112 includes a control unit (not shown), which has a function to move xyz-axis stage 114 to a prescribed reference position for example in response to an initialization operation done by the user. When xyz-axis stage 114 is in the reference position, distance D1 has a reference value previously stored by the control unit. When the control unit operates in response to the user's operation to adjust the position of xyz-axis stage 114 in the z direction, it calculates distance D1, as adjusted, from a displacement of xyz-axis stage 114 from the reference position of xyz-axis stage 114 in the z direction.

Objective lens 103 has focal length F equal to the sum of distance D1, thickness T of substrate 21, and distance D2 ($F=D1+T+D2$). Distance D2 is represented as $D2=F-D1-T$, in other words. As has been set forth above, focal length F and thickness T of substrate 21 have known values. Furthermore, distance D1 is calculated by the control unit of adjustment mechanism 112. The adjustment mechanism 112 control unit can thus calculate distance D2.

With reference to FIG. 5(B), how distance D2 is calculated will more specifically be described by indicating a specific example. Objective lens 103 can for example be Nikon CFI Plan Fluor 100XH oil (observation magnification: 100×, working distance: 0.16 mm, and focal length: 2 mm)

When objective lens 103 and substrate 21 have an upper surface 103$b$ and lower surface 21$b$, respectively, with a distance therebetween set to 160 µm, objective lens 103 has a focal point matched to the substrate 21 upper surface 21$a$. This distance is referred to as a working distance (WD). Immersion oil 115 is introduced to fill a gap between upper surface 103$b$ of objective lens 103 and lower surface 21$b$ of substrate 21.

Objective lens 103 is movable from this state along the z axis to a position immediately before it has upper surface 103$b$ in contact with lower surface 21$b$ of substrate 21. That is, objective lens 103 can move a distance of 160 µm or smaller in the z direction. Accordingly, objective lens 103 has a focal point in the z direction in a range (i.e., distance D2 has a range) of 0 mm to 160 µm as measured from upper surface 21$a$ of substrate 21. Note that sample 30 has an index of refraction different from that of air (an index of refraction of 1.33 for a dispersion medium of water or phosphate buffer), and accordingly, it is desirable to adjust focus while considering the index of refraction of sample 30.

Furthermore, the observation system's magnification is calculated from a value of a specification of a focal length of an imaging lens (not shown) incorporated into the body of a microscope (not shown), as follows: magnification=the imaging lens's focal length/the objective lens's focal length=200 mm/2 mm=100 times.

When distance D3 from gas-liquid interface 31 to upper surface 21$a$ of substrate 21 has larger values, the observation system's focus position is more offset from the position of the focal point of objective lens 103. A focused image can be obtained by setting objective lens 103 to have a focal point positioned in the horizontal direction (or the y direction) for example at an end of gas-liquid interface 31, i.e., at gas-liquid interface 31 in a vicinity of liquid level guide 24. As an example, when sample 30 has a volume of 15 µL, objective lens 103 desirably has a focal point in the horizontal direction at a position for example of 50 µm or smaller in the y direction with reference to liquid level guide 24.

Furthermore, it is preferable that distance D2 is set for example to 20 µm or smaller. Focal length F is for example 2 mm and thickness T is for example 0.17 mm. Accordingly, when distance D1 has a reference value D1α and distance D1 is displaced from reference value D1α by an amount of D1β, then, distance D2=F−T−(D1α+D1β)=2,000−170−(D1α+D1β). In other words, distance D2 of 20 µm or smaller can be provided by setting D1=(D1α+D1β) to be 1810 µm or larger.

Note that in the configuration shown in FIG. 4 and FIG. 5, sample 30 is dropped on substrate 21 placed in a horizontal plane (i.e., the xy plane). Furthermore, objective lens 103 is arranged vertically under substrate 21 (or in the z direction thereunder). However, the surface in which the substrate is placed is not limited to a precisely horizontal plane, and may have inclination relative to the horizontal plane. Furthermore, the objective lens may be arranged vertically over or under the substrate. For example, the objective lens may be arranged vertically over the substrate that is placed in a horizontal plane. Thus, the laser light is radiated vertically downward (i.e., from the same side as the gas-liquid interface with respect to the substrate).

FIG. 6 is a schematic diagram for illustrating how gold nanoparticles 11, 12 aggregate in a vicinity of a beam waist of laser light 5 shown in FIG. 5. FIG. 6(A) shows gold nanoparticles 11 and 12 before they aggregate. FIG. 6(B) shows gold nanoparticles 11 and 12 after they aggregate.

With reference to FIG. 6(A), when the gas-liquid interface is irradiated with laser light 5, gold nanoparticles 11 and 12 gather at the gas-liquid interface. This allows gold nanoparticles 11 and 12 to have an increased density locally larger in a vicinity of the beam waist than at the other locations. The beam waist has a beam diameter for example of approximately several µm.

Then, with reference to FIG. 6(B), when target DNA 18 is present around gold nanoparticles 11 and 12, probe DNA 13 and target DNA 18 hybridize together and so do probe DNA 14 and target DNA 18. Target DNA 18 has a length for example on an order of nanometers (e.g., from several nanometers to several tens nanometers). Note that, as has been set forth above, laser light 5 has a wavelength for example of 1064 nm. Accordingly, gold nanoparticles 11, 12 have therebetween a distance fixed on a scale equal to or smaller than the wavelength of laser light 5 and equal to or smaller than visible light's wavelength.

Probe DNAs 13, 14 present on the surfaces of gold nanoparticles 11, 12 having a fixed interparticle distance further hybridize with other neighboring target DNA 18. DNA hybridization increases the assembly of gold nanoparticles 11, 12 in size, which in turn provides an increased probability of target DNA 18 being present in a vicinity of the assembly and hence further helps DNA hybridization to arise. The assembly of gold nanoparticles 11, 12 increased in size thus allows DNA hybridization to arise more frequently. In other words, the present embodiment allows light irradiation to accelerate forming a gold nanoparticle assembly. As a result, a gold nanoparticle assembly of gold nanoparticles 11, 12 densely aggregated together is formed in a short period of time.

Figure 7:
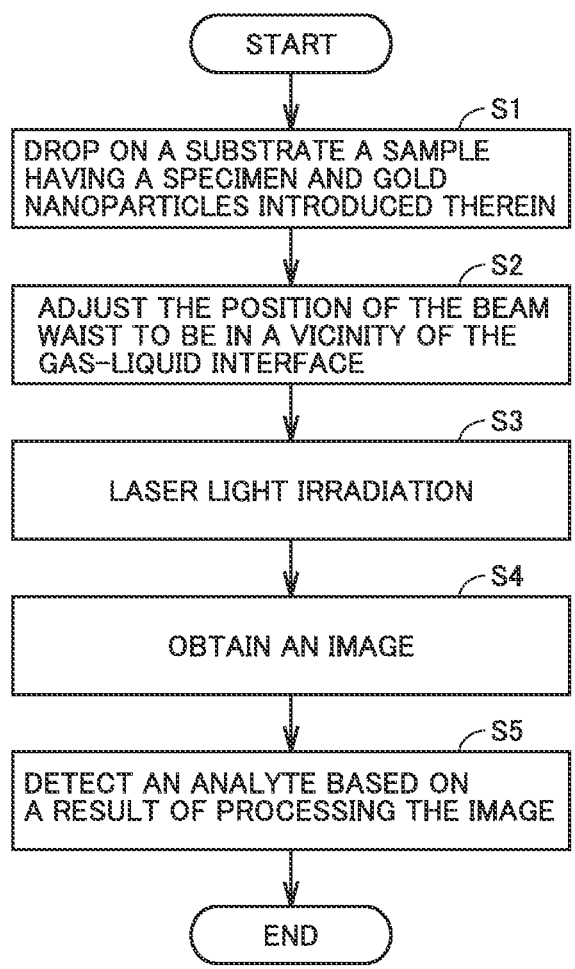
FIG. 7 is a flowchart for illustrating a method for detecting an analyte according to the first embodiment of the present invention.
Figure 8:
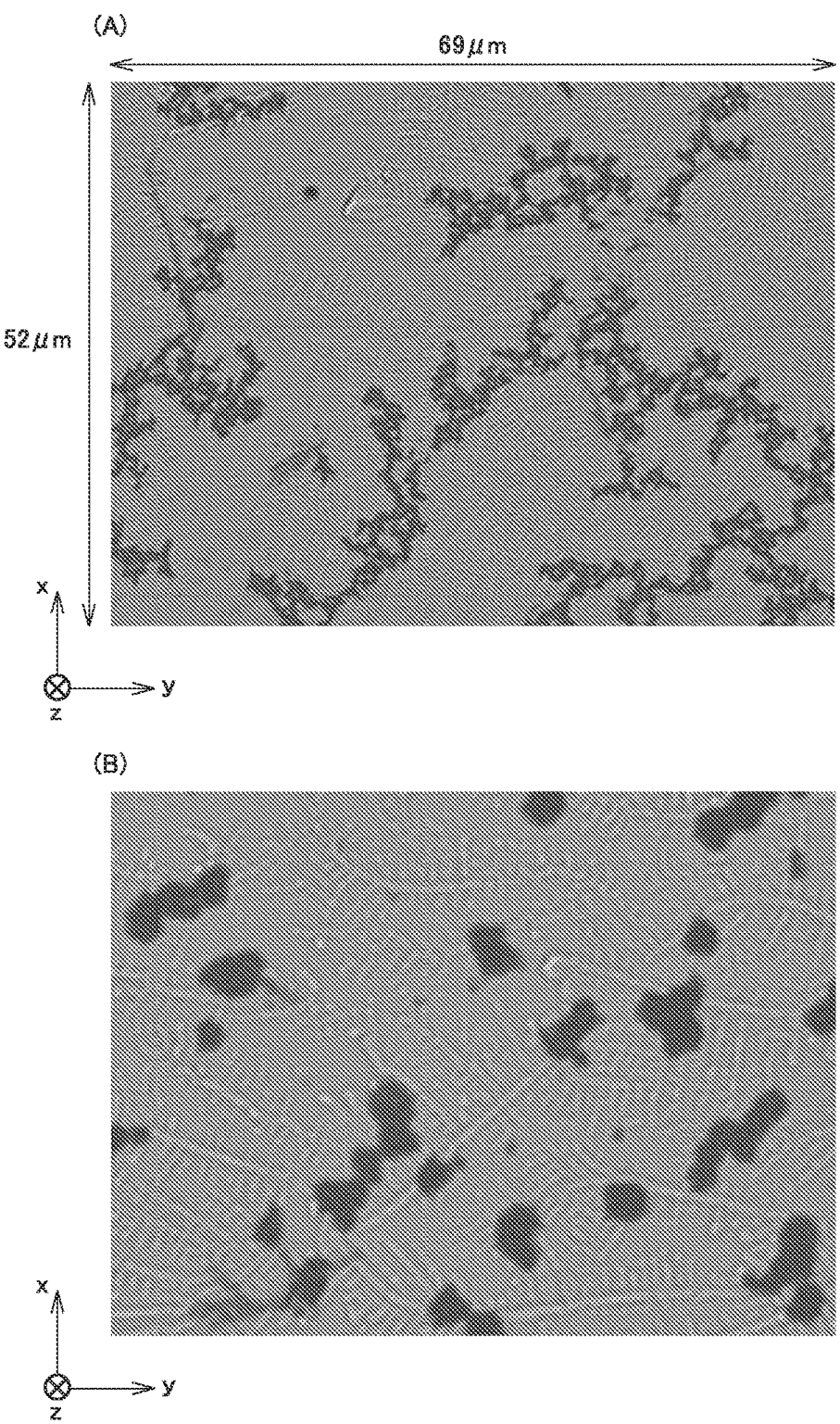
FIG. 8 shows (A) an optical transmission image of a sample of a liquid mixture naturally dried on a substrate without undergoing light irradiation, the liquid mixture being a mixture of a dispersion liquid of gold nanoparticles modified with a first probe DNA (concentration: 5.0 nM, and volume: 5 μL), a dispersion liquid of gold nanoparticles modified with a second probe DNA (concentration: 5.0 nM, and volume: 5 μL), and a diluted dispersion liquid of a complementary DNA (concentration: 10 nM, and volume: 5 μL), and (B) an optical transmission image of a sample of a liquid mixture naturally dried on a substrate without undergoing light irradiation, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a mismatched DNA (concentration: 1 µM, and volume: 5 µL).
Figure 10:
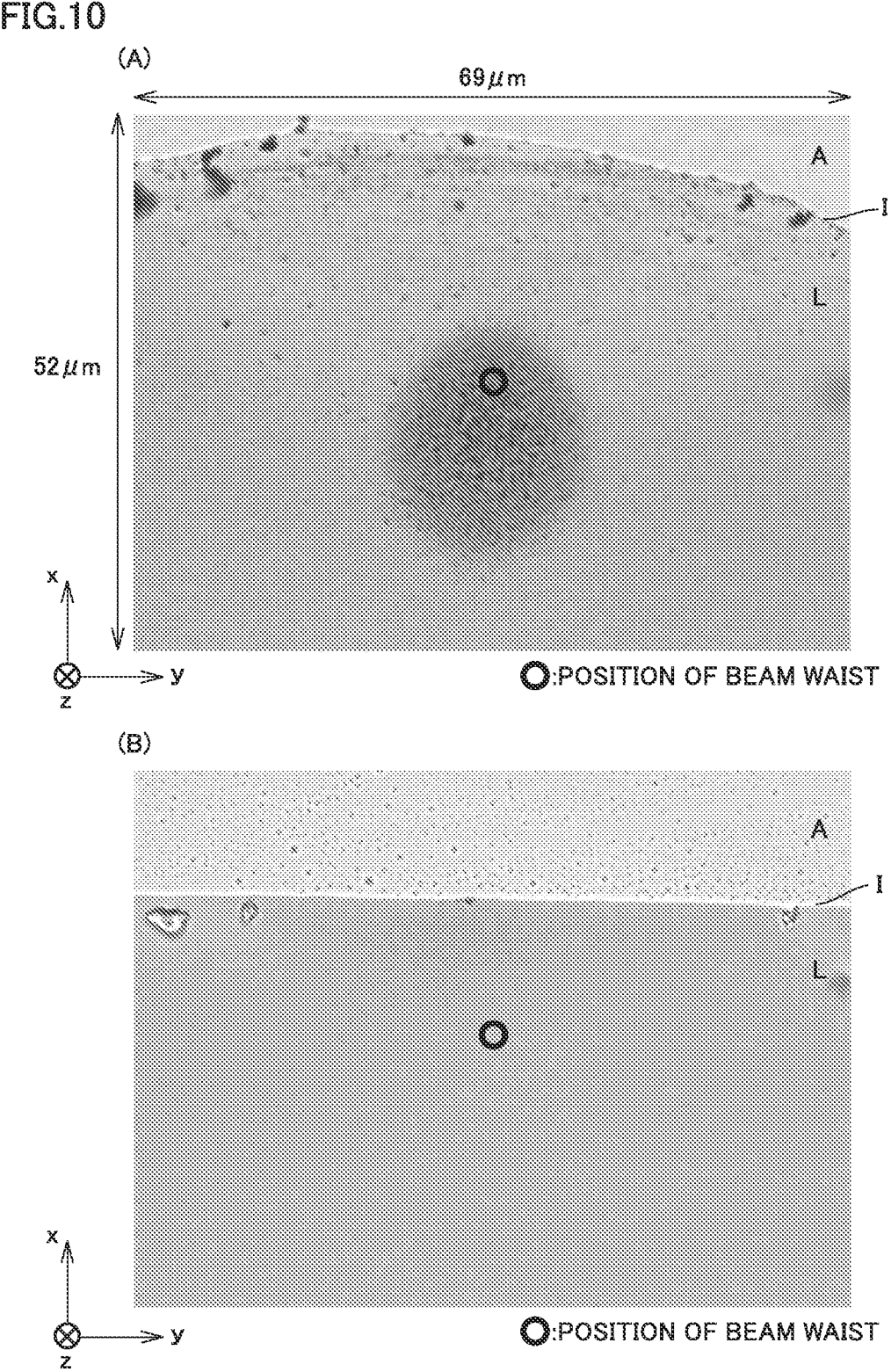
FIG. 10 shows (A) an optical transmission image of a liquid mixture after light irradiation, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a complementary DNA (concentration: 10 nM, and volume: 5 µL), and (B) an optical transmission image of a liquid mixture after light irradiation, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a mismatched DNA (concentration: 1 µM, and volume: 5 µL).

FIG. 7 is a flowchart for illustrating a method for detecting target DNA 18 according to the first embodiment of the present invention. With reference to FIG. 4, FIG. 5 and FIG. 7, in step S1, gold nanoparticles 11 and 12 modified with probe DNAs 13 and 14, respectively, are introduced into sample 30 containing a specimen.

In step S2, adjustment mechanism 112 adjusts the position of sample 30 relative to the focal point of objective lens 103. As has been set forth above, objective lens 103 preferably has a focal point in the liquid in a vicinity of gas-liquid interface 31. As in this embodiment, when sample 30 has a minute volume (for example on the order of microliters), objective lens 103 has a focal point adjusted to have a position closer to gas-liquid interface 31 than a midpoint M between the upper surface of substrate 21 and gas-liquid interface 31 on an optical axis L of laser light 5. The distance between the focal point of objective lens 103 and gas-liquid interface 31 can be adjusted for example as follows.

The control unit of adjustment mechanism 112 obtains an image of a droplet of sample 30 with a camera (not shown), and obtains from the image a level D3 of gas-liquid interface 31 as measured from substrate 21. The region surrounded by liquid level guide 24 has a fixed area, and accordingly, there is a correlation between the volume (or amount dropped) of sample 30 and level D3 of gas-liquid interface 31. The control unit stores this correlation previously for example as a table. Level D3 of gas-liquid interface 31 can be obtained from this table and an amount of sample 30 actually dropped. Alternatively, the control unit may obtain an image of sample 30 for each measurement and obtain level D3 of gas-liquid interface 31 therefrom.

As has been described with reference to FIG. 5, distance D2 from upper surface 21a of substrate 21 to the focal point can be obtained based on focal length F of objective lens 103, thickness T of substrate 21, and distance D1 between major surface 103a of objective lens 103 and lower surface 21b of substrate 21. Accordingly, level D3 of gas-liquid interface 31 obtained as described above allows distance D4 between gas-liquid interface 31 and the focal point to be calculated.

Note that when the region surrounded by liquid level guide 24 is for example a circle of a radius R, it is not necessary to obtain an image of sample 30. In that case, sample 30 dropped can be geometrically approximated to a semi-spheroid. Accordingly, when sample 30 has a volume V and a maximum height H (i.e., a distance at the center of the above region between the upper surface of substrate 21 and gas-liquid interface 31 along the optical axis of laser light 5), a relationship of $V=2\pi R^2 H/3$ is established. That is, maximum height H is equal to $(3/2) \times V/(\pi R^2)$. Accordingly, the maximum height of the gas-liquid interface at the center of the region can be calculated from the amount of the sample dropped. For example, when V=15 μL, and a droplet on the substrate has a radius of 2.5 mm, maximum height H can be estimated to be equal to 1.15 mm. The estimation allows the droplet's geometry and size to be modeled and thus referenced in determining where the laser light should be radiated.

In step S3, kit 20 is irradiated with laser light 5 output from optical trapping light source 101. When sample 30 includes target DNA 18, and light irradiation starts and then a period of time has elapsed, gold nanoparticle assembly 10 is formed.

In step S4, image pick-up device 108 obtains an image of sample 30. Note that when image pick-up device 108 provides a moving image, image pick-up device 108 may start obtaining the image in step S3 before light irradiation starts.

In step S5, computation unit 106 processes the image provided from image pick-up device 108 and, from a result of the processing, determines whether target DNA 18 is present or absent. The image can be processed by a variety of known signal processing techniques.

For example, pattern recognition technology can be employed when what feature in geometry the gold nanoparticle assembly has with target DNA 18 present is previously known. As will be indicated hereinafter, a gold nanoparticle assembly under some measurement condition(s) is formed in a network. Computation unit 106 employs pattern recognition technology to extract a feature of a pattern of the network. Once the feature of the pattern has been extracted, it is determined that target DNA 18 is present. Alternatively, for example, whether target DNA 18 is present or absent can be determined based on the area of a portion of the image that has a deeper color resulting from transmitted light reduced as a gold nanoparticle assembly is formed.

One example of a result of having detected target DNA 18 will now be described with reference to an image obtained by image pick-up device 108. Sample 30 was prepared in the following method:

Initially, a dispersion liquid containing gold nanoparticle 11 modified with probe DNA 13 (hereinafter referred to as a dispersion liquid A) and a dispersion liquid containing gold nanoparticle 12 modified with probe DNA 14 (hereinafter referred to as a dispersion liquid B) were prepared independently. Dispersion liquids A and B contain gold nanoparticles at a concentration of 5.0 nM.

Gold nanoparticle 11 in dispersion liquid A of the concentration of 5.0 nM and gold nanoparticle 12 in dispersion liquid B of the concentration of 5.0 nM both have an average interparticle distance (or center-to-center distance) calculated to be 0.693 μm.

Furthermore, mixed liquid of equal amounts of dispersion liquid A, dispersion liquid B, and dispersion liquid containing an analyte will contain gold nanoparticles 11 and 12 each at a concentration of 5.0/3=1.66 nM. Accordingly, the mixed liquid of equal amounts of dispersion liquids contains gold nanoparticles 11 with an average interparticle distance calculated to be 0.999 μm and gold nanoparticles 12 with an average interparticle distance calculated to be 0.999 μm.

Furthermore, if the mixed liquid of equal amounts of dispersion liquids has gold nanoparticles 11 and gold nanoparticles 12 uniformly mixed together, and gold nanoparticles 11 and 12 are not distinguished from each other, then the gold nanoparticles will have a concentration of 1.66+1.66=3.33 nM. Accordingly the mixed liquid of equal amounts of dispersion liquids contains the gold nanoparticles with an average interparticle distance calculated to be 0.793 μm.

Note that it is known that DNA has adjacent bases with a distance of 0.34 nm therebetween. The present embodiment employs probe DNAs 13 and 14 each having 12 bases, and accordingly, probe DNAs 13 and 14 have a size (or length) calculated to be about 0.34×12=4.08 nm. Furthermore, target DNA 18 has 24 bases, and accordingly, target DNA 18 has a size calculated to be about 0.34×24=8.16 nm. Accordingly, preferably, before probe DNAs 13 and 14 and target DNA 18 hybridize together, the gold nanoparticles are dispersed in the liquid such that the gold nanoparticles have an averaged surface-to-surface distance larger than the sum of the lengths of probe DNA 13, probe DNA 14 and target DNA 18.

The gold nanoparticles' averaged surface-to-surface distance is calculated as the gold nanoparticles' average interparticle distance (or center-to-center distance) minus the gold nanoparticle's diameter. The above average interparticle distance of 0.793 μm minus the gold nanoparticle's diameter of 30 nm will be 0.790 μm. Thus the gold nanoparticles have an averaged surface-to-surface distance larger than the sum of the lengths of probe DNA 13, probe DNA 14 and target DNA 18, i.e., 4.08+4.08+8.16=16.32 nm, and thus satisfying the condition set forth above.

Then, 100 μM of an undiluted solution of target DNA and 100 μM of an undiluted solution of a mismatched DNA were prepared as an undiluted solution of sample 30. Target DNA 18 is a complementary DNA having a base sequence complementary to probe DNAs 13 and 14, as has been described with reference to FIG. 3. A mismatched DNA is a DNA which has a mismatched base and accordingly does not hybridize with probe DNA 13 or 14. The undiluted solution of the complementary DNA was diluted with a phosphate buffer 10,000-fold to provide a 10 nM diluted dispersion liquid. On the other hand, the undiluted solution of the mismatched DNA was diluted with a phosphate buffer 100-fold to provide a 1 μM diluted dispersion liquid. That is, the diluted dispersion liquid of the mismatched DNA has a concentration 100 times that of the diluted dispersion liquid of the complementary DNA.

The above dispersion liquids were used to prepare two samples for comparison. One sample contains 5 μL of dispersion liquid A, 5 μL of dispersion liquid B, and 5 μL of the diluted dispersion liquid of the complementary DNA. The other sample contains 5 μL of dispersion liquid A, 5 μL of dispersion liquid B, and 5 μL of the diluted dispersion liquid of the mismatched DNA. In other words, each sample has a volume of 15 μL. These samples were dropped on substrate 21.

FIG. 8 to FIG. 17 show images of the samples in the horizontal direction (i.e., the x and y directions shown in FIG. 4). Note that these images do not show liquid level guide 24 (See FIG. 5).

FIG. 8(A) shows an image of the sample containing the diluted dispersion liquid of the complementary DNA (concentration: 10 nM) naturally dried for 1 hour without undergoing light irradiation. With reference to FIG. 8(A), the complementary DNA and the probe DNAs hybridize together to form a network-like aggregate of gold nanoparticles.

In contrast, FIG. 8(B) shows an image of the sample containing the diluted dispersion liquid of the mismatched DNA (concentration: 1 μM) naturally dried for 1 hour without undergoing light irradiation, as observed on the substrate. With reference to FIG. 8(B), when the mismatched DNA and the probe DNAs do not hybridize together, a ball-like aggregate of approximately several μm was observed. As can be seen from FIG. 8(A) and FIG. 8(B), presence/absence of DNA hybridization presents a clear difference in geometry between aggregates observed after the samples are naturally dried.

FIG. 9(A) is an image of the diluted dispersion liquid of the complementary DNA (concentration: 10 nM) before light irradiation in a vicinity of a portion to be exposed to a beam waist. FIG. 9(B) is an image of the diluted dispersion liquid of the mismatched DNA (concentration: 1 μM) before light irradiation in a vicinity of a portion to be exposed to a beam waist.

With reference to FIG. 9(A) and FIG. 9(B), image pick-up device 108 obtains images of a region having a size of 69 μm×52 μm. Each image has a lower portion having a dark color, which is denoted as L, which corresponds to a liquid. Each image has an upper portion having a light color, which is denoted as A, which corresponds to a gas. A white portion between the liquid and the gas, which is denoted as I, is a gas-liquid interface. Before laser light 5 is radiated, gold nanoparticle assembly 10 is not observed in any of the diluted dispersion liquid of the complementary DNA or the diluted dispersion liquid of the mismatched DNA.

The above diluted dispersion liquids each had a vicinity of its gas-liquid interface irradiated with laser light 5 for a period of 2 minutes and 40 seconds. Optical trapping light source 101 outputs laser light 5 having an intensity set to 0.2 W.

FIG. 10(A) is an image of the diluted dispersion liquid of the complementary DNA (concentration: 10 nM) on the substrate after light irradiation, and FIG. 10(B) is an image of the diluted dispersion liquid of the mismatched DNA (concentration: 1 μM) on the substrate after light irradiation. FIG. 10(A) and FIG. 10(B) are compared with FIG. 9(A) and FIG. 9(B), respectively. Each image presents at the center a circle, which schematically represents the position of the beam waist of laser light 5. The beam waist, as seen in the vertical direction (or the z direction), is positioned 20 μm above substrate 21.

Initially, with reference to FIG. 10(A), in the diluted dispersion liquid of the complementary DNA, gold nanoparticle assembly 10 is formed in a vicinity of the beam waist.

On the other hand, with reference to FIG. 10(B), in the diluted dispersion liquid of the mismatched DNA, there is no gold nanoparticle assembly 10 clearly observed. Thus, while the diluted dispersion liquid of the mismatched DNA has a concentration 100 times that of the diluted dispersion liquid of the complementary DNA, gold nanoparticle assembly 10 is formed only when the complementary DNA is introduced.

The same samples were used and the beam waist's position is changed, and their images were obtained in a vicinity of the beam waist. The beam waist, as seen in the vertical direction (or the z direction), is positioned 15 μm above substrate 21.

Figure 11:
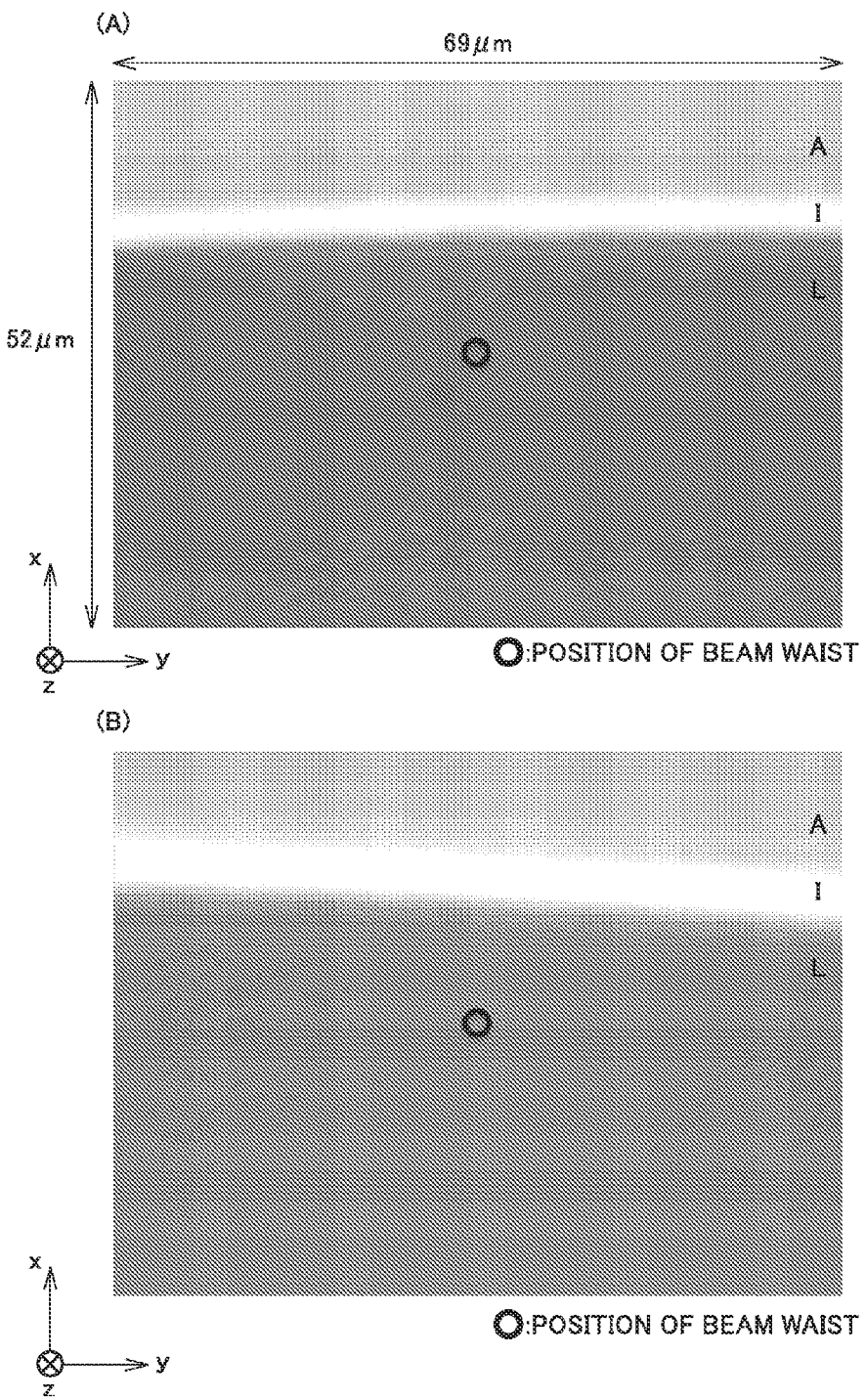
FIG. 11 shows (A) an optical transmission image of a liquid mixture before light irradiation in a vicinity of a portion to exposed to a beam waist having a different position, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a complementary DNA (concentration: 10 nM, and volume: 5 µL), and (B) an optical transmission image of a liquid mixture before light irradiation in a vicinity of a portion to exposed to a beam waist having a different position, the liquid mixture being a mixture of a dispersion liquid of gold nanoparticles modified with the first probe DNA (concentration: 5.0 nM, and volume: 5 µL), a dispersion liquid of gold nanoparticles modified with the second probe DNA (concentration: 5.0 nM, and volume: 5 µL), and a diluted dispersion liquid of a mismatched DNA (concentration: 1 µM, and volume: 5 µL).

FIG. 11(A) is an image of the diluted dispersion liquid of the complementary DNA (concentration: 10 nM) before light irradiation in a vicinity of a portion to be exposed to the differently positioned beam waist. FIG. 11(B) is an image of the diluted dispersion liquid of the mismatched DNA (concentration: 1 μM) in a vicinity of the differently positioned beam waist. FIG. 11(A) and FIG. 11(B) are compared with FIG. 9(A) and FIG. 9(B), respectively. With reference to FIG. 11(A) and FIG. 11(B), in FIG. 11, as well as FIG. 9, before light irradiation there is no gold nanoparticle assembly 10 clearly observed.

FIG. 12(A) is an image of the diluted dispersion liquid of the complementary DNA (concentration: 10 nM) on the substrate after light irradiation for the differently positioned beam waist. FIG. 12(B) is an image of the diluted dispersion liquid of the mismatched DNA (concentration: 1 μM) on the substrate. FIG. 12(A) and FIG. 12(B) are compared with FIG. 10(A) and FIG. 10(B), respectively.

With reference to FIG. 12(A), after light irradiation, gold nanoparticle assembly 10 is formed in a large region of 100 μm×100 μm or larger. When FIG. 12(A) is compared with FIG. 10(A), the former, which is the same sample as the latter, nonetheless presents gold nanoparticle assembly 10 larger in size. This may be because the sample's dispersion medium has evaporated as time elapses, and gold nanoparticles 11 and 12 and the complementary DNA accordingly have an increased concentration. Note that it is believed that gold nanoparticle assembly 10 in a vicinity of the beam waist was blown away by the pressure of laser light 5.

On the other hand, in FIG. 12(B), as well as FIG. 10(B), the diluted dispersion liquid of the mismatched DNA does not have any gold nanoparticle assembly 10 clearly observed.

In the above detected results, sample 30 dropped on substrate 21 contains the complementary DNA in an amount of substance of 10 nM×5 μL=50 fmol (1 fmol=$10^{-15}$ mol). Thus according to the present embodiment it can be seen that target DNA 18 of a trace amount of about 50 fmol is detectable.

The above amount of substance is an amount of substance of the complementary DNA that is contained in the entirety the sample 30 dropped. Accordingly, image pick-up device 108 obtains an image in a region containing the complementary DNA in an amount of substance smaller than 50 fmol. Thus it can be estimated that target DNA 18 of a trace amount smaller than 50 fmol is detectable.

Furthermore, according to FIG. 10(A) or FIG. 12(A), after the light irradiation in two minutes and 40 seconds at the latest, it is clearly confirmed that gold nanoparticle assembly 10 is present. However, if simply confirming whether gold nanoparticle assembly 10 has been formed is the purpose, a period of time for which radiation of laser light 5 is required may be shorter than two minutes and 40 seconds. For example, an experiment done by the present inventors for verification has indicated that even one minute or shorter of light irradiation allows a gold nanoparticle assembly to be confirmed. Thus it can be estimated that target DNA 18 of a trace amount smaller than 50 fmol is detectable in a short period of time within one minute.

Note that laser light 5 has an intensity of 0.2 W, which is one example of a measurement condition in the present embodiment, and laser light 5 is not limited to that intensity. For laser light intensity, there is an appropriate range depending on the metallic nanoparticle's type and concentration, the analyte's type and concentration and the host molecule's type and concentration, and the like. That is, a light intensity lower than the appropriate range's lower limit value cannot assemble the metallic nanoparticles in a vicinity of the beam waist. In contrast, a light intensity higher than the appropriate range's upper limit value may affect the analyte (e.g., heat it and thus have an effect to break a DNA bond). Accordingly, the laser light's optimal intensity is determined based on an experiment, as appropriate.

Then the diluted dispersion liquid of the complementary DNA is changed in concentration and an image thereof was obtained in a vicinity of the beam waist. The above-mentioned undiluted solution of the complementary DNA was diluted with a phosphate buffer 1,000,000-fold to provide a 10 pM diluted dispersion liquid. In other words, this diluted dispersion liquid contains the complementary DNA in a concentration of $1/100$ of that of the diluted dispersion liquid used in connection with FIG. 9 to FIG. 12. The samples are all equal in volume (i.e., 15 μL). Thus, the sample indicating a result of detection therefrom below contains the complementary DNA in an amount of substance of 50 fmol× $1/100$=500 amol (1 amol=$10^{-18}$ mol).

Figure 13:
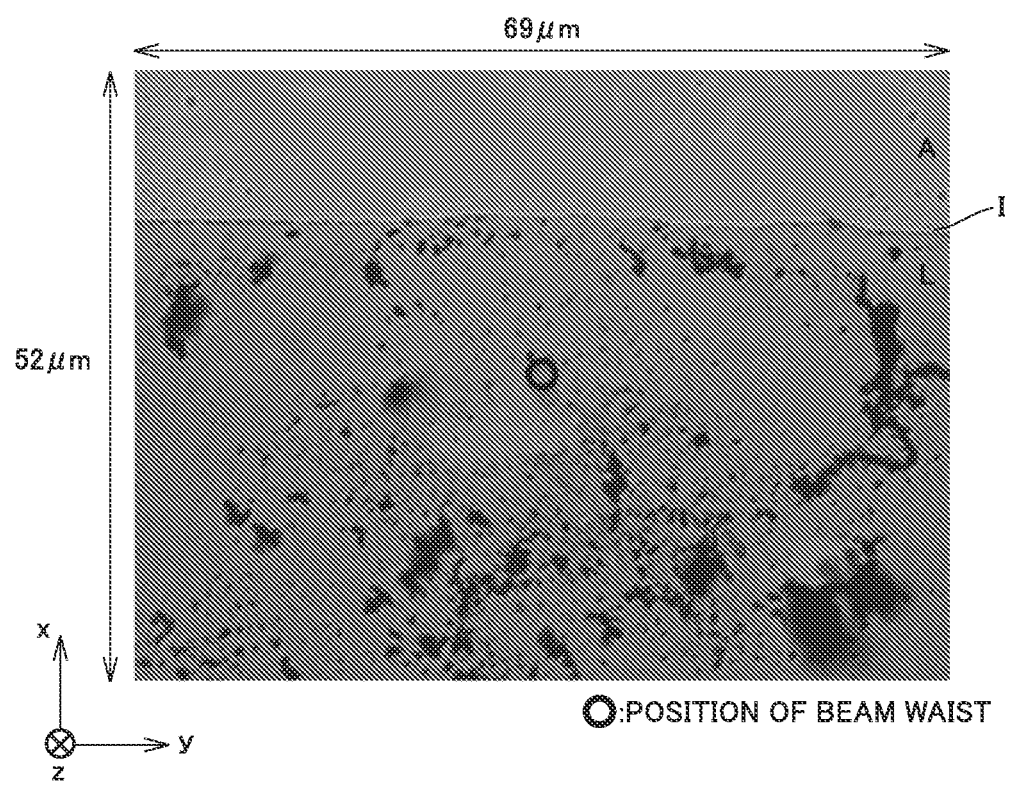
FIG. 13 is an optical transmission image of a diluted dispersion liquid of a complementary DNA that has a different concentration (of 100 pM) on a substrate after light irradiation.

FIG. 13 is an image of the diluted dispersion liquid of the complementary DNA that has a different concentration on a substrate after light irradiation. With reference to FIG. 13 the beam waist has the same position as that of the beam waist shown in FIG. 12(A) (i.e., 15 μm above substrate 21 as seen in the z direction). Light irradiation is also provided for the same period of time as that for FIG. 12(A).

The FIG. 13 gold nanoparticle assembly is smaller in size than the FIG. 12(A) gold nanoparticle assembly. This result shows that the gold nanoparticle assembly varies in size with in how much amount of substance a sample contains the complementary DNA.

Figure 16:
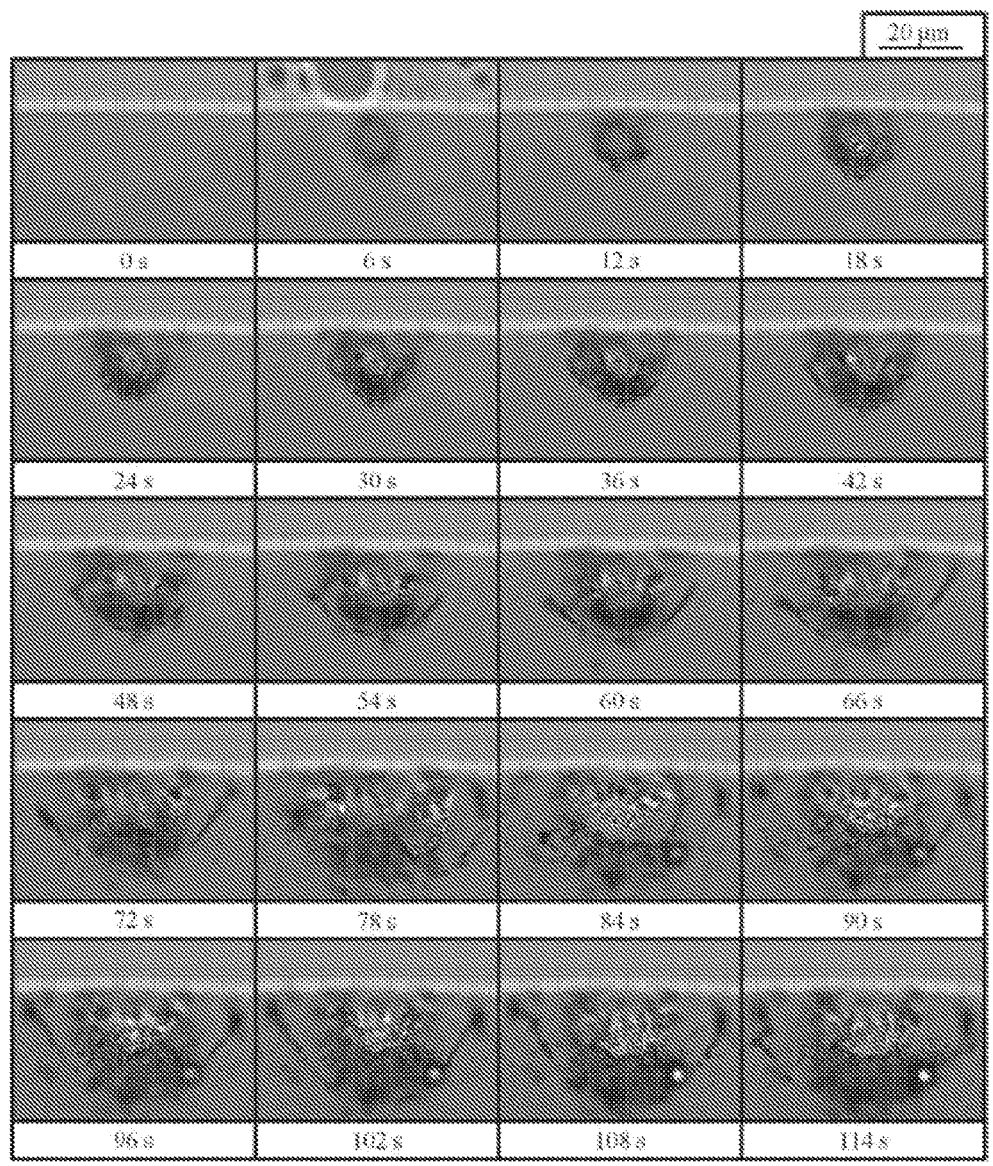
FIG. 16 presents successive photographic images (or optical transmission images) of a gas-liquid interface of a diluted dispersion liquid of a complementary DNA (concentration: 100 pM) (in a vicinity of a beam waist).

FIG. 14 presents successive photographic images of how a gas-liquid interface of the diluted dispersion liquid of the mismatched DNA (in a vicinity of the beam waist) after light irradiation starts varies with time. FIG. 15 presents successive photographic images of how a gas-liquid interface of the diluted dispersion liquid of the complementary DNA (in a vicinity of the beam waist) after light irradiation starts varies with time. FIG. 16 presents successive photographic images of a gas-liquid interface of the diluted dispersion liquid of the complementary DNA (in a vicinity of the beam waist) with a concentration of 100 pM. FIG. 17 presents successive photographic images of a gas-liquid interface of the diluted dispersion liquid of the complementary DNA (in a vicinity of the beam waist) with a concentration of 1 pM. The FIGS. 14-17 images are obtained for every 6 seconds with radiation of laser light 5 started at a time of 0 second. Furthermore, the positions respectively of liquid (L), gas (A), and gas-liquid interface (I) are not shown as they are equivalent to those shown in FIG. 9 to FIG. 13. Each sample has a volume of 15 μL.

Initially, with reference to FIG. 14, the aforementioned undiluted solution of the mismatched DNA was diluted with a phosphate buffer 100-fold to prepare a 1 μM diluted dispersion liquid. As the diluted dispersion liquid is dropped in a volume of 5 μL, sample 30 contains the mismatched DNA in an amount of substance of 1 μM×5 μL=5 pmol (1 pmol=$10^{-12}$ mol)

The sample containing the diluted dispersion liquid of the mismatched DNA does not present gold nanoparticle assembly 10 even after light irradiation. Note that an image obtained after 60 seconds shows a gas-liquid interface with bubble.

Then, with reference to FIG. 15, the undiluted solution of the complementary DNA was diluted with a phosphate buffer 10,000-fold to prepare a 10 nM diluted dispersion liquid. The sample contains the complementary DNA in an amount of substance of 10 nM×5 μL=50 fmol. That is, the complementary DNA has an amount of substance of $1/100$ of that of the mismatched DNA contained in the sample shown in FIG. 14. Furthermore, the complementary DNA has a concentration of 50 fmol/15 μL=3.3 nM.

A sample containing the complementary DNA in an amount of substance equal to that of the mismatched DNA contained in the FIG. 14 sample (i.e., a sample prepared by diluting the undiluted solution of the complementary DNA 100-fold) presents a gold nanoparticle assembly spontaneously formed with or without light irradiation. On the other hand, when the FIG. 15 sample diluted 10,000-fold is not irradiated with light, the gold nanoparticle assembly is less spontaneously formed. However, light irradiation and an elapse of at least a period of 6 seconds allow a gold nanoparticle assembly to be observed in a vicinity of the gas-liquid interface. It can be seen that thereafter the gold nanoparticle assembly rapidly grows as time elapses.

With reference to FIG. 16, the undiluted solution of the complementary DNA was diluted with a phosphate buffer 1,000,000-fold to prepare a 100 pM diluted dispersion liquid. The sample contains the complementary DNA in an amount of substance of 100 pM×5 μL=500 amol. That is, the complementary DNA has an amount of substance of $1/10,000$ of that of the mismatched DNA contained in the sample shown in FIG. 14. Furthermore, the complementary DNA has a concentration of 500 amol/15 μL=33 pM. The beam waist is positioned in the liquid horizontally (or in the x direction) inner than the gas-liquid interface by 13 μm and vertically (or in the z direction) above substrate 21 by 15 μm.

This diluted dispersion liquid of the complementary DNA also allows a gold nanoparticle assembly to be observed in a vicinity of the gas-liquid interface after at least a period of 6 seconds elapses. However, the gold nanoparticle assembly grows at a rate slower than that in FIG. 15.

With reference to FIG. 17, the undiluted solution of the complementary DNA was diluted with a phosphate buffer 100,000,000-fold to prepare a 1 pM diluted dispersion liquid. The sample contains the complementary DNA in an amount of substance of 1 pM×5 μL=5 amol. That is, the complementary DNA has an amount of substance of $1/1,000,000$ of that of the mismatched DNA contained in the sample shown in FIG. 14. Furthermore, the complementary DNA has a concentration of 5 amol/15 μL=0.33 pM. The beam waist is positioned in the liquid horizontally (or in the x direction) inner than the gas-liquid interface by 3 μm and vertically (or in the z direction) above substrate 21 by 5 μm.

This diluted dispersion liquid of the complementary DNA also allows a gold nanoparticle assembly to be observed in a vicinity of the gas-liquid interface after a period of 6 seconds elapses. Thereafter, as time elapses, the presence of the gold nanoparticle assembly becomes clearer. From this detection result it can be seen that the present embodiment allows even target DNA 18 of a trace amount of about 5 amol to be also detectable.

As can be seen from FIG. 14 to FIG. 17, while the sample containing the mismatched DNA does not present any change even through light irradiation, the sample containing the complementary DNA, even in an amount of substance of 50 fmol to 5 amol, presents a gold nanoparticle assembly through light irradiation. Thus a trace amount of target DNA 18 can specifically be detected. Furthermore, the gold nanoparticle assembly is formed at the beam waist located in a vicinity of the gas-liquid interface and thereafter grows as time elapses. It can be seen that the gold nanoparticle assembly's size and growth rate depend on the amount of substance of target DNA 18.

A trace amount of an analyte can be detected by other techniques including for example a gene detection method by polymerase chain reaction (PCR), enzyme-linked immunosorbent assay (ELISA), fluorescent staining flow cytometry or the like. However, for example, PCR requires repeating a cycle of amplifying DNA, and thus generally requires a detection time of several hours. ELISA and fluorescent staining flow cytometry also require a detection time of several hours.

In contrast, according to the present embodiment, whether a gold nanoparticle assembly is present can rapidly be confirmed within a short time of several seconds to 1 minute. Accordingly, the present embodiment can reduce the detection time to be significantly shorter than PCR or conventional methods for detecting a trace amount of an analyte.

In particular, if it is assumed in the FIG. 17 result that the complementary strands of DNA are dispersed uniformly in sample 30 before light irradiation starts, then, a region that is imaged (a region of 69 μm×52 μm) contains 12 complementary strands of DNA, i.e., approximately 0.02 amol (1 zmol=$10^{-21}$ mol). Accordingly, the present embodiment suggests a possibility of allowing an analyte of a significantly trace amount of an extent of sub-zepto mole to be detectable. Furthermore, if the region to be observed is previously determined, a possibility is indicated that the detection time can be shortened to about several seconds.

In the present embodiment one factor allowing a significantly reduced detection time is having adjusted the position of the beam waist to be in a vicinity of the gas-liquid interface of the sample. The sample's dispersion medium evaporates from the gas-liquid interface. This increases the density of the gold nanoparticles and target DNA 18 in a vicinity of the gas-liquid interface to be larger than that in the bulk. This provides an increased probability of the gold nanoparticles encountering target DNA 18 in the vicinity of the gas-liquid interface and thus facilitates DNA hybridization.

Another factor allowing a significantly reduced target DNA 18 detection time may be an effect of a convection flow generated as the laser light heats the dispersion medium around the beam waist. The convection flow allows a further increased probability of the gold nanoparticles encountering target DNA 18. Actually, a moving image obtained by the image pick-up device allows a convection flow to be observed.

For example, fluorescent staining flow cytometry or a similar technique using a fluorescent material requires a skillful engineer to subject a specimen to an advanced pretreatment. Furthermore, it also employs expensive reagents and an expensive detection device.

The present embodiment does not require fluorescent labeling, and can thus implement a so-called label-free detection. Furthermore, when the present embodiment is compared with fluorochrome staining, the former facilitates operating a detection device and preparing a regent and thus does not require a skilled engineer. Furthermore, the present embodiment allows the detection device to be simply configured and an inexpensive reagent to be used. Thus the present embodiment can provide the detection device at low cost.

While the present embodiment has been described for detection of DNA, the present invention allows an antigen to be detected via a gold nanoparticle modified with an antibody, rather than a probe DNA. As one example, albumin, which is a type of antigen, can serve as an analyte. In that case, the gold nanoparticle is modified with immunoglobulin (IgE), which is an antibody specifically compositing with albumin.

Albumin has a size (or a long axis) of about 10 nm (for example, bovine serum albumin has a size of 6.9 nm). Furthermore, an antibody typically has a size (or length) of 10-15 nm, and IgE has a size of about 10 nm. Accordingly, a sum of the antigen's size and twice the antibody's size is estimated to be about 30 nm. On the other hand, as has been described above, the averaged surface-to-surface distance of gold nanoparticles in a dispersion liquid is calculated based on the gold nanoparticles' concentration, and when the gold nanoparticles have a concentration equal to or smaller than 7.7 μM, the gold nanoparticles will have an averaged surface-to-surface distance of 30 nm or larger. In other words, the gold nanoparticles having the concentration of equal to or smaller than 7.7 μM in a dispersion liquid are dispersed in the dispersion liquid with an averaged surface-to-surface distance larger than a sum of the antigen's size and twice the antibody's size.

As one example, when a liquid mixture of a gold nanoparticle dispersion liquid and an albumin dispersion liquid contains gold nanoparticles in a concentration of 3.33 nM, then, the gold nanoparticles before forming a gold nanoparticle assembly have an averaged surface-to-surface distance represented by an average interparticle distance (or center-to-center distance) of 0.793 μm minus the gold nanoparticle's diameter of 30 nm, i.e., 0.790 μm, which is larger than 30 nm. It can thus be said that the gold nanoparticles are dispersed in the dispersion liquid with an averaged surface-to-surface distance larger than a sum of albumin's size and twice IgE's size.

Second Embodiment

The first embodiment employs an image of a sample to determine whether an analyte is present. However, the information for determining whether the analyte is present is not limited to the image. The present embodiment employs a sample's spectrum to determine whether an analyte is present.

A metallic nanoparticle in the second embodiment is a metallic nanoparticle that can cause localized surface plasmon resonance. For example, when the gold nanoparticle is irradiated with light of the visible to near-infrared ranges, localized surface plasmon resonance is induced on a surface of the gold nanoparticle. Any metallic nanoparticle other than the gold nanoparticle that can cause localized surface plasmon resonance is applicable to the present invention. Another such exemplary metallic nanoparticle is a silver nanoparticle, for example.

Figure 18:
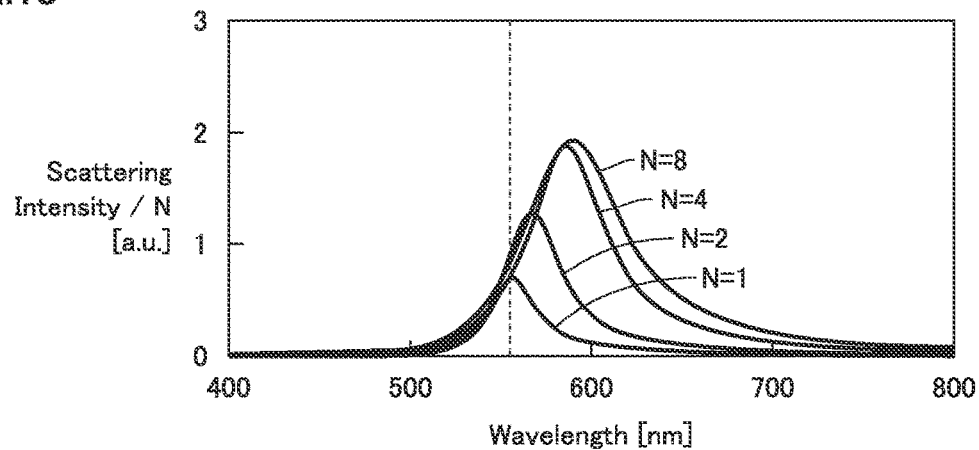
FIG. 18 represents a result of calculating how a scattering spectrum varies with the number of adjacent gold nanoparticles.

Gold nanoparticles irradiated with light and thus arranged adjacent to each other to a scale smaller than light's wavelength are irradiated with white light and their scattering spectrum is calculated. FIG. 18 shows a result of a calculation of how the scattering spectrum varies depending on the number N of adjacent gold nanoparticles. With reference to FIG. 18, the axis of ordinate represents intensity of scattered light per gold nanoparticle. A scattering spectrum's peak wavelength and peak width and an absorption spectrum's peak wavelength and peak width are substantially the same.

This calculation is done for number N having different values of 1, 2, 4 and 8, and presents a result indicating that number N having a larger value allows the scattering spectrum to have a peak wavelength more red-shifted than number N having a smaller value. Furthermore, number N having a larger value presents a peak wavelength range (e.g., a wavelength range of full width at half maximum) broader than number N having a smaller value. These optical response variations can be utilized to determine whether target DNA 18 is present.

Figure 19:
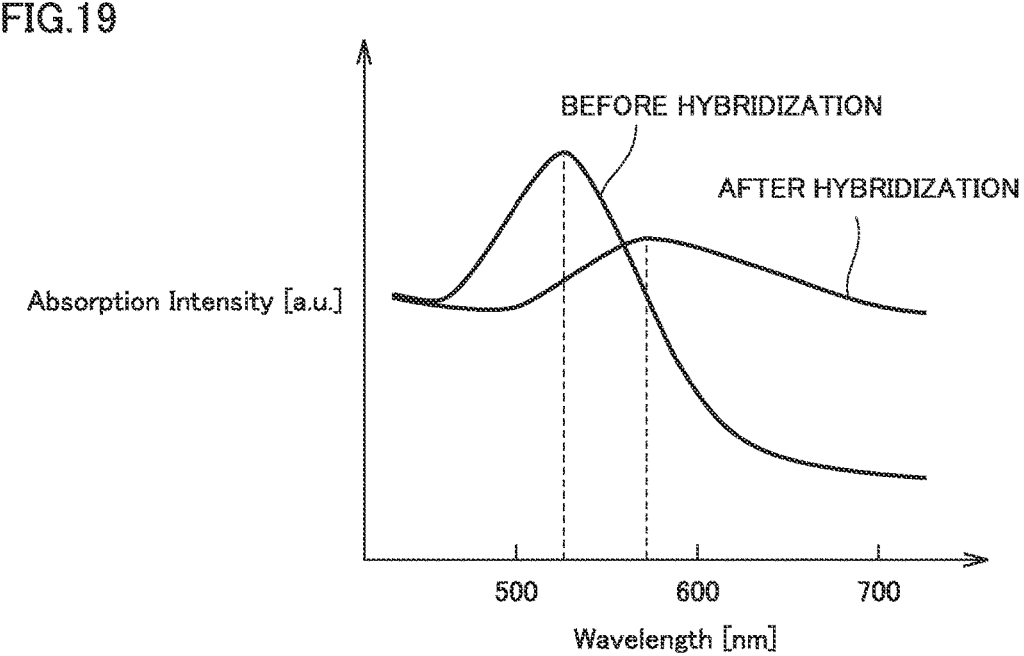
FIG. 19 represents how an absorption spectrum of gold nanoparticles varies between before and after their aggregation.

FIG. 19 represents how an absorption spectrum presented by gold nanoparticles 11, 12 varies between before and after their aggregation. With reference to FIG. 19, when a liquid having gold nanoparticles 11, 12 dispersed therein in a concentration of an extent is irradiated with white light and its absorption spectrum is measured, the absorption spectrum before DNA hybridization has a peak wavelength included in a wavelength range of green (e.g., a wavelength range of 495-570 nm). Accordingly, the color of the liquid containing gold nanoparticles 11 and 12 turns into the complementary color of green, i.e., red.

In contrast, after DNA hybridization, gold nanoparticle assembly 10 is formed, which increases number N of gold nanoparticles present in a vicinity of the beam waist of laser light 5. Accordingly, the absorption spectrum has the peak wavelength red-shifted and also broadened in range. The absorption spectrum after DNA hybridization has the peak wavelength in a wavelength range of yellow to orange color (e.g., a wavelength range of 570-620 nm). Accordingly, the color of the liquid turns into the complementary color of yellow to orange color, i.e., blue to bluish-purple color. Accordingly, spectrally dispersing the liquid containing gold nanoparticles 11 and 12 allows gold nanoparticle assembly 10 to be detected. That is, whether the liquid contains target DNA 18 can be determined.

Figure 20:
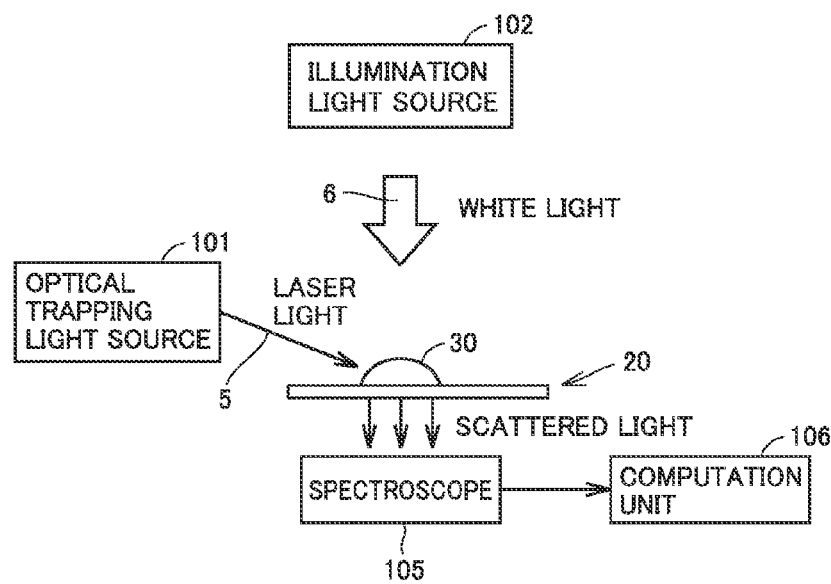
FIG. 20 schematically shows a configuration of a detection device according to a second embodiment of the present invention.
Figure 21:
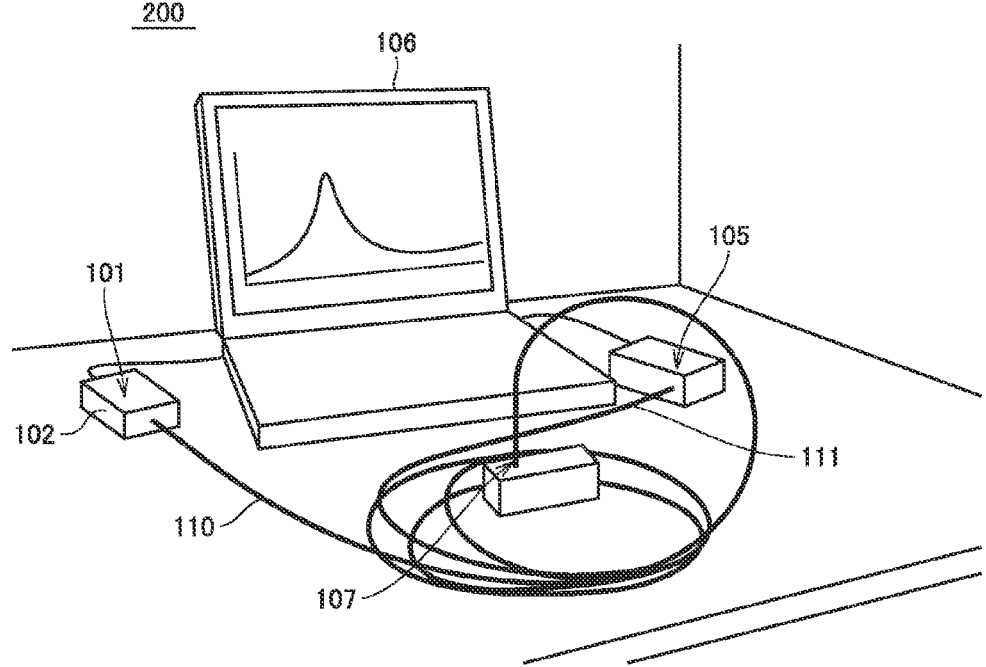
FIG. 21 is a perspective view of an appearance of the detection device shown in FIG. 20.
Figure 22:
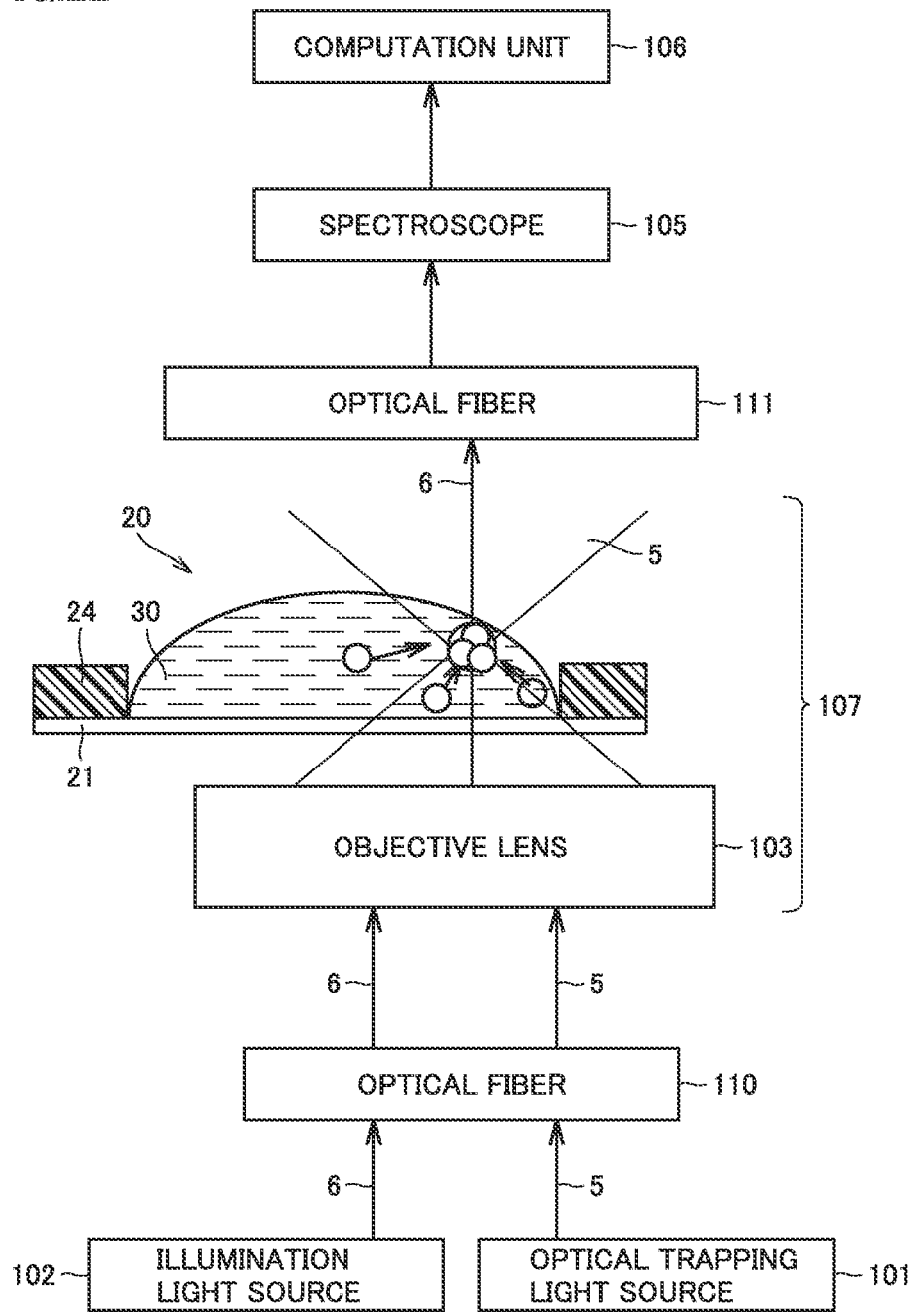
FIG. 22 is a block diagram for specifically illustrating a configuration of the detection device shown in FIG. 20.

FIG. 20 schematically shows a configuration of a detection device according to the second embodiment of the present invention. FIG. 21 is a perspective view of an appearance of a detection device 200 shown in FIG. 20. FIG. 22 is a block diagram for specifically illustrating a configuration of detection device 200 shown in FIG. 20.

With reference to FIGS. 20-22, illumination light source 102 (or the second light source) is a light source which emits white light 6, for example, and it is a halogen lamp, for example. Illumination light source 102 may be implemented as a laser light source. Note, however, that using a white light source as illumination light source 102 allows detection device 200 to be implemented at a low cost.

Illumination light source 102 may be a light source which emits substantially monochromatic light. The monochromatic light has a wavelength corresponding to that of a peak of localized surface plasmon resonance induced in gold nanoparticle assembly 10. The wavelength of the monochromatic light is only required to fall within a range in wavelength within twice the peak's full width at half maximum, and the line width of the monochromatic light is not particularly limited. The source of the monochromatic light may for example be a laser light source. Note that in FIG. 21 illumination light source 102 is accommodated in the same chassis that accommodates optical trapping light source 101 therein.

Optical trapping light source 101 and illumination light source 102 emit laser light 5 and white light 6, respectively, which are in turn guided via an optical fiber 110 to an optical probe 107. Optical probe 107 includes objective lens 103 and kit 20. White light 6 is introduced into objective lens 103 coaxially with laser light 5. These lights are focused by objective lens 103 to irradiate sample 30 therewith. Sample 30 transmits light, which is in turn guided by optical fiber 111 to a spectroscope 105. Note that laser light 5 and white light 6 may alternatively be radiated in mutually different directions.

Spectroscope 105 measures an absorption spectrum of localized surface plasmon resonance induced in gold nanoparticle assembly 10 formed in sample 30 and outputs to computation unit 106 a signal indicating a result of the measurement. Spectroscope 105 receives white light 6 radiated from illumination light source 102 to irradiate the liquid and having passed through the liquid, and accordingly, spectroscope 105 corresponds to a "photoreceiver" according to the present invention. Preferably, spectroscope 105 is a spectroscope capable of measuring a spectrum in an ultraviolet to near-infrared range (e.g., a wavelength range of 200 nm to 1100 nm). Furthermore, it is preferable that spectroscope 105 has smaller wavelength resolution. For example, the wavelength resolution of spectroscope 105 is equal to or smaller than 10 nm, equal to or smaller than 5 nm, equal to or smaller than 2 nm, or equal to or smaller than 1 nm, however, it is not limited thereto. Computation unit 106 tracks how the absorption spectrum of gold nanoparticle assembly 10 varies when gold nanoparticles 11 and 12 are aggregated by DNA hybridization. The remainder of detection device 200 in configuration is equivalent to that of detection device 100 (see FIG. 4), and accordingly, will not be described repeatedly.

Figure 23:
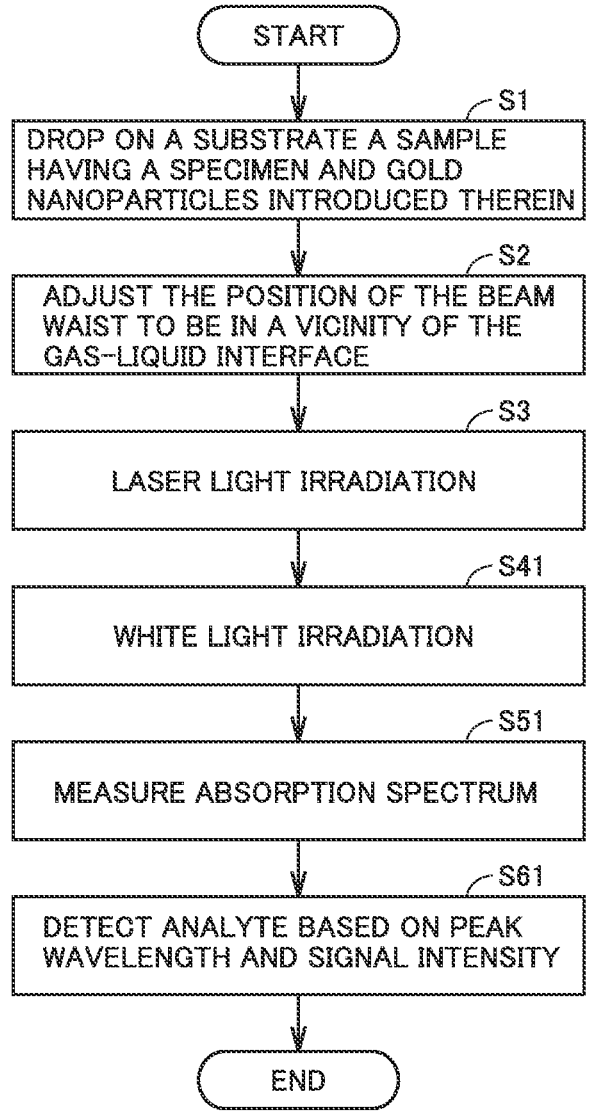
FIG. 23 is a flowchart for illustrating a method for detecting an analyte according to the second embodiment of the present invention.

FIG. 23 is a flowchart for illustrating a method for detecting an analyte according to the second embodiment of the present invention. With reference to FIG. 23, the process up to step S3 is equivalent to that in FIG. 7, and accordingly, will not be described repeatedly.

In step S41, illumination light source 102 starts to irradiate kit 20 for example with white light 6. Note that step S41 may precedes step S3 to start radiating white light 6 before radiating laser light 5.

In Step S51, spectroscope 105 operates to measure any absorption spectrum of localized surface plasmon resonance of any gold nanoparticle assembly 10. If gold nanoparticle assembly 10 is present, it presents an absorption spectrum having a peak wavelength red-shifted and also having a broadened peak wavelength range.

In Step S61, computation unit 106 detects an analyte, based for example on the absorption spectrum's peak wavelength and the signal intensity presented at the peak wavelength. For example, a preliminary experiment is performed to measure a relationship between the concentration of an analyte in a sample and a signal intensity ratio in the absorption spectrum. Computation unit 106 stores this relationship previously for example as a table. Computation unit 106 calculates a signal intensity ratio from a result of a measurement done by spectroscope 105. Computation unit 106 detects the analyte if the calculated signal intensity ratio exceeds a reference value. The reference value is previously set according to the above table.

Note that computation unit 106 may use the relationship defined in the above table and a signal intensity ratio obtained from a result of a measurement done by spectroscope 105 to calculate the analyte's concentration. Furthermore, a result of a preliminary experiment may be used to determine a function for deriving an analyte's concentration from a signal intensity ratio, and computation unit 106 may use the function and the intensity of a signal measured by spectroscope 105 to calculate the concentration of the analyte.

Furthermore, the sample's scattering spectrum or extinction spectrum may be measured, rather than its absorption spectrum. An extinction spectrum is a sum of a scattering spectrum and an absorption spectrum. Accordingly, when discussing where a peak is located, measuring a scattering spectrum or measuring an extinction spectrum is substantially equivalent to measuring an absorption spectrum. In any of the cases, localized surface plasmon presents a substantially identical spectral peak position.

If a DNA having a base sequence with only a single base different than the base sequence of the complementary DNA should be introduced into a sample, that DNA can hybridize with a target DNA. However, an absorption spectrum presented when the complementary DNA is introduced is different from that presented when the DNA different by only a single base is introduced. Accordingly, for example, computation unit 106 can have an absorption spectrum of a gold nanoparticle assembly formed by hybridization with the complementary DNA and an absorption spectrum of a gold nanoparticle assembly formed by hybridization with the DNA different by only a single base, previously stored therein to distinguish a mismatch of that single base.

Third Embodiment

In a third embodiment, a surface enhanced Raman scattering (SERS) spectrum is measured. Kit 20 according to the first embodiment of the present invention (see FIG. 5) can be utilized as a substrate for SERS. The third embodiment employs a detection device that is equivalent in configuration to detection device 200 (see FIGS. 20-22), and accordingly, will not be described repeatedly.

Gold nanoparticles 11 and 12 are conjugated by target DNA 18, and, with gold nanoparticle assembly 10 formed, kit 20 is irradiated with white light. Localized surface plasmon resonance is enhanced in a gap formed between gold nanoparticles 11, 12. That is, an electric field is enhanced in the gap between gold nanoparticles 11, 12. In general, Raman scattering is a third-order nonlinear optical process, and accordingly, Raman scattering light has intensity enhanced non-linearly for larger electric field intensity. As the electric field is enhanced, Raman scattering light is significantly increased in intensity. Spectroscope 105 detects increased Raman scattering light. Target DNA 18 is thus detected. Note that the SERS described in this embodiment can include surface enhancement resonant Raman scattering (SERRS).

Fourth Embodiment

A detection method according to an embodiment of the present invention can be applied to a conventional detection device detecting a trace amount of an analyte, to achieve enhanced detection sensitivity and reduced detection time. Furthermore, label-free detection can be implemented. In a fourth embodiment will be described a configuration allowing apply a detection method according to an embodiment of the present invention to be applied to a DNA chip reader device.

Figure 24:
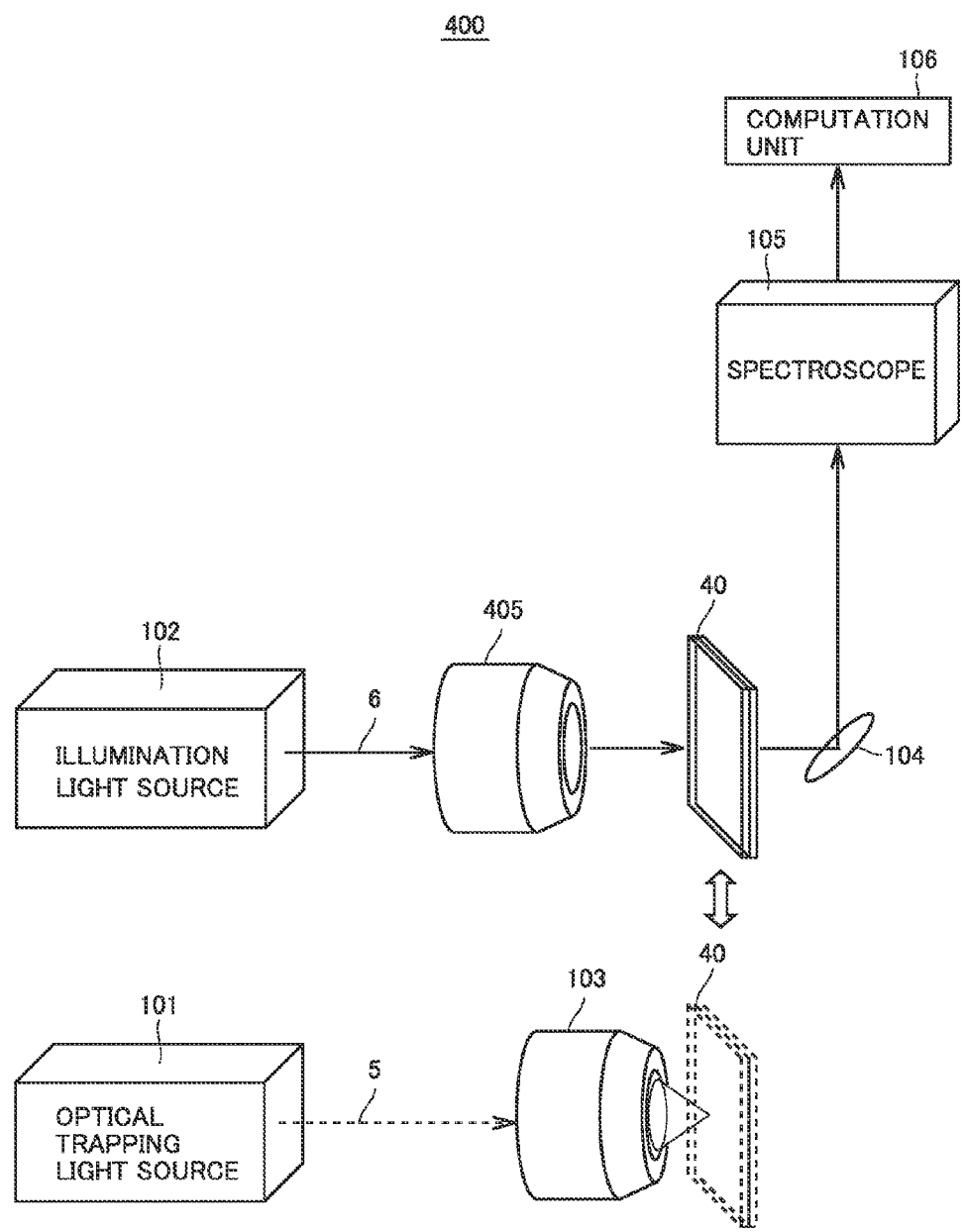
FIG. 24 schematically shows a configuration of a detection device according to a fourth embodiment of the present invention.
Figure 25:
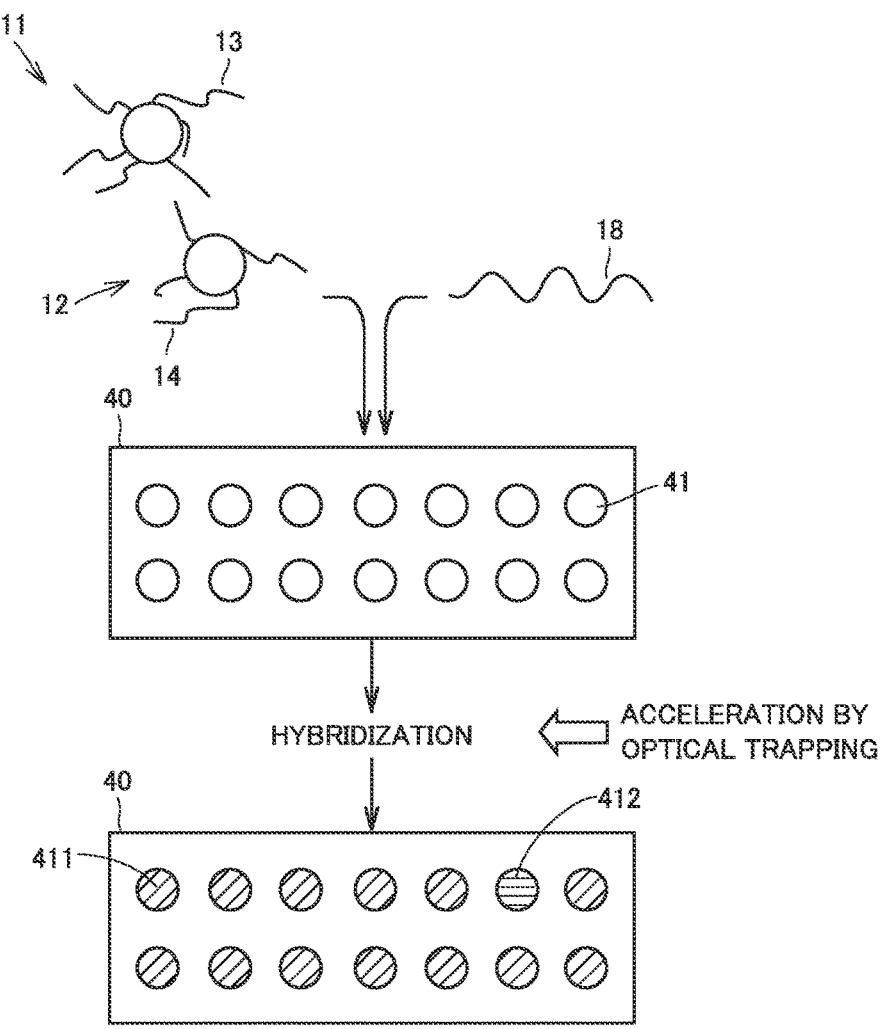
FIG. 25 is a diagram for illustrating how a process in the detection device shown in FIG. 24 proceeds.

FIG. 24 schematically shows a configuration of a detection device according to the fourth embodiment of the present invention. FIG. 25 is a diagram for illustrating how a process in a detection device 400 shown in FIG. 24 proceeds.

With reference to FIG. 24 and FIG. 25, detection device 400 includes a DNA chip 40, optical trapping light source 101, objective lens 103, illumination light source 102, optical component 104, an objective lens 405, filters 406, 407, a CCD camera 408 (a photoreceiver), and computation unit 106.

On DNA chip 40, generally several hundreds to several tens of thousands of spots 41 are arranged. In FIG. 25, only some of the spots are shown by FIG. 25 due to a limit in drawing. Each spot 41 can be configured for example with the configuration of the FIG. 5 kit 20 applied thereto. Each spot 41 receives a liquid dropped thereon having contained therein gold nanoparticles 11 and 12 modified with different probe DNAs, and has thus gold nanoparticles 11, 12 introduced therein. Each spot 41 receives a liquid dropped thereon having target DNA 18 contained therein.

Initially, to cause DNA hybridization, each of spots 41 is irradiated with light output from optical trapping light source 101. This accelerates hybridization of target DNA 18 and probe DNAs 13 and 14. In general, DNA hybridization requires about half a day. In contrast, the present embodiment allows significantly reduced hybridization reaction time. Note that, irradiating a plurality of spots 41 with light simultaneously, can reduce a period of time required to irradiate all of spots 41 with light.

Illumination light source 102 for example radiates white light 6 via objective lens 405 to irradiate each spot 41. Filters 406, 407 are selectively set on a path of light transmitted through DNA chip 40.

Filter 406 transmits light of a wavelength range including a peak wavelength of an absorption spectrum presented before DNA hybridization (e.g., the wavelength range of green (see FIG. 19)), while filter 406 interrupts light of any other wavelength. In contrast, filter 407 transmits light of a wavelength range including a peak wavelength of an absorption spectrum presented after DNA hybridization (e.g., the wavelength range of yellow to orange color), while filter 407 interrupts light of any other wavelength. The lights having passed through filters 406, 407 have light intensity depending on presence/absence of DNA hybridization in each spot 41.

CCD camera 408 outputs to computation unit 106 a signal depending on the light intensity of each spot 41. Computation unit 106 determines whether there is hybridization with target DNA 18 for each spot 41 from a ratio between a signal indicative of intensity of light transmitted through filter 406 and a signal indicative of intensity of light transmitted through filter 407.

More specifically, a spot having introduced therein a probe DNA which does not hybridize with target DNA 18 has a relatively large absorption of light of the wavelength range that filter 406 transmits therethrough, whereas the spot has a relatively small absorption of light of the wavelength range that filter 407 transmits therethrough. Accordingly the spot presents relatively larger light intensity with filter 407 set.

In contrast, a spot having introduced therein a probe DNA which hybridizes with target DNA 18 has a relatively small absorption of light of the wavelength range that filter 406 transmits therethrough, whereas the spot has a relatively large absorption of light of the wavelength range that filter 407 transmits therethrough. Accordingly the spot presents relatively larger light intensity with filter 406 set.

There are two types of spots 411 and 412 depending on relative magnitude in light intensity presented with filters 406, 407 set. Spot 411 presents relatively large light intensity with filter 407 set. This indicates that a probe DNA that modifies a surface of a gold nanoparticle introduced into spot 411 does not hybridize with target DNA 18. In contrast, spot 412 presents relatively large light intensity with filter 406 set. This indicates that a probe DNA that modifies a surface of a gold nanoparticle introduced into spot 412 hybridizes with target DNA 18.

Note that computation unit 106 may determine whether target DNA 18 is present from only a signal indicative of light intensity presented with one of filters 406 and 407 set. Furthermore, one of filters 406, 407 may alone be used.

Furthermore, gold nanoparticles 11 having their surfaces with probe DNA 13 thereon stained with a fluorochrome, and then integrated by laser light, allow localized surface plasmon to present enhanced emission allowing highly sensitivity.

Furthermore, a DNA chip having a different configuration from the FIG. 25 configuration may be used. Specifically, a DNA chip is prepared that has previously fixed in each spot 41 one of probe DNAs 13 and 14 having known base sequences. This DNA chip can be used to detect target DNA 18.

Figure 26:
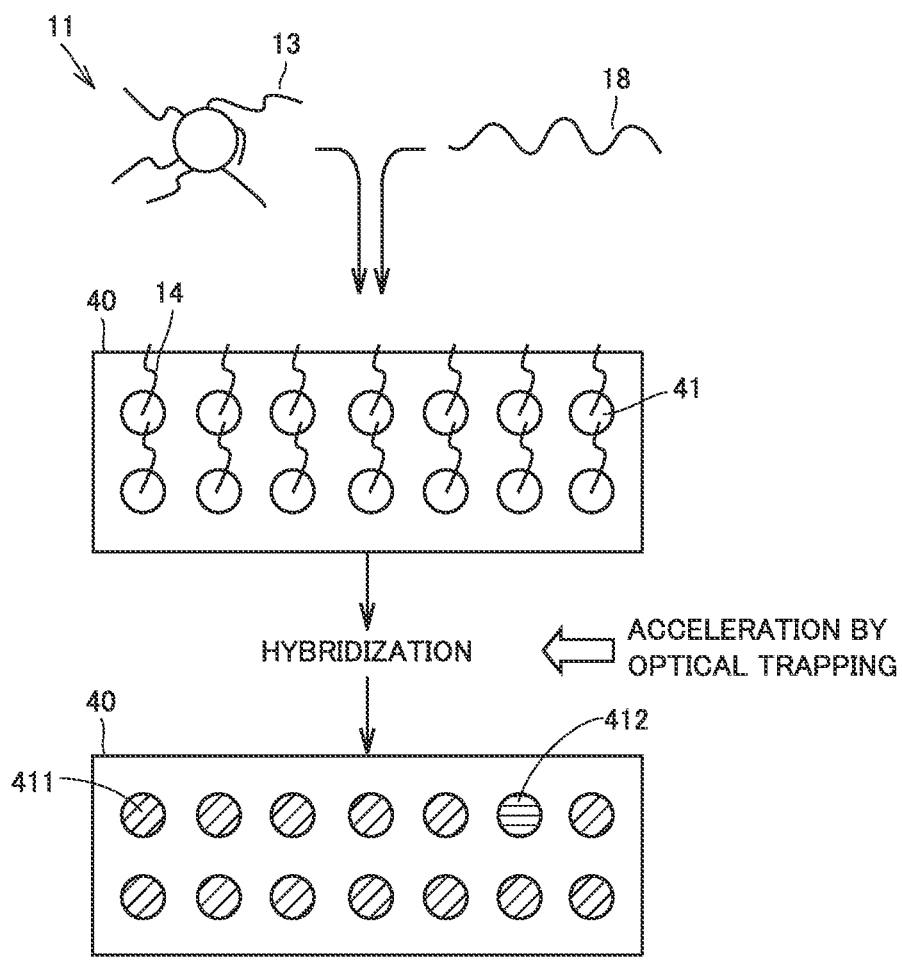
FIG. 26 is a diagram for illustrating how a detection process using a DNA chip different from a DNA chip shown in FIG. 25 proceeds.

FIG. 26 is a diagram for illustrating how a detection process using a DNA chip different from DNA chip 40 shown in FIG. 25 proceeds. With reference to FIG. 26, DNA chip 40 has spots 40 thereon each having a different DNA 14 previously fixed thereto. Each spot 41 receives a liquid dropped thereon having contained therein gold nanoparticles 11 modified with probe DNA 13, and also receives a liquid having target DNA 18 contained therein. The remainder of FIG. 26 in configuration is equivalent to that of FIG. 25, and accordingly, will not be described repeatedly.

The above configuration can accelerate hybridization of target DNA 18 and probe DNAs 13 and 14 to rapidly detect an analyte or target DNA 18.

Fifth Embodiment

As has been set forth in the second embodiment, a DNA that hybridizes with a probe DNA is not limited to a complementary DNA. If a DNA having a base sequence different from a complementary DNA is introduced into a sample, with the base sequence matching that of the complementary DNA at a rate larger than or equal to a prescribed value, that DNA can hybridize with the probe DNA. A detection device according to a fifth embodiment obtains an image of a gold nanoparticle assembly formed through light irradiation for a plurality of types of samples having introduced therein DNAs having base sequences different from that of the complementary DNA and measures each sample's absorption spectrum. The detection device then determines what type of DNA the sample has introduced therein, based on how the absorption spectrum varies with time.

FIG. 27 is a diagram for illustrating a probe DNA and four types of DNAs that can serve as an analyte and have mutually different base sequences. With reference to FIG. 27, the present embodiment employs a probe DNA identical to that used in the first embodiment (see FIG. 3). More specifically, probe DNA 13 (SEQ ID NO: 1) is a single strand of DNA having a 3' end with a thiol group (represented as SH), and a 5' end with 12 thymines (represented as T) between the 5' end and the thiol group. Probe DNA 14 (SEQ ID NO: 2) is a single strand of DNA having a 5' end with a thiol group, and a 3' end with 12 thymines between the 3' end and the thiol group.

Target DNA 18 is the same as that used in the first embodiment. More specifically, target DNA 18 (SEQ ID NO: 3) is a single strand of DNA having a 5' end and a 3' end with 24 adenines (represented as A) therebetween. Between target DNA 18 and probe DNAs 13 and 14, all base pairs have a complementary relationship, and accordingly, target DNA 18 is also referred to as a "complementary DNA."

A target DNA 18B (SEQ ID NO: 4) is a single strand of DNA having a 5' end and a 3' end with 24 thymines therebetween. Between DNA 18B and probe DNAs 13 and 14, all base pairs are mismatched, and accordingly, DNA 18B is also referred to as a "completely mismatched DNA."

A target DNA 18C (SEQ ID NO: 5) is a single strand of DNA having 12 adenines adjacent to the 5' end and 12 thymines adjacent to the 3' end. DNA 18C have bases with a half thereof closer to the 5' end complementary to those of probe DNAs 13 and 14 and a half thereof closer to the 3' end failing to match those of probe DNAs 13 and 14, and accordingly, DNA 18C is also referred to as a "half mismatched DNA."

A DNA 18D (SEQ ID NO: 6) is a single strand of DNA having a 5' end and a 3' end with thymine and adenine alternately repeated from the 5' end toward the 3' end. It has the same number of bases as the other DNAs, i.e. 24 bases. DNA 18D has a complementary base and a mismatched base alternately repeated and accordingly, it is also referred to as an "alternately mismatched DNA."

Figure 28:
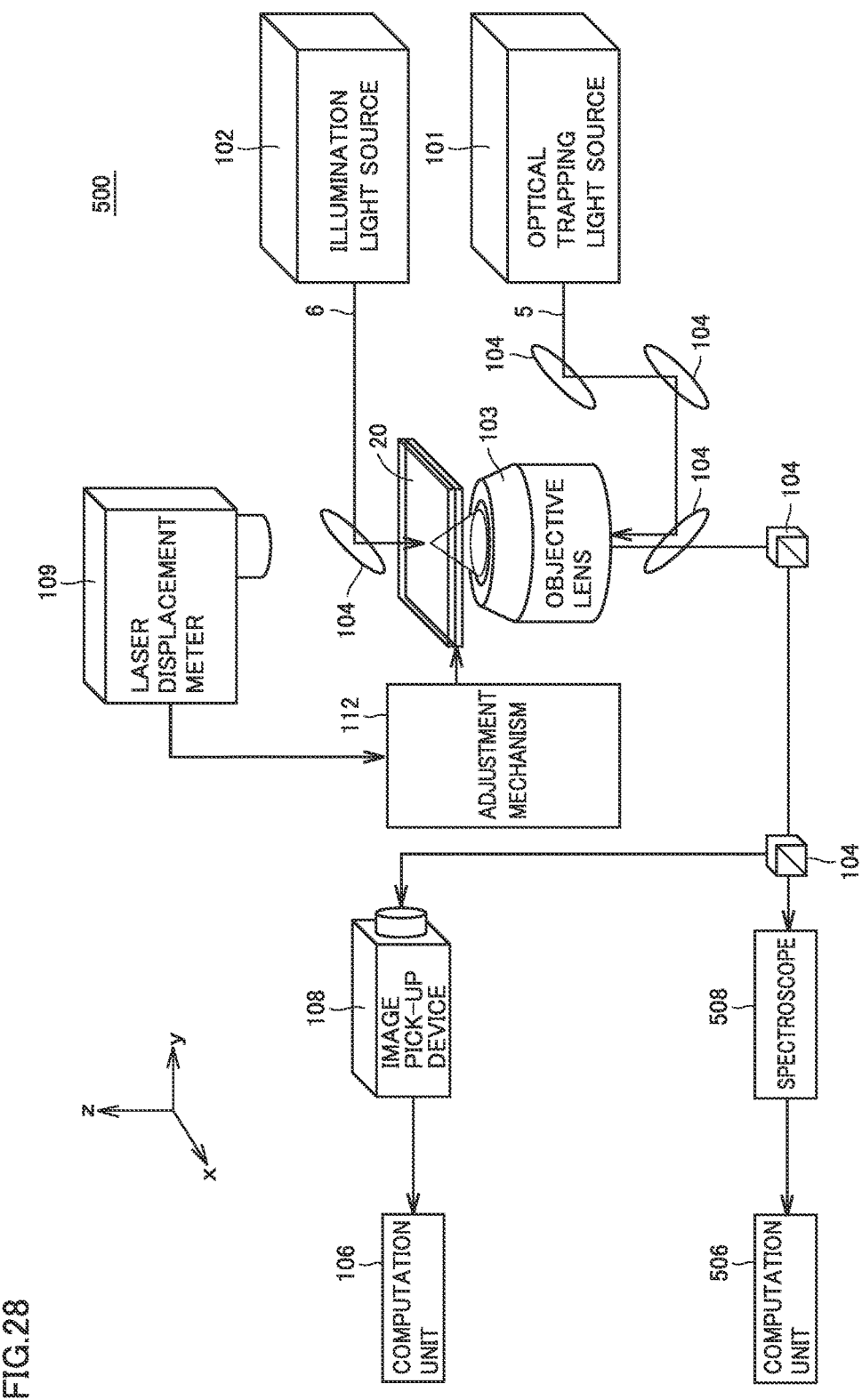
FIG. 28 schematically shows a configuration of a detection device according to a fifth embodiment of the present invention.

FIG. 28 schematically shows a configuration of a detection device according to the fifth embodiment of the present invention. With reference to FIG. 28, a detection device 500 is configured to be capable of obtaining an image of a vicinity of the beam waist of laser light 5 and also measure how an absorption spectrum varies with time. Detection device 500 is different from the FIG. 4 detection device 100 that the former further includes a computation unit (or detector) 506 and a spectroscope 508. Note that computation unit 506 may be configured to be integral with computation unit 106.

More specifically, spectroscope 508 measures an absorption spectrum of localized surface plasmon resonance induced on gold nanoparticle assembly 10 formed in sample 30, and outputs to computation unit 506 a signal indicating a result of the measurement. Spectroscope 508 can for example be a multichannel spectroscope.

If a DNA (e.g., a half-mismatched DNA and an alternately mismatched DNA) has a base sequence matching that of a complementary DNA at a rate equal to or larger than a prescribed value, computation unit 506 can detect that DNA as an analyte.

Detection device 500 provides a measurement, as below. A sample presents an absorption spectrum varying with time differently depending on what type of DNA the sample has introduced therein. The sample with the completely mismatched DNA does not present an absorption spectrum with a peak shift, whereas those with the complementary DNA, the half-mismatched DNA and the alternately mismatched DNA present a clear peak shift within several seconds to several minutes after light irradiation started. Furthermore, those with the complementary DNA, the half-mismatched DNA, and the alternately mismatched DNA have different periods of time after light irradiation started before they present peak shifts, and they present peaks shifted in amounts with different temporal change rates. Computation unit 506 tracks such a variation of a peak wavelength to determine what type of DNA a sample has introduced therein.

An example of a methodology of tracking how a peak wavelength varies will now be described more specifically. Computation unit 506 receives a signal indicative of an absorption spectrum from spectroscope 508 whenever a prescribed period of time (e.g., of 5 seconds) elapses. Computation unit 506 detects a peak for example from the absorption spectrum's primary and secondary differential coefficients to obtain a peak wavelength. And computation unit 506 obtains a period of time required before the peak wavelength is longer than a predetermined threshold value (e.g., 580 nm) with reference to a time at which light irradiation started.

Computation unit 506 previously holds a table (not shown) indicating an association between the above required period of time and types of DNA. Computation unit 506 refers to this table to determine, based on the required period of time, the type of DNA introduced into each sample. More specifically, computation unit 506 for example determines that when a sample having a DNA introduced therein requires a period of time of 0-50 seconds before the sample presents a peak wavelength longer than the predetermined threshold value the DNA is a complementary DNA. Computation unit 506 for example determines that when a sample having a DNA introduced therein requires a period of time of 50-100 seconds before the sample presents a peak wavelength longer than the predetermined threshold value the DNA is a half-mismatched DNA. Computation unit 506 for example determines that when a sample having a DNA introduced therein for example requires a period of time of 100-200 seconds before the sample presents a peak wavelength longer than the predetermined threshold value the DNA is an alternately mismatched DNA. Furthermore, if a sample having a DNA introduced therein does not present a peak shift after a period of time of 200 seconds elapsed, computation unit 506 determines that the DNA is a completely mismatched DNA.

Furthermore, as will be indicated hereafter, a complementary DNA presents a peak shift in a short period of time, whereas a half mismatched DNA presents a peak shift in a longer period of time. As such, instead of or in addition to calculating the above required period of time, computation unit 506 may calculate at what temporal change rate a peak wavelength is shifted in amount (i.e., a gradient of a curve shown in FIG. 33). Computation unit 506 previously holds a table indicating an association between temporal change rates in amount of shift of peak wavelength and types of DNA to therefrom determine a type of DNA from a temporal change rate in amount of shift of a peak wavelength. Furthermore, the calculation of the above required period of time and the calculation of a temporal change rate in amount of shifting of peak wavelength can be used together to provide determination with increased precision. The remainder of detection device 500 in configuration is equivalent to that of detection device 100, and accordingly, will not be described repeatedly.

Regarding the four types of diluted dispersion liquids having different types of DNA introduced therein as shown in FIG. 27, detection device 500 provides measurements, as will be described hereafter.

FIG. 29 presents successive photographic images of a gas-liquid interface of the diluted dispersion liquid of the complementary DNA (in a vicinity of the beam waist), as obtained after light irradiation started, and how the absorption spectrum varies with time. FIG. 29(A) shows images of the gas-liquid interface obtained through image pick-up device 108 for every 15 seconds with radiation of laser light 5 started at a time of 0 second. After light irradiation starts when a period of time of 150 seconds elapses light irradiation is stopped. Note that the positions respectively of liquid (L), gas (A) and gas-liquid interface (I) are not shown as they are equivalent to those shown in FIG. 9 to FIG. 13.

For the complementary DNA, formation of a gold nanoparticle assembly is clearly measured 15 seconds after light irradiation is started. Light irradiation is further continued and as time elapses in that condition, how the gold nanoparticle assembly grows is measured. In contrast, it can be seen that once a period of time of 150 seconds has elapsed, i.e., when light irradiation is stopped, the once grown-up gold nanoparticle assembly becomes small.

Then, with reference to FIG. 29(B), this absorption spectrum is measured using spectroscope 508. The axis of abscissa represents wavelength and the axis of ordinate represents absorbance. FIG. 29(B) presents curves, which represent an absorption spectrum presented 0 second, 30 seconds, 60 seconds, 90 seconds, 120 seconds, 150 seconds, and 180 second after radiation of laser light 5 is started.

Before light irradiation starts (or at 0 s) the absorption spectrum has a peak wavelength of 533.73 nm and presents an absorbance of 0.093 at the peak wavelength. Furthermore, after a period of time of 150 seconds elapsed, the absorption spectrum has a peak wavelength of 592.34 nm and presents an absorbance of 0.773 at the peak wavelength. Thus, the peak wavelength red-shifts as time elapses from initiation of light irradiation. Furthermore, that the absorption spectrum is broadened is also measured.

FIG. 30 presents successive photographic images of a gas-liquid interface of the diluted dispersion liquid of the completely mismatched DNA (in a vicinity of the beam waist) after light irradiation starts, and how the absorption spectrum varies with time. FIG. 30 is compared with FIG. 29.

With reference to FIG. 30(A), for the completely mismatched DNA, even irradiated with light, no formation of a gold nanoparticle assembly is measured.

With reference to FIG. 30(B), before light irradiation starts (or at 0 s) the absorption spectrum has a peak wavelength of 531.47 nm and presents an absorbance of 0.105 at the peak wavelength. Furthermore, after a period of time of 150 seconds elapsed, the absorption spectrum has a peak wavelength of 563.36 nm and presents an absorbance of 0.326 at the peak wavelength.

Note that, in the example of measurement indicated in FIG. 30, the absorption spectrum broadens after a period of time of 150 seconds elapsed. It is believed that this is because an assembly formed without resulting from radiation of laser light 5 has flown into a photometric area, as shown in an image shown in FIG. 30(A) that is presented after the period of time of 150 seconds elapsed.

FIG. 31 presents successive photographic images of a gas-liquid interface of the diluted dispersion liquid of the half mismatched DNA (in a vicinity of the beam waist) after light irradiation starts, and how the absorption spectrum varies with time. FIG. 31 is compared with FIG. 29 and FIG. 30.

With reference to FIG. 31(A), for the half mismatched DNA, formation of a gold nanoparticle assembly through light irradiation is measured. Note, however, that as is apparent from comparing an image obtained from the half mismatched DNA and that obtained from the complementary DNA that are obtained after a period of time of 150 seconds elapsed, the half-mismatched DNA forms an assembly sparser than that formed by the complementary DNA.

With reference to FIG. 31(B), before light irradiation starts (or at 0 s) the absorption spectrum has a peak wavelength of 535.78 nm and presents an absorbance of 0.078 at the peak wavelength. Furthermore, after a period of time of 150 seconds elapsed, the absorption spectrum has a peak wavelength of 596.57 nm and presents an absorbance of 0.791 at the peak wavelength.

FIG. 32 presents successive photographic images of a gas-liquid interface of the diluted dispersion liquid of the alternately mismatched DNA (in a vicinity of the beam waist) after light irradiation starts, and how the absorption spectrum varies with time. FIG. 32 is compared with FIG. 29 to FIG. 31.

With reference to FIG. 32(A), for the alternately mismatched DNA, formation of a gold nanoparticle assembly through light irradiation is measured. Note however, that the alternately mismatched DNA forms an assembly smaller than that formed by the complementary DNA.

With reference to FIG. 32(B), before light irradiation starts (or at 0 s) the absorption spectrum has a peak wavelength of 537.42 nm and presents an absorbance of 0.130 at the peak wavelength. Furthermore, after a period of time of 150 seconds elapsed, the absorption spectrum has a peak wavelength of 586.08 nm and presents an absorbance of 0.738 at the peak wavelength.

Figure 33:
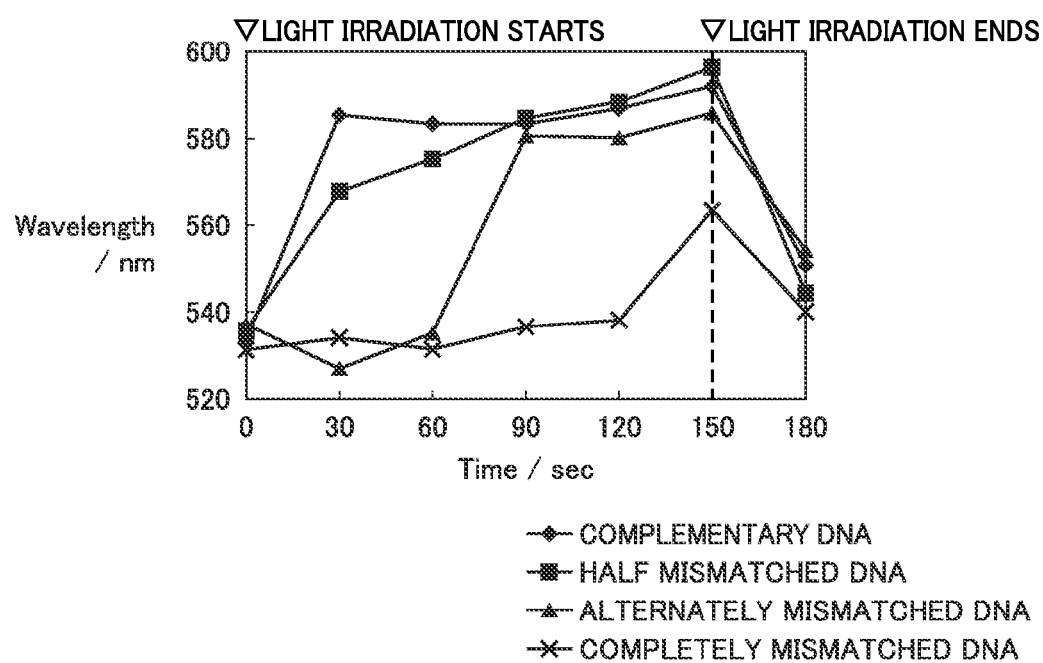
FIG. 33 is a diagram for illustrating how the absorption spectra shown in FIG. 29(B), FIG. 30(B), FIG. 31(B), and FIG. 32(B) have peaks shifted.

FIG. 33 is a diagram for illustrating how the absorption spectra shown in FIG. 29(B), FIG. 30(B), FIG. 31(B), and FIG. 32(B) have peaks shifted. With reference to FIG. 33, the axis of abscissa represents time having elapsed since light irradiation started, and the axis of ordinate represents peak wavelength. As has been set forth above, light irradiation stops 150 seconds after it started.

The complementary DNA presents a peak wavelength red-shifted after light irradiation started before a period of time of 30 seconds elapses. A period of time required before the peak wavelength is longer than a threshold value (580 nm) is estimated to be 30 seconds. On the other hand, for a period of time after 30 seconds before 150 seconds, the peak wavelength is substantially constant. And after a period of time of 150 seconds has elapsed, i.e., when light irradiation is stopped, the peak wavelength blue-shifts. This sufficiently matches the fact that a gold nanoparticle assembly is reduced in size once light irradiation has been stopped, as has been described with reference to FIG. 29(A).

When the half mismatched DNA is compared with the complementary DNA, the former presents a peak wavelength taking more time to red-shift immediately after light irradiation is started than the latter. However, the peak wavelength also continues to red-shift for a period of time after 30 seconds before 150 seconds. A period of time that the peak shift requires is estimated to be 90 seconds. While the half mismatched DNA requires time for peak shift, it presents a peak wavelength of the same extent as that of the complementary DNA for a point in time when a period of time of 150 seconds has elapsed.

The alternately mismatched DNA presents a peak wavelength substantially unchanged after light irradiation started before a period of time of 60 seconds elapses. In contrast, during a period of time after 60 seconds before 90 seconds, the peak wavelength red-shifts. A period of time that the peak shift requires is estimated to be 150 seconds. When the alternately mismatched DNA is compared with the complementary DNA or the half mismatched DNA, the former takes more time to present a peak shift.

The completely mismatched DNA does not present a peak wavelength substantially varying while it is irradiated with laser light 5. After a period of time of 150 seconds has elapsed the peak wavelength is temporarily red-shifted, because, as has been described with reference to FIG. 30, an assembly formed without resulting from light irradiation has flown into a photometric area.

Thus, a sample presents a peak wavelength varying differently depending on what type of DNA the sample has introduced therein. Thus, according to the present embodiment, detection device 500 tracks how a peak wavelength varies. Detection device 500 can thus determine what type of DNA a sample has introduced therein.

Detection device 500 according to the fifth embodiment can be used for example to identify a PCR product generated through polymerase chain reaction (PCR). Generally, when the PCR is used to determine whether a specific base sequence's DNA is amplified, a dye which emits fluorescence when it conjugates with that DNA is added to a reaction liquid, and fluorescence intensity is thus measured. In contrast, detection device 500 allows a peak wavelength's variation to be tracked to identify a PCR product without labeling with a fluorochrome. Alternatively, detection device 500 can refer to a peak shift's required period of time or a temporal change rate in amount of shifting of a spectrum to be used to assist in specifying an unknown DNA base sequence.

Note that the detection device of the fifth embodiment is also applicable to the DNA chip reader device described in the fourth embodiment. More specifically, a DNA chip has a plurality of spots each holding gold nanoparticles modified with a different probe DNA. A plurality of spots each receive a liquid dropped thereon having a target DNA contained therein and are subsequently simultaneously irradiated with light to measure how their absorption spectra vary with time. What types of DNA are present can thus be determined for the plurality of spots collectively, and an analyte(s) (or a target DNA(s)) can be detected in a reduced period of time.

Note that in the fifth embodiment, a complementary DNA corresponds to a "first target DNA," and either one of a half mismatched DNA and an alternately mismatched DNA corresponds to a "second target DNA." When the target DNA is either one of the "first target DNA" and the "second target DNA," computation unit 506 can determine whether the target DNA is the "first target DNA" or the "second target DNA," based on how a spectrum measured by spectroscope 508 varies with time.

While in the above has been described a configuration with detection device 500 including both image pick-up device 108 and spectroscope 508, image pick-up device 108 is not an essential component for detection device 500. Accordingly, image pick-up device 108 may be dispensed with.

Sixth Embodiment

In a sixth embodiment, the substrate holding a droplet is not used and a micro channel chip is instead used. A detection device that is used in the present embodiment is equivalent in configuration to the FIG. 4 detection device 100 except for the micro channel chip and accordingly, the detection device will not be described repeatedly.

Figure 34:
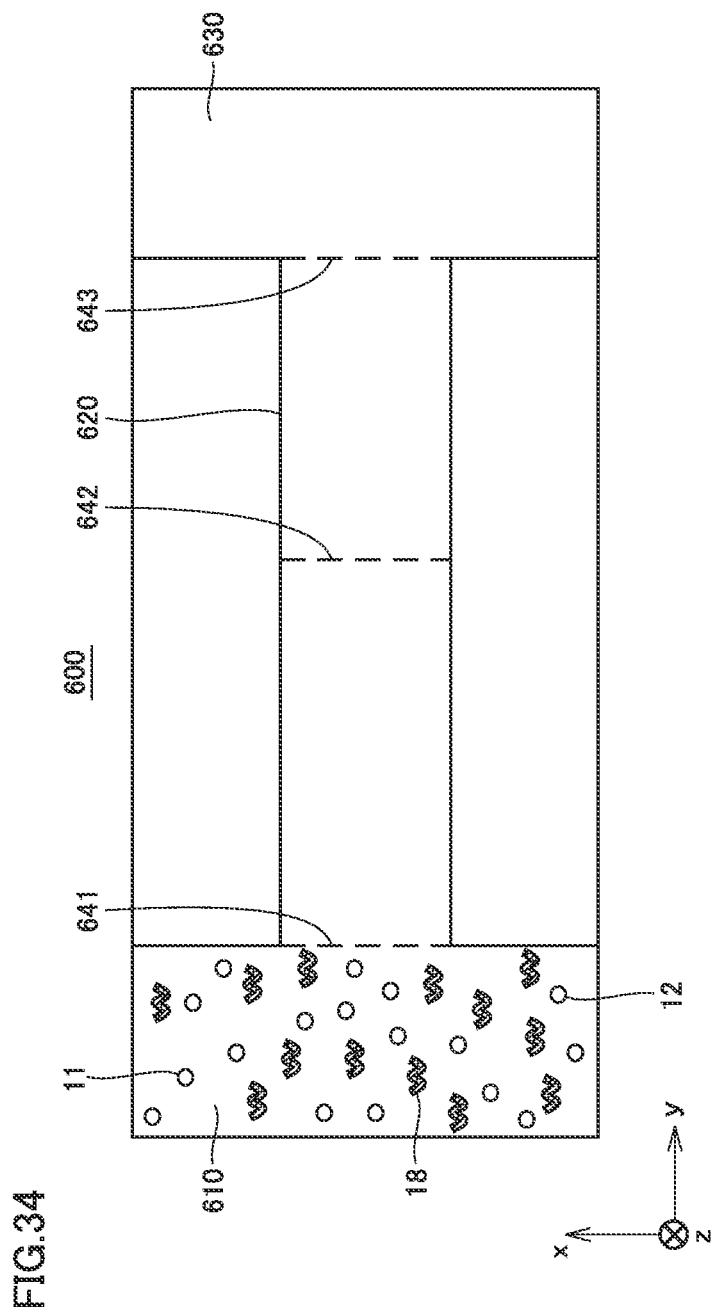
FIG. 34 is a schematic diagram for illustrating a micro channel chip in a state before injection is started.
Figure 35:
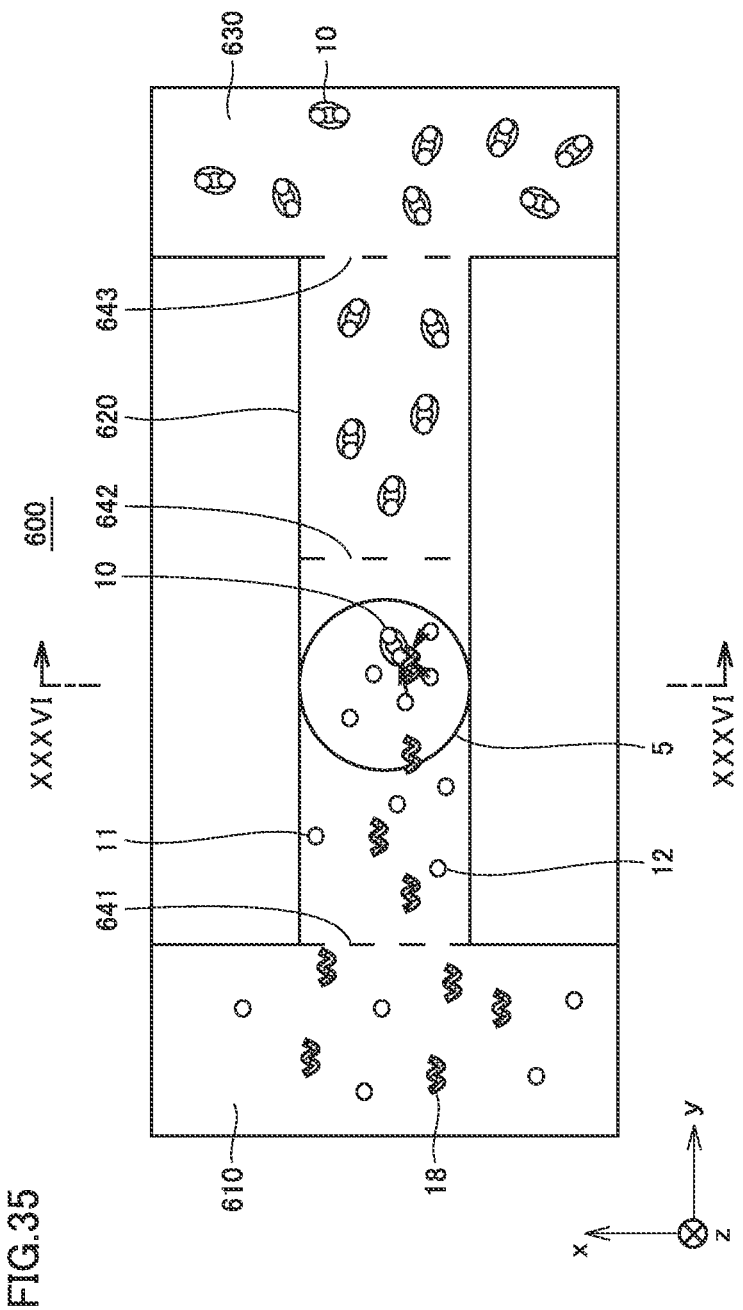
FIG. 35 is a schematic diagram for illustrating a micro channel chip in a state after injection is started.

FIG. 34 is a schematic diagram for illustrating a micro channel chip in a state before injection is started. FIG. 35 is a schematic diagram for illustrating a micro channel chip in a state after injection is started.

With reference to FIG. 34, a micro channel chip 600 has an inlet 610, a micro channel 620, and an outlet 630. Before injection is started, inlet 610 has introduced therein a sample containing target DNA 18 and gold nanoparticles 11 and 12.

Micro channel chip 600 is provided with valves 641-643 for controlling in amount (or flow rate) the sample passing through micro channel 620. Valves 641-643 are each implemented for example as a piezoelectric device. Valve 641 is provided at an end of micro channel 620 adjacent to inlet 610. Valve 642 is provided in the course of micro channel 620. Valve 643 is provided at an end of micro channel 620 adjacent to outlet 630. However, the number of valves and their locations are not particularly limited.

Subsequently, with reference to FIG. 35, when the sample is passed, laser light 5 is introduced into micro channel 620. Thus, gold nanoparticle assembly 10 is formed at a laser spot (indicated by laser light 5). Gold nanoparticle assembly 10 formed passes through the remainder of micro channel 620 and is stored in outlet 630.

In the first embodiment, laser light 5 is positioned to irradiate a gas-liquid interface therewith. This is done because at the gas-liquid interface a dispersion medium evaporates, which locally increases gold nanoparticles 11 and 12 and target DNA 18 in concentration. This increases the number of gold nanoparticles 11 and 12 and target DNA 18 passing across the laser spot and thus allows a gold nanoparticle assembly to be formed in a further shorter period of time.

The present embodiment that employs the micro channel chip allows gold nanoparticles 11 and 12 and target DNA 18 to be present in a narrow, limited region in micro channel chip 620 and also allows that region to be irradiated with laser light. This provides an increased probability of gold nanoparticles 11 and 12 and target DNA 18 passing across a laser spot (that is, a ratio of the number of gold nanoparticles 11 and 12 and target DNA 18 in a sample that pass across the laser spot to the total number of gold nanoparticles 11 and 12 and target DNA 18 in the sample, is increased). As a result the gold nanoparticle assembly can be formed in a reduced period of time. With gold nanoparticles 11 and 12 and target DNA 18 present in a narrow, limited region, it is not essential to position laser light 5 at the gas-liquid interface.

Figure 36:
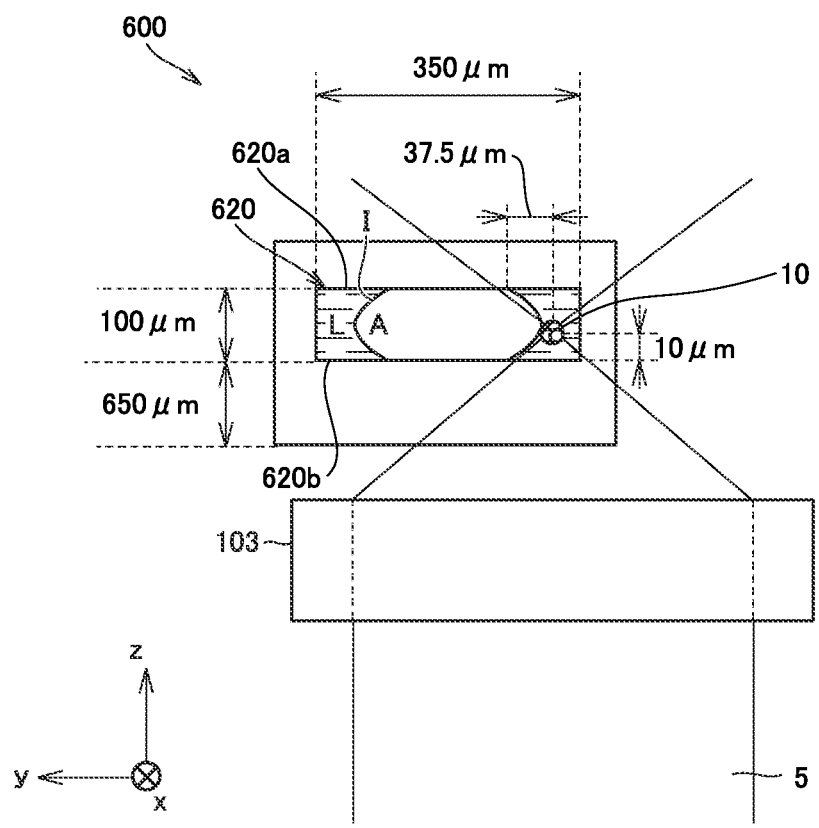
FIG. 36 is a cross section of a micro channel chip 600 taken along a line XXXVI-XXXVI shown in FIG. 35.

Hereinafter, an example of a result of a measurement using the micro channel chip will be described. FIG. 36 is a cross section of micro channel chip 600 taken along a line XXXVI-XXXVI shown in FIG. 35. With reference to FIG. 35, micro channel 620 has a width (i.e., a distance between side surfaces of micro channel 20) of 350 µm. Micro channel 620 has a height (a distance between a ceiling 620*a* of micro channel 620 and a bottom surface 620*b* of micro channel 620) of 100 µm. A distance between a lower surface of micro channel chip 600 in the z direction and bottom surface 620*b* of micro channel 620 is 650 µm.

Figure 37:
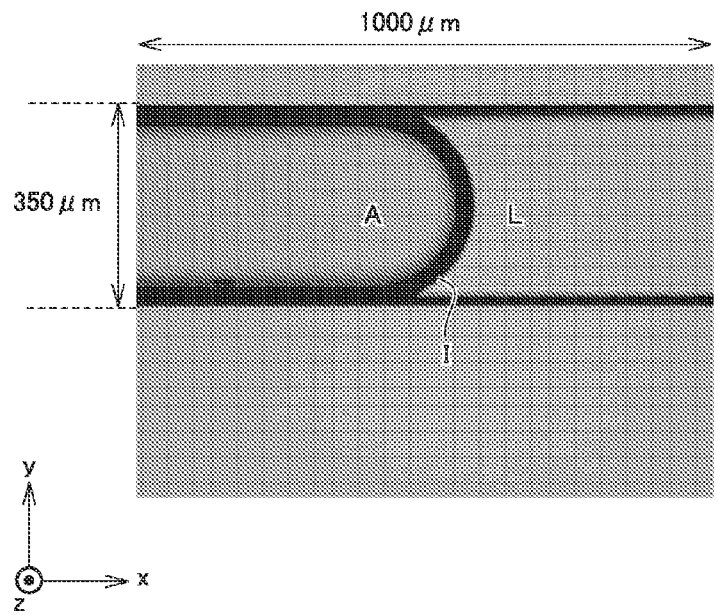
FIG. 37 is an optical transmission image of a vicinity of a gas-liquid interface formed in the micro channel before light irradiation starts, as obtained via an objective lens having a magnification of 10 times.

A liquid mixture (volume: 1.0 µL) of a dispersion liquid of gold nanoparticles 11, a dispersion liquid of gold nanoparticles 12, and a dispersion liquid of a target DNA (or complementary DNA) 18 with the target DNA having a concentration of 33 pM, was passed through micro channel 620. At the time, as shown in FIG. 37, a gas-liquid interface is formed in the course of micro channel 620. Laser light 5 was radiated in the z direction from below upward to irradiate micro channel 620. Objective lens 103 having a magnification of 40 times was used to adjust an optical system to form a beam waist in a vicinity of a gas-liquid interface of a meniscus internal to the liquid in a direction (i.e., in the x direction) along a channel formed on bottom surface 620*b* of micro channel 620. Laser light 5 had a wavelength of 1064 nm and at the beam waist had an output of 0.4 W.

Figure 38:
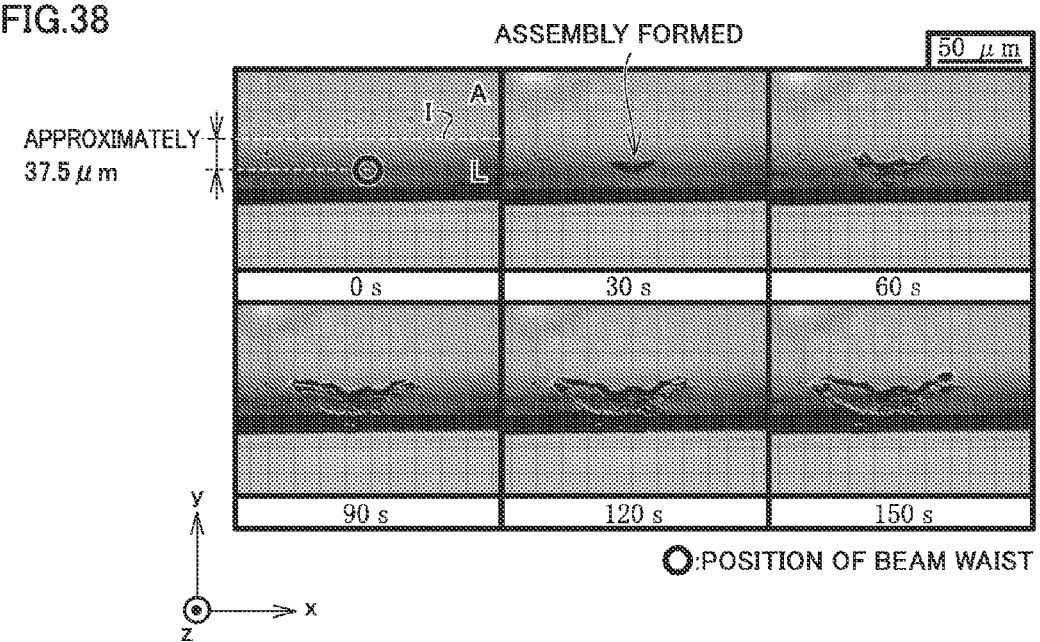
FIG. 38 shows successive photographic images (or optical transmission images) of a gas-liquid interface formed in a micro channel having a liquid mixture (volume: 1 μL) introduced therein, that are obtained after light irradiation is started, as obtained in a vicinity of a beam waist via an objective lens having a magnification of 40 times, the liquid mixture being a liquid mixture of a dispersion liquid of gold nanoparticles modified with the first probe DNA (concentration: 5.0 nM), a dispersion liquid of gold nanoparticles modified with the second probe DNA (concentration: 5.0 nM), and a diluted dispersion liquid of a complementary DNA (concentration: 100 pM).

FIG. 37 is an optical transmission image of a vicinity of a gas-liquid interface formed in the micro channel, as obtained via an objective lens of a magnification of 10 times before light irradiation starts. FIG. 38 presents successive photographic images (or optical transmission images) of a vicinity of the beam waist in micro channel 620 after light irradiation started.

FIGS. 37 and 38 show a state in a vicinity of the beam waist in a vicinity of a gas-liquid interface formed in micro channel 620 having introduced therein a liquid mixture (volume: 1 µL) of a dispersion liquid of gold nanoparticles 11 modified with probe DNA 13 (concentration: 5.0 nM), a dispersion liquid of gold nanoparticles 12 modified with probe DNA 14 (concentration: 5.0 nM), and a diluted dispersion liquid of a complementary DNA (concentration: 100 pM) of equal amounts. The dispersion liquid of gold nanoparticle 11, the dispersion liquid of gold nanoparticle 12, and the diluted dispersion liquid of the complementary DNA are equivalent in concentration to those described with reference to FIG. 29. Objective lens 103 has a magnification of 40 times.

With reference to FIG. 38, an assembly of gold nanoparticles is formed in a vicinity of the beam waist within 30 seconds, similarly as shown in the successive photographs shown in FIG. 29(A). In FIG. 38, however, a gas-liquid interface different in geometry from that of FIG. 29(A) is presented, and accordingly, how the gold nanoparticle assembly is formed is slightly different. Note that although not shown in the figure, when an absorption spectrum presented in a vicinity of the beam waist is measured, an absorbance increasing as time elapses and a peak shifting as time elapses are confirmed, similarly as has been confirmed in the absorption spectrum shown in FIG. 29(B)

If micro channel 620 has a width larger than the laser spot's size (or diameter), a portion of gold nanoparticles 11 and 12 and target DNA 18 dispersed in the liquid may pass through micro channel 620 without passing across the laser spot. Accordingly, preferably, micro channel 620 and the laser spot have a width and a diameter, respectively, determined to have a relationship in magnitude so that micro channel 620 has the width equal to or smaller than the diameter of the laser spot. Note, however, that, as shown in FIG. 36 to FIG. 38, if micro channel 620 has a width (350 µm) larger than the laser spot's diameter (several tens µm), formation of a gold nanoparticle assembly is confirmed. Thus, micro channel 620 having a width larger than the laser spot's diameter is not a requirement.

Seventh Embodiment

In a seventh embodiment will be described an effect of a sample bearing surface's affinity for a sample's liquid (or dispersion medium). Specifically, a super-hydrophilic substrate is used. A detection device that is used in the present embodiment is equivalent in configuration to the FIG. 4 detection device 100 and accordingly, the detection device will not be described repeatedly. Hereafter initially a comparative example using a hydrophobic substrate will be described.

Figure 39:
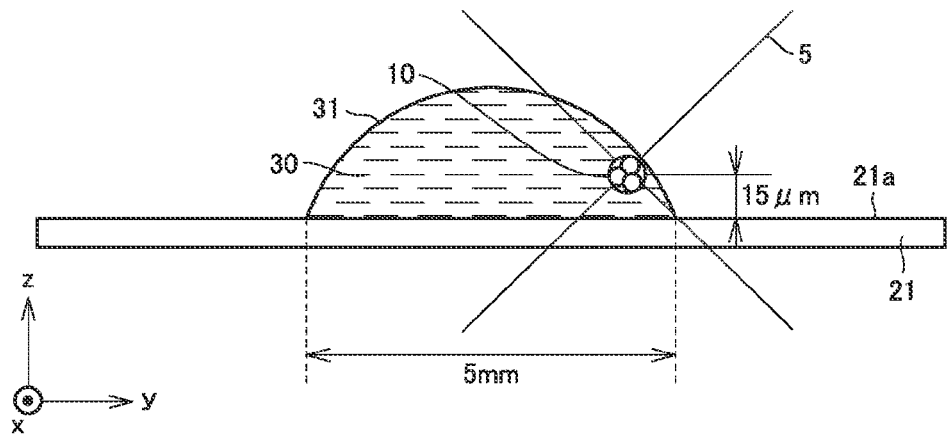
FIG. 39 is an enlarged view of a configuration in a vicinity of a kit using a hydrophobic substrate.

FIG. 39 is an enlarged view of a configuration in a vicinity of a kit using a hydrophobic substrate. With reference to FIG. 39, substrate 21 is a sheet glass (e.g., a cover glass) equivalent to that used in the first embodiment, and has a hydrophobic upper surface 21*a*.

Sample 30 dropped on substrate 21 had a concentration of 10 nM and a volume of 5 µL. In other words, sample 30 contained a complementary DNA in an amount of substance of 10 nM×5 µL=50 fmol (1 fmol=$10^{-15}$ mol). The droplet had a diameter of 5 mm. In this case, an optical system was adjusted to position a beam waist at a perimeter of the droplet that is 15 µm away from the surface of the substrate. The beam waist had a laser output of 0.2 W.

Figure 40:
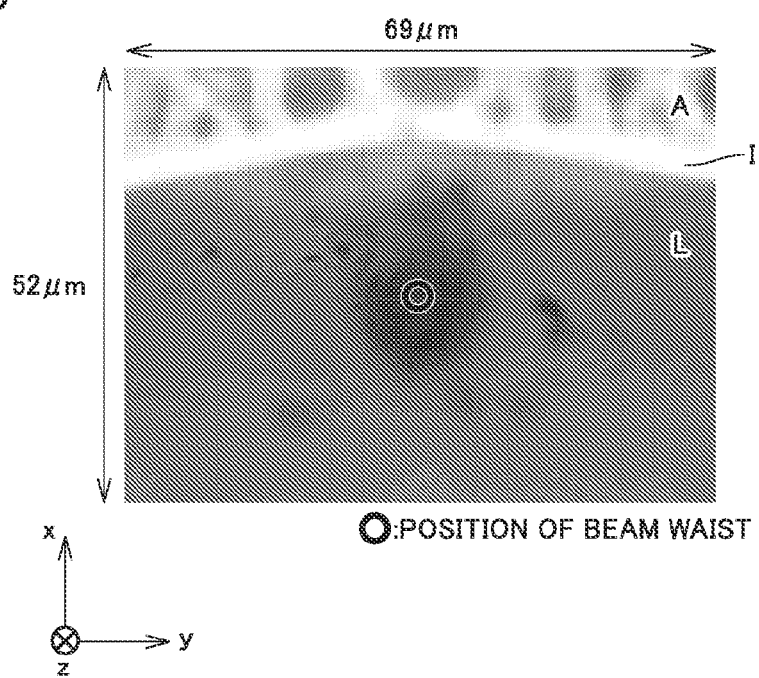
FIG. 40 is an optical transmission image of a diluted dispersion liquid of a complementary DNA on a hydrophobic substrate in a vicinity of a beam waist after light irradiation.

FIG. 40 is an image of a diluted dispersion liquid of a complementary DNA on the hydrophobic substrate in a vicinity of the beam waist after light irradiation. With reference to FIG. 40, when hydrophobic substrate 21 is used, a gold nanoparticle assembly is formed when the beam waist is positioned adjacent to an edge of the droplet with respect to the horizontal direction (or the xy plane), i.e., when the beam waist is positioned in a vicinity of gas-liquid interface (I). On the other hand, although not shown in the figure, when laser light 5 is radiated with the beam waist positioned in a vicinity of the center of the droplet, there is not formed any substantial gold nanoparticle assembly.

Figure 41:
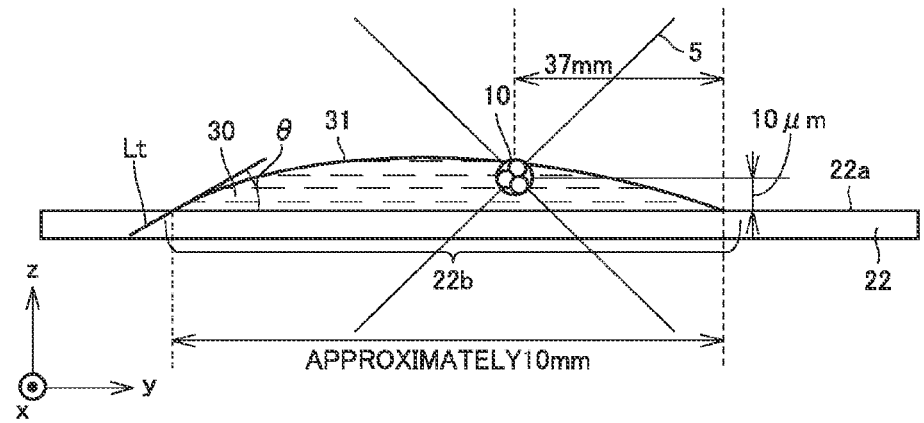
FIG. 41 is an enlarged view of a configuration in a vicinity of a kit super-hydrophilic substrate.

FIG. 41 is an enlarged view of a configuration in a vicinity of a kit using a super-hydrophilic substrate. With reference to FIG. 41, substrate 22 is a cover glass having an upper surface 22a processed to be super-hydrophilic. Note that while substrate 22 has upper surface 22a processed to be entirely super-hydrophilic, it may have upper surface 22a partially so processed. In other words, substrate 22 is only required to have upper surface 22a with at least a sample liquid holding region 22b having super-hydrophilicity.

Substrate 22 can be made super-hydrophilic in any of various known methods. In the present embodiment, upper surface 22a sufficiently cleaned with acetone was sprayed with a super-hydrophilic coating agent (a cell face coat produced by MARUSYO SANGYO CO., LTD.). Furthermore, substrate 22 thus sprayed was dried at 60 degrees centigrade for 30 minutes. Note that substrate 22 can also be made super-hydrophilic by sufficiently cleaning upper surface 22a with ethanol, spraying the cleaned surface with a super-hydrophilic coating agent, and air-drying the sprayed substrate for one day or more.

Sample 30 dropped on substrate 22 had a concentration of 100 pM and a volume V of 5 μL. In other words, sample 30 contained a complementary DNA in an amount of substance of 100 pM×5 μL=500 amol (1 amol=$10^{-18}$ mol). Upper surface 22a processed to be super hydrophilic allows the droplet to spread thereon and the droplet had a radius R of 5 mm.

As has been described in the first embodiment, when sample 30 has volume V, radius R and maximum height H, a relational expression of $V=2\pi R^2 H/3$ is established. When the relational expression has V and R substituted by 5 μL and 5 mm, respectively, H=0.287 mm is obtained. Accordingly, the droplet's tangent Lt and the substrate 22 upper surface 22a form a contact angle θ=3.3 degrees based on a relational expression of tan θ=(0.287/5)=0.0573. Note that for a hydrophobic substrate shown in FIG. 39, contact angle θ is calculated to be 24.7 degrees.

In this case, an optical system was adjusted to position a beam waist in a vicinity of the center of the droplet in a range within 15 μm as measured from upper surface 22a. The laser light at the beam waist had an output of 0.2 W, similarly as provided when the hydrophobic substrate is used.

Figure 42:
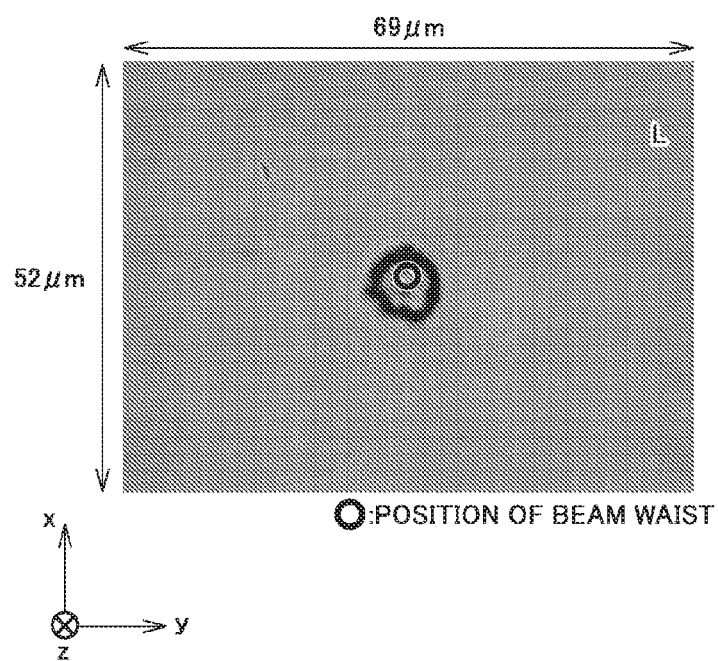
FIG. 42 is an optical transmission image of a diluted dispersion liquid of a complementary DNA on a super-hydrophilic substrate in a vicinity of a beam waist after light irradiation.

FIG. 42 is an image of a diluted dispersion liquid of a complementary DNA on the super hydrophilic substrate in a vicinity of the beam waist after light irradiation. With reference to FIG. 42, when super hydrophilic substrate 22 is used, then, even with the beam waist located in a vicinity of the center of the droplet, it is confirmed that a gold nanoparticle assembly is formed about 40 seconds after light irradiation is started.

Thus when a super hydrophilic substrate is compared with a hydrophobic substrate, the former allows a gold nanoparticle assembly to be formed in a wide area in the horizontal direction (or in a direction along the substrate's surface) including a vicinity of the center of the substrate. The present embodiment can thus eliminate the necessity of adjusting the beam waist to be positioned precisely at a position adjacent to a perimeter of a droplet. This allows increased tolerance in positionally adjusting the focal point of objective lens 103 (see FIG. 4) in the direction along the substrate's surface.

It should be understood that the embodiments disclosed herein have been described for the purpose of illustration only and in a non-restrictive manner in any respect. The scope of the present invention is defined by the terms of the claims, rather than the description above, and is intended to include any modifications within the meaning and scope equivalent to the terms of the claims.

REFERENCE SIGNS LIST

10: gold nanoparticle assembly; 11, 12: gold nanoparticle; 13, 14: probe DNA; 18: target DNA; 18B-18D: DNA; 5: laser light; 6: white light; 20: kit; 21: substrate; 24: liquid level guide; 30: sample; 31: gas-liquid interface; 100, 200, 400, 500: detection device; 101: optical trapping light source; 102: illumination light source; 103, 405: objective lens; 104: optical component; 105, 508: spectroscope; 106, 506: computation unit; 107: optical probe; 108: image pick-up device; 109: laser displacement meter; 110, 111: optical fiber; 112: adjustment mechanism; 114: xyz-axis stage; 115: immersion oil; 40: DNA chip; 41, 411, 412: spot; 406, 407: filter; 408: CCD camera; 600: micro channel chip; 610: inlet; 620: micro channel; 630: outlet; 641-643: valve.

The invention claimed is:

1. A detection device for detecting an analyte, comprising:
- a plurality of metallic nanoparticles each modified with a host molecule allowing said analyte to specifically adhere thereto;
- a polarized light irradiated to a liquid containing a specimen and said plurality of metallic nanoparticles with an intensity configured to assemble said plurality of metallic nanoparticles together at a position by said analyte and said host molecule adhering to each other, said polarized light heating said liquid in a vicinity of said position at which said liquid is irradiated with said polarized light configured to cause a convection flow and to grow said metallic nanoparticle assembly;
- an objective lens configured to focus and introduce said polarized light into said liquid;
- a photoreceiver that receives at least either one of transparent light and scattered light from said liquid; and
- a detector that detects said analyte based on a signal received from said photoreceiver.

2. The detection device for detecting an analyte according to claim 1, further comprising an adjustment mechanism configured to adjust a distance between said objective lens and a gas-liquid interface of said liquid and a gas surrounding said liquid so that said objective lens has a focal point in said liquid in a vicinity of said gas-liquid interface.

3. The detection device for detecting an analyte according to claim 1, wherein said plurality of metallic nanoparticles include:
- a plurality of first metallic nanoparticles each modified with a first host molecule; and
- a plurality of second metallic nanoparticles each modified with a second host molecule.

4. The detection device for detecting an analyte according to claim 3, wherein:
said analyte is a target DNA; and
said first and second host molecules are each a probe DNA hybridizing with said target DNA.

5. The detection device for detecting an analyte according to claim 4, wherein:
said target DNA is one of a first target DNA having a base sequence complementary to said probe DNA and a second target DNA having a base sequence partially different from said first target DNA;
said photoreceiver includes a spectroscope that measures a spectrum of said liquid; and
said detector determines whether said analyte is said first target DNA or said second target DNA, based on how said spectrum measured with said spectroscope varies with time.

6. The detection device for detecting an analyte according to claim 3, said first and second host molecules being first and second probe DNAs, respectively, said plurality of metallic nanoparticles being each modified with said first probe DNA, the detection device further comprising a substrate having a plurality of spots each having said second probe DNA fixed thereto, wherein:
said analyte is one of a first target DNA having a base sequence complementary to said first and second probe DNAs and a second target DNA having a base sequence partially different from said first target DNA;
said photoreceiver includes a spectroscope that measures a spectrum of said liquid; and
said detector determines whether said analyte is said first target DNA or said second target DNA, based on how said spectrum measured with said spectroscope varies with time.

7. The detection device for detecting an analyte according to claim 1, wherein:
said analyte is an antigen; and
said host molecule is an antibody causing an antigen-antibody reaction with said antigen.

8. The detection device for detecting an analyte according to claim 1, further comprising a second light source that emits light for measuring a spectrum of said liquid, wherein:
said photoreceiver includes a spectroscope that measures said spectrum of said liquid;
said detector detects said analyte based on said spectrum measured with said spectroscope; and
said second light source emits substantially monochromatic light associated with one or more ranges corresponding to twice a full width at half maximum of a peak of localized surface plasmon resonance of said gold nanoparticle.

9. The detection device for detecting an analyte according to claim 1, further comprising a second light source that emits light for measuring a spectrum of said liquid, wherein:
said photoreceiver includes a spectroscope that measures said spectrum of said liquid;
said detector detects said analyte based on said spectrum measured with said spectroscope; and
said spectrum measured with said spectroscope is an absorption spectrum of localized surface plasmon resonance.

10. The detection device for detecting an analyte according to claim 1, further comprising a second light source that emits light for measuring a spectrum of said liquid, wherein:
said photoreceiver includes a spectroscope that measures said spectrum of said liquid;
said detector detects said analyte based on said spectrum measured with said spectroscope; and
said spectrum measured with said spectroscope is a surface enhanced Raman scattering (SERS) spectrum.

11. The detection device for detecting an analyte according to claim 1, said plurality of metallic nanoparticles being each modified with a host molecule, the detection device further comprising a substrate having a plurality of spots each having a second host molecule fixed thereto.

12. The detection device for detecting an analyte according to claim 1, further comprising a substrate that holds said liquid, wherein a region of said substrate at least holding said liquid is super-hydrophilic.

13. The detection device for detecting an analyte according to claim 1, wherein a focal point of said objective lens being positioned at a portion of said liquid so that said portion of said liquid causes said convection flow.

14. The detection device for detecting an analyte according to claim 13, wherein the intensity of said polarized light being determined so that said metallic nanoparticle assembly grows until a diameter of said metallic nanoparticle assembly becomes larger than a beam diameter of said polarized light focused by said objective lens.

15. The detection device for detecting an analyte according to claim 14, wherein a wavelength of said polarized light being determined so that said metallic nanoparticle assembly grows until a diameter of said metallic nanoparticle assembly becomes larger than a beam diameter of said polarized light focused by said objective lens.

16. The detection device for detecting an analyte according to claim 13, wherein the intensity of said polarized light being determined so that the growth of said metallic nanoparticle assembly occurs within a few minutes from the beginning of the irradiation of said polarized light.

17. The detection device for detecting an analyte according to claim 16, wherein a wavelength of said polarized light being determined so that the growth of said metallic nanoparticle assembly occurs within a few minutes from the beginning of the irradiation of said polarized light.

18. The detection device for detecting an analyte, comprising:
a plurality of metallic nanoparticles each modified with a host molecule allowing said analyte to specifically adhere thereto;
a polarized light irradiated to a liquid containing a specimen and said plurality of metallic nanoparticles with an intensity configured to assemble said plurality of metallic nanoparticles together at a position by said analyte and said host molecule adhering to each other, said polarized light heating said liquid in a vicinity of said position at which said liquid is irradiated with said polarized light configured to cause a convection flow and to grow said metallic nanoparticle assembly;
an objective lens configured to focus and introduce said polarized light into said a liquid;
a substrate having a micro channel passing said liquid, wherein the light focused by said objective lens is introduced into said micro channel;
a photoreceiver that receives at least either one of transparent light and scattered light from said liquid; and
a detector that detects said analyte based on a signal received from said photoreceiver.

* * * * *

SEQUENCE LISTING

```
<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (12)..(12)
<223> OTHER INFORMATION: "SH" (Thiol group) on 3' end

<400> SEQUENCE: 1
tttttttttt tt                                                         12

<210> SEQ ID NO 2
<211> LENGTH: 12
<212> TYPE: DNA
<213> ORGANISM: Artificial Sequence
<220> FEATURE:
```

```
<223> OTHER INFORMATION: Synthetic
<220> FEATURE:
<221> NAME/KEY: modified_base
<222> LOCATION: (1)..(1)
<223> OTHER INFORMATION: "SH" (Thiol group) on 5' end

<400> SEQUENCE: 2
tttttttttt tt                                                          12

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
aaaaaaaaaa aaaaaaaaaa aaaa                                             24

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
tttttttttt tttttttttt tttt                                             24

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
aaaaaaaaaa aattttttttt tttt                                            24

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
tatatatata tatatatata tata                                             24
```